(12) United States Patent
Cholli et al.

(10) Patent No.: US 10,683,455 B2
(45) Date of Patent: Jun. 16, 2020

(54) MACROMOLECULAR ANTIOXIDANTS BASED ON DUAL TYPE MOIETY PER MOLECULE: STRUCTURES, METHODS OF MAKING AND USING THE SAME

(71) Applicant: Polnox Corporation, Lowell, MA (US)

(72) Inventors: Ashok L. Cholli, Lowell, MA (US); Vijayendra Kumar, Lowell, MA (US)

(73) Assignee: Polnox Corporation, Lowell, MA (US)

( * ) Notice: Subject to any disclaimer, the term of this patent is extended or adjusted under 35 U.S.C. 154(b) by 0 days.

(21) Appl. No.: 16/372,594

(22) Filed: Apr. 2, 2019

(65) Prior Publication Data

US 2019/0292454 A1    Sep. 26, 2019

Related U.S. Application Data

(62) Division of application No. 15/038,361, filed as application No. PCT/US2014/066935 on Nov. 21, 2014, now Pat. No. 10,294,423.

(60) Provisional application No. 61/907,863, filed on Nov. 22, 2013.

(51) Int. Cl.

| | | |
|---|---|---|
| *C10M 133/16* | (2006.01) | |
| *C09K 15/24* | (2006.01) | |
| *C07C 213/00* | (2006.01) | |
| *C07C 217/28* | (2006.01) | |
| *C07C 217/42* | (2006.01) | |
| *C07C 231/02* | (2006.01) | |
| *C07C 235/34* | (2006.01) | |
| *C07D 251/34* | (2006.01) | |
| *C07D 251/52* | (2006.01) | |
| *C07C 209/60* | (2006.01) | |
| *C07C 213/02* | (2006.01) | |
| *C07C 235/38* | (2006.01) | |
| *C07D 251/30* | (2006.01) | |
| *C07D 251/46* | (2006.01) | |
| *C08K 5/20* | (2006.01) | |

(52) U.S. Cl.
CPC ............ *C09K 15/24* (2013.01); *C07C 209/60* (2013.01); *C07C 213/00* (2013.01); *C07C 213/02* (2013.01); *C07C 217/28* (2013.01); *C07C 217/42* (2013.01); *C07C 231/02* (2013.01); *C07C 235/34* (2013.01); *C07C 235/38* (2013.01); *C07D 251/30* (2013.01); *C07D 251/34* (2013.01); *C07D 251/46* (2013.01); *C07D 251/52* (2013.01); *C08K 5/20* (2013.01); *C10M 133/16* (2013.01); *C10M 2215/28* (2013.01)

(58) Field of Classification Search
CPC .... C09K 15/24; C07D 251/52; C07D 251/46; C07D 251/30; C07D 251/34; C07C 235/38; C07C 213/00; C07C 217/28; C07C 217/42; C07C 231/02; C07C 235/34; C07C 213/02; C07C 209/60; C08K 5/20; C10M 133/16; C10M 2215/28

See application file for complete search history.

(56) References Cited

U.S. PATENT DOCUMENTS

| | | |
|---|---|---|
| 3,116,305 A | 12/1963 | Morris et al. |
| 3,294,836 A | 12/1966 | Peterson et al. |
| 3,441,545 A | 4/1969 | Blatz et al. |
| 3,459,704 A | 8/1969 | Peterson et al. |
| 3,557,245 A | 1/1971 | Phillips et al. |
| 3,632,785 A | 1/1972 | Bornstein |
| 3,645,970 A | 2/1972 | Kleiner |
| 3,649,667 A | 3/1972 | Song et al. |
| 3,655,831 A | 4/1972 | Friedman |
| 3,870,680 A | 3/1975 | Schurdak |
| 3,907,939 A | 9/1975 | Robin et al. |
| 3,953,402 A | 4/1976 | Kline |
| 3,965,039 A | 6/1976 | Chaplits et al. |
| 3,983,091 A | 9/1976 | Gloth et al. |
| 3,994,828 A | 11/1976 | Zaffaroni |
| 3,996,160 A | 12/1976 | Dale et al. |
| 3,996,198 A | 12/1976 | Wang et al. |
| 4,054,676 A | 10/1977 | Weinshenker et al. |
| 4,094,857 A | 6/1978 | Wolfe, Jr. |
| 4,096,319 A | 6/1978 | Willette et al. |
| 4,097,464 A | 6/1978 | Kline |

(Continued)

FOREIGN PATENT DOCUMENTS

| | | |
|---|---|---|
| CS | 111291 | 6/1964 |
| DE | 197 47 644 A1 | 5/1999 |

(Continued)

OTHER PUBLICATIONS

Akkara, J.A., et al., "Hematin-Catalyzed Polymerization of Phenol Compounds," Macromolecules, 33(7):2377-2382 (2000).
Akkara, J.A., et al., "Synthesis and Characterization of Polymers Produced by Horseradish Peroxidase in Dioxane," *J. of Polymer Science: Part A: Polymer Chemistry*, 29(11):1561-1574 (1991).
Al-Malaika, S and Suharty, N., "Reactive Processing of Polymers: Mechanisms of Grafting Reactions of Functional Antioxidants on Polyolefins in the Presence of a Coagent," Polymer Degradation and Stability 49: 77-89 (1995).

(Continued)

*Primary Examiner* — Taiwo Oladapo
(74) *Attorney, Agent, or Firm* — Foley Hoag LLP

(57) ABSTRACT

Disclosed are compounds represented by structural formula

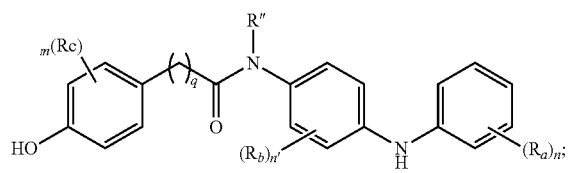

methods of producing compounds represented by structural formula, and their use in inhibiting oxidation in an oxidizable material.

7 Claims, No Drawings

(56) References Cited

U.S. PATENT DOCUMENTS

| | | | |
|---|---|---|---|
| 4,098,829 A | 7/1978 | Weinshenker et al. |
| 4,107,144 A | 8/1978 | Russell et al. |
| 4,136,055 A | 1/1979 | Lyons |
| 4,202,816 A | 5/1980 | Moser et al. |
| 4,205,151 A | 5/1980 | Dale et al. |
| 4,213,892 A | 7/1980 | Scott |
| 4,219,453 A | 8/1980 | Sakurai et al. |
| 4,267,358 A | 5/1981 | Hechenbleikner et al. |
| 4,281,192 A | 7/1981 | Jacquet et al. |
| 4,283,572 A | 8/1981 | Klicker |
| 4,317,933 A | 3/1982 | Parker |
| 4,341,879 A | 7/1982 | Sugio et al. |
| 4,355,148 A | 10/1982 | Layer et al. |
| 4,377,666 A | 3/1983 | Farrar |
| 4,380,554 A | 4/1983 | Serres, Jr. |
| 4,447,657 A | 5/1984 | Firth et al. |
| 4,465,871 A | 8/1984 | Firth et al. |
| 4,480,108 A | 10/1984 | Foster |
| 4,510,296 A | 4/1985 | Hergenrother |
| 4,511,491 A | 4/1985 | Ishii et al. |
| 4,634,728 A | 1/1987 | Dunski et al. |
| 4,690,995 A | 9/1987 | Keskey et al. |
| 4,761,247 A | 8/1988 | Rei et al. |
| 4,788,282 A | 11/1988 | Deziel |
| 4,824,929 A | 4/1989 | Arimatsu et al. |
| 4,849,503 A | 7/1989 | Cotter et al. |
| 4,855,345 A | 8/1989 | Rosenberger et al. |
| 4,857,596 A | 8/1989 | MacLeay et al. |
| 4,859,736 A | 8/1989 | Rink |
| 4,870,214 A | 9/1989 | Mina et al. |
| 4,894,263 A | 1/1990 | Dubois et al. |
| 4,897,438 A | 1/1990 | Kikuchi et al. |
| 4,900,671 A | 2/1990 | Pokora et al. |
| 4,925,591 A | 5/1990 | Nakauchi et al. |
| 4,968,759 A | 11/1990 | Kikuchi et al. |
| 4,977,004 A | 12/1990 | Bettle, III et al. |
| 4,978,739 A | 12/1990 | Arnone et al. |
| 4,981,917 A | 1/1991 | MacLeay et al. |
| 4,994,628 A | 2/1991 | Goddard et al. |
| 5,004,781 A | 4/1991 | Rink |
| 5,013,470 A | 5/1991 | Benfaremo |
| 5,017,727 A | 5/1991 | Olivier |
| 5,082,358 A | 1/1992 | Tabata et al. |
| 5,102,962 A | 4/1992 | Kikuchi et al. |
| 5,117,063 A | 5/1992 | Stern et al. |
| 5,143,828 A | 9/1992 | Akkara et al. |
| 5,153,298 A | 10/1992 | Pokora et al. |
| 5,155,153 A | 10/1992 | Neri et al. |
| 5,185,391 A | 2/1993 | Stokich, Jr. |
| 5,185,407 A | 2/1993 | Wong |
| 5,188,953 A | 2/1993 | Johnson et al. |
| 5,191,008 A | 3/1993 | Frost et al. |
| 5,196,142 A | 3/1993 | Mollet et al. |
| 5,206,303 A | 4/1993 | Tse et al. |
| 5,207,939 A | 5/1993 | Farng et al. |
| 5,212,044 A | 5/1993 | Liang et al. |
| 5,274,060 A | 12/1993 | Schadeli |
| 5,278,055 A | 1/1994 | Cyrus, Jr. et al. |
| 5,304,589 A | 4/1994 | Davidson et al. |
| 5,320,889 A | 6/1994 | Bettle, III |
| 5,444,143 A | 8/1995 | Ohta et al. |
| 5,449,715 A | 9/1995 | Plochocka et al. |
| 5,498,809 A | 3/1996 | Emert et al. |
| RE35,247 E | 5/1996 | Cyrus, Jr. et al. |
| 5,516,856 A | 5/1996 | Sanchez |
| 5,541,091 A | 7/1996 | Wheeler et al. |
| 5,565,300 A | 10/1996 | Uenishi et al. |
| 5,574,118 A | 11/1996 | Olivier |
| 5,652,201 A | 7/1997 | Papay et al. |
| 5,739,341 A | 4/1998 | Dubs et al. |
| 5,763,374 A * | 6/1998 | Sakai .................. C10M 145/14 508/469 |
| 5,834,544 A * | 11/1998 | Lin ....................... C07C 235/38 524/217 |
| 5,837,798 A | 11/1998 | Hutchings et al. |
| 5,869,592 A | 2/1999 | Gagne et al. |
| 5,911,937 A | 6/1999 | Hekal |
| 5,994,498 A | 11/1999 | Tripathy et al. |
| 6,018,018 A | 1/2000 | Samuelson et al. |
| 6,040,111 A | 3/2000 | Karasawa et al. |
| 6,046,263 A | 4/2000 | Rasberger et al. |
| 6,096,695 A | 8/2000 | Lam et al. |
| 6,096,859 A | 8/2000 | Akkara et al. |
| 6,150,491 A | 11/2000 | Akkara |
| 6,232,101 B1 | 5/2001 | Budolfsen et al. |
| 6,232,314 B1 | 5/2001 | Jarrott et al. |
| 6,242,010 B1 | 6/2001 | Hersh |
| 6,306,991 B1 | 10/2001 | Fischer et al. |
| 6,342,549 B1 | 1/2002 | Hirose et al. |
| 6,444,450 B2 | 9/2002 | Akkara et al. |
| 6,537,546 B2 | 3/2003 | Echigo et al. |
| 6,569,651 B1 | 5/2003 | Samuelson et al. |
| 6,646,035 B2 | 11/2003 | Koch et al. |
| 6,723,815 B2 | 4/2004 | Callaghan et al. |
| 6,743,525 B2 | 6/2004 | Bernsten et al. |
| 6,770,785 B1 | 8/2004 | Desai et al. |
| 6,794,480 B2 | 9/2004 | Goto et al. |
| 6,800,228 B1 | 10/2004 | Semen |
| 6,828,364 B2 | 12/2004 | Gugumus |
| 6,846,859 B2 | 1/2005 | Coffy et al. |
| 6,933,319 B2 | 8/2005 | Browning et al. |
| 7,087,799 B2 | 8/2006 | Tsuihiji et al. |
| 7,132,496 B2 | 11/2006 | Kerres et al. |
| 7,169,844 B2 | 1/2007 | Inokami |
| 7,205,350 B2 | 4/2007 | Thibaut |
| 7,223,432 B2 | 5/2007 | Cholli et al. |
| 7,262,319 B2 | 8/2007 | Rehm et al. |
| 7,323,511 B2 | 1/2008 | Cholli et al. |
| 7,507,454 B2 | 3/2009 | Cholli et al. |
| 7,595,074 B2 | 9/2009 | Cholli et al. |
| 7,601,378 B2 | 10/2009 | Cholli et al. |
| 7,678,877 B2 | 3/2010 | Yang et al. |
| 7,705,075 B2 | 4/2010 | Kumar et al. |
| 7,705,176 B2 | 4/2010 | Cholli et al. |
| 7,705,185 B2 | 4/2010 | Kumar et al. |
| 7,727,571 B2 | 6/2010 | Cholli et al. |
| 7,754,267 B2 | 7/2010 | Cholli et al. |
| 7,767,853 B2 | 8/2010 | Cholli et al. |
| 7,799,948 B2 | 9/2010 | Kumar et al. |
| 7,902,317 B2 | 3/2011 | Kumar et al. |
| 7,923,587 B2 | 4/2011 | Cholli |
| 7,956,153 B2 | 6/2011 | Cholli et al. |
| 8,008,423 B2 | 8/2011 | Kumar et al. |
| 8,039,673 B2 | 10/2011 | Cholli et al. |
| 8,080,689 B2 | 12/2011 | Kumar |
| 8,242,230 B2 | 8/2012 | Cholli et al. |
| 8,252,884 B2 | 8/2012 | Kumar et al. |
| 8,481,670 B2 | 7/2013 | Kumar et al. |
| 8,598,382 B2 | 12/2013 | Cholli et al. |
| 8,691,933 B2 | 4/2014 | Kumar et al. |
| 8,710,266 B2 | 4/2014 | Kumar et al. |
| 8,846,847 B2 | 9/2014 | Cholli et al. |
| 8,927,472 B2 | 1/2015 | Cholli et al. |
| 9,193,675 B2 | 11/2015 | Cholli et al. |
| 9,388,120 B2 | 7/2016 | Kumar et al. |
| 9,523,060 B2 | 12/2016 | Cholli et al. |
| 9,950,990 B2 | 4/2018 | Cholli et al. |
| 2001/0041203 A1 | 11/2001 | Uno et al. |
| 2002/0007020 A1 | 1/2002 | Higahimura et al. |
| 2002/0049166 A1 | 4/2002 | Romanczyk, Jr. et al. |
| 2002/0128493 A1 | 9/2002 | Romanczyk, Jr. et al. |
| 2002/0143025 A1 | 10/2002 | Pratt et al. |
| 2002/0183470 A1 | 12/2002 | Tripathy et al. |
| 2003/0030033 A1 | 2/2003 | Duyck et al. |
| 2003/0078346 A1 | 4/2003 | Nakamura et al. |
| 2003/0091837 A1 | 5/2003 | Aoki |
| 2003/0176620 A1 | 9/2003 | Romanczyk, Jr. et al. |
| 2003/0191242 A1 | 10/2003 | Zedda et al. |
| 2003/0195128 A1 * | 10/2003 | Deckman ............. C10M 111/04 508/591 |
| 2003/0229196 A1 | 12/2003 | Braat et al. |
| 2003/0230743 A1 | 12/2003 | Cholli et al. |
| 2004/0015021 A1 | 1/2004 | Adams et al. |
| 2004/0063783 A1 | 4/2004 | Lardy et al. |

(56) References Cited

U.S. PATENT DOCUMENTS

| | | |
|---|---|---|
| 2004/0164279 A1 | 8/2004 | Stevenson et al. |
| 2004/0171787 A1 | 9/2004 | Shim |
| 2004/0180994 A1 | 9/2004 | Pearson et al. |
| 2004/0186167 A1 | 9/2004 | Dou et al. |
| 2004/0186214 A1 | 9/2004 | Li et al. |
| 2004/0198875 A1 | 10/2004 | Kaprinidis et al. |
| 2004/0214935 A1 | 10/2004 | Cholli et al. |
| 2004/0260114 A1 | 12/2004 | Lee et al. |
| 2005/0170978 A1 | 8/2005 | Migdal et al. |
| 2005/0209379 A1 | 9/2005 | Botkin et al. |
| 2005/0238789 A1 | 10/2005 | Cholli et al. |
| 2005/0242328 A1 | 11/2005 | Baranski |
| 2006/0029706 A1 | 2/2006 | Cholli et al. |
| 2006/0040833 A1 | 2/2006 | Al-Akhdar et al. |
| 2006/0041087 A1 | 2/2006 | Cholli |
| 2006/0041094 A1 | 2/2006 | Cholli |
| 2006/0128929 A1 | 6/2006 | Yang et al. |
| 2006/0128930 A1 | 6/2006 | Dhawan et al. |
| 2006/0128931 A1 | 6/2006 | Kumar et al. |
| 2006/0128939 A1 | 6/2006 | Kumar et al. |
| 2006/0154818 A1 | 7/2006 | Destro et al. |
| 2006/0189820 A1 | 8/2006 | Rehm et al. |
| 2006/0189824 A1 | 8/2006 | Kumar et al. |
| 2006/0208227 A1 | 9/2006 | Shiraki |
| 2006/0233741 A1 | 10/2006 | Kumar et al. |
| 2007/0010632 A1 | 1/2007 | Kaplan et al. |
| 2007/0106059 A1 | 5/2007 | Cholli et al. |
| 2007/0135539 A1 | 6/2007 | Cholli et al. |
| 2007/0149660 A1 | 6/2007 | Kumar et al. |
| 2007/0154430 A1 | 7/2007 | Cholli et al. |
| 2007/0154608 A1 | 7/2007 | Cholli et al. |
| 2007/0154720 A1 | 7/2007 | Cholli et al. |
| 2007/0161522 A1 | 7/2007 | Cholli et al. |
| 2008/0249335 A1 | 10/2008 | Cholli et al. |
| 2008/0293856 A1 | 11/2008 | Kumar et al. |
| 2008/0311065 A1 | 12/2008 | Cholli |
| 2009/0184294 A1 | 7/2009 | Cholli et al. |
| 2010/0084607 A1 | 4/2010 | Cholli et al. |
| 2010/0105585 A1* | 4/2010 | Carey ............... C10M 141/10 508/162 |
| 2011/0040125 A1 | 2/2011 | Kumar et al. |
| 2011/0282098 A1 | 11/2011 | Cholli et al. |
| 2012/0004150 A1 | 1/2012 | Cholli et al. |
| 2012/0071596 A1 | 3/2012 | Kumar et al. |
| 2012/0123145 A1 | 5/2012 | Cholli et al. |
| 2012/0142968 A1 | 6/2012 | Kumar et al. |
| 2013/0041171 A1 | 2/2013 | Cholli et al. |
| 2013/0072586 A1 | 3/2013 | Kumar et al. |
| 2013/0130955 A1 | 5/2013 | Cholli et al. |
| 2014/0011901 A1 | 1/2014 | Kumar et al. |
| 2014/0014880 A1 | 1/2014 | Cholli et al. |
| 2014/0316163 A1 | 10/2014 | Kumar et al. |
| 2015/0159109 A1 | 6/2015 | Cholli |
| 2016/0115117 A1 | 4/2016 | Cholli et al. |
| 2018/0251695 A1 | 9/2018 | Cholli et al. |

FOREIGN PATENT DOCUMENTS

| | | |
|---|---|---|
| DE | 198 43 875 A1 | 3/2000 |
| EP | 0 181 023 A1 | 5/1986 |
| EP | 0 289 077 A2 | 11/1988 |
| EP | 0 358 157 | 3/1990 |
| EP | 0 404 039 A1 | 12/1990 |
| EP | 0 618 203 A1 | 10/1994 |
| EP | 0 688 805 A1 | 12/1995 |
| EP | 1 067 144 A1 | 1/2001 |
| EP | 1 468 968 A1 | 10/2004 |
| FR | 2 183 973 | 1/1974 |
| GB | 1 042 639 | 8/1964 |
| GB | 1 283 103 | 7/1972 |
| GB | 1 320 169 | 6/1973 |
| GB | 1 372 042 | 10/1974 |
| GB | 1 389 442 | 4/1975 |
| GB | 1 469 245 | 4/1977 |
| GB | 1 482 649 | 8/1977 |
| JP | 69002715 B | 1/1966 |
| JP | 43016392 B4 | 7/1968 |
| JP | 43018453 | 8/1968 |
| JP | 44024274 | 10/1969 |
| JP | 44028850 | 11/1969 |
| JP | 45 2980 | 1/1970 |
| JP | 49 29339 | 3/1974 |
| JP | 57085366 A | 5/1982 |
| JP | 59025814 | 2/1984 |
| JP | 59197447 | 11/1984 |
| JP | 60-199832 | 10/1985 |
| JP | 62249945 A1 | 10/1987 |
| JP | 05 199858 | 8/1993 |
| JP | 06135876 A | 5/1994 |
| JP | 06 247959 | 9/1994 |
| JP | 08027226 A | 1/1996 |
| JP | 09262069 | 10/1997 |
| JP | 09 328519 | 12/1997 |
| JP | 09 328521 | 12/1997 |
| JP | 9322784 A | 12/1997 |
| JP | 11-80063 | 3/1999 |
| JP | 11-158103 | 6/1999 |
| JP | 2003138258 | 5/2003 |
| NL | 7 905 000 | 3/1980 |
| WO | WO 92/20734 | 11/1992 |
| WO | WO 97/14678 A1 | 4/1997 |
| WO | WO 00/39064 | 7/2000 |
| WO | WO 01/18125 A1 | 3/2001 |
| WO | WO 01/48057 A1 | 7/2001 |
| WO | WO 02/28820 A1 | 4/2002 |
| WO | WO 02/079130 A1 | 10/2002 |
| WO | WO 03/087260 A1 | 10/2003 |
| WO | WO 03/102004 A1 | 12/2003 |
| WO | WO 2004/024070 A2 | 3/2004 |
| WO | WO 2004/050795 A2 | 6/2004 |
| WO | WO 2005/025513 A2 | 3/2005 |
| WO | WO 2005/025646 A2 | 3/2005 |
| WO | WO 2005/060500 A2 | 7/2005 |
| WO | WO 2005/070974 A2 | 8/2005 |
| WO | WO 2005/071005 A1 | 8/2005 |
| WO | WO 2006/014605 | 2/2006 |
| WO | WO 2006/014674 | 2/2006 |
| WO | WO 2006/018403 A1 | 2/2006 |
| WO | WO 2006/060800 | 6/2006 |
| WO | WO 2006/060801 A2 | 6/2006 |
| WO | WO 2006/060802 | 6/2006 |
| WO | WO 2006/060803 | 6/2006 |
| WO | WO 2006/091705 | 8/2006 |
| WO | WO 2006/104957 A2 | 10/2006 |
| WO | WO 2007/050985 | 5/2007 |
| WO | WO 2007/050987 | 5/2007 |
| WO | WO 2007/050991 | 5/2007 |
| WO | WO 2007/064843 | 6/2007 |
| WO | WO 2008/005358 A2 | 1/2008 |
| WO | WO 2009/139005 A1 | 11/2009 |
| WO | WO 2015/077635 A2 | 5/2015 |
| WO | WO 2018/160879 | 9/2018 |

OTHER PUBLICATIONS

Armengol, E., et al., "Acid Zeolites as Catalysts in Organic Reactions, tert-Butylation of Anthracene, Naphthalene and Thianthrene," *Appl. Catal. A* 149:411-423 (1997).

Ayyagari, M.S., et al., "Controlled Free-Radical Polymerization of Phenol Derivatives by Enzyme-Catalyzed Reactions in Organic Solvents," *Macromolecules*, 28(15):5192-5197 (1995).

Badamali, S.K., et al., "Influence of Aluminium Sources on the Synthesis and Catalytic Activity of Mesoporous AlMCM-41 Molecular Sieves," *Catal. Today* 63:291-295 (2000).

Belyaev, A., et al., "Structure-Activity Relationship of Diaryl Phosphonate Esters as Potent Irreversible Dipeptidyl Peptidase IV Inhibitors," *J. Med. Chem.*, 42(6):1041-1052 (1998).

Blokhin, Y.I., et al., "Phosphorylation of Dihydric Phenols with Amides of Phosphorous Acid," *Russian Chem. Bulletin*, 45(9):2250-2251 (1996).

(56) References Cited

OTHER PUBLICATIONS

Bruno, F.F., et al., "Enzymatic Template Synthesis of Polyphenol," Materials Research Society Symposium Proceedings vol. 600, Electroactive Polymers (EAP):255-259 (1999).
Chandra, K.G. and Sharma, M.M., "Alkylation of Phenol with MTBE and Other tert-butylethers:Cation Exchange Resins as Catalysts," Catal. Lett. 19(4):309-317 (1993).
Ciric-Marjanovic, et al., Chemical Oxidative Polymerization of Aminodiphenylamines, Journal of Physical Chemistry B, 112, 23: 6976-6987 (2008).
Coppinger, G.B., et al., "Photo-Fries Rearrangement of Aromatic Esters. Role of Steric and Electronic Factors" J. of Phy. Chem., 70(11):3479-3489 (1966).
Database Beilstein [online] Beilstein Institut Zur Förderung Der Chemischen Wissenschaften; XP002420027, Beilstein Registry No. 3517906.
Database Beilstein [online] Beilstein Institut Zur Förderung Der Chemischen Wissenschaften; XP002420028, Beilstein Registry No. 5840042.
Database Beilstein [online] Beilstein Institut Zur Förderung Der Chemischen Wissenschaften; XP002420029, Beilstein Registry No. 2311871.
Database Beilstein [online] Beilstein Institut Zur Förderung Der Chemischen Wissenschaften; XP002420030, Beilstein Registry No. 8876646.
Database Beilstein [online] Beilstein Institut Zur Förderung Der Chemischen Wissenschaften; XP002420031, Beilstein Registry No. 2271400.
Database Beilstein [online] Beilstein Institut Zur Förderung Der Chemischen Wissenschaften; XP002420032, Beilstein Registry No. 2212095.
Database Beilstein [online] Beilstein Institut Zur Förderung Der Chemischen Wissenschaften; XP002420033, Beilstein Registry No. 8941955.
Database Beilstein [online] Beilstein Institut Zur Förderung Der Chemischen Wissenschaften; XP002420034, Database Accession No. 2312425.
Database Beilstein [online] Beilstein Institut Zur Förderung Der Chemischen Wissenschaften; XP002420035, Beilstein Registry No. 905950.
Database Beilstein [online] Beilstein Institut Zur Förderung Der Chemischen Wissenschaften; XP002420036, Beilstein Registry No. 2140308.
Database Beilstein [online] Beilstein Institut Zur Förderung Der Chemischen Wissenschaften; XP002420037, Beilstein Registry No. 134886.
Database Beilstein [online] Beilstein Institut Zur Förderung Der Chemischen Wissenschaften; XP002420038, Beilstein Registry No. 1961007.
Database CA [online] Chemical Abstracts Service, Columbus, Ohio, US, XP-002429584, Database Accession No. 81::153647, Organic Phosphate Stabilizers for Polyamides and Polyurethanes, abstract, Minagawa, M. (1974).
Database Caplus [online] Chemical Abstracts Service, Columbus, Ohio, US, XP-002387095, Database Accession No. 1981:572206, Effectiveness of Inhibitors in the Oxidation of Jet Fuel with an Initiator, abstract, Kovalev, et al.
Devassy, B.M., et al., "Zirconia Supported Phosphotungstic Acid as an Efficient Catalyst for Resorcinol tert-Butylation and n-Heptane Hydroisomerization," J. Mol. Catalysis A: Chemical 221:113-119 (2004).
Ding, et al., "Chemical Trapping Experiments Support a Cation-Radical Mechanism for the Oxidative Polymerization of Aniline," Journal of Polymer Science, Part A: Polymer Chemistry, vol. 37: 2569-2579 (1999).
Dordick, J.S., "Enzymatic Catalysis in Monophasic Organic Dolvents," Enzyme Microb. Technol., 11(4):194-211 (1989).
Dordick, J.S., et al., "Polymerization of Phenols Catalyzed by Peroxidase in Nonaqueous Media," Biotechnology and Bioengineering, 30(1):31-36 (1987).

English Abstract of Kovalev, G. I., et al., "Study of the Effectiveness of Inhibitors in Oxidation of Jet Fuel in a Closed Volume," Deposited Doc., VINITI: 443-82 (1981).
English Abstract of Kovalev, G.I., et al., "Effectiveness of Inhibitors in the Oxidation of Jet Fuel With an Initiator," J. Neftekhimiya (Petroleum Chemistry), 21(2): 287-298 (1981).
Faber, K., "Biotransformations in Organic Chemistry," A Textbook, Fourth Completely Revised and Extended Edition, Springer-Verlag pp. 347-349 (1953).
FS&T 821 "Antioxidant," [online], [retrieved on Oct. 29, 2002]. Retrieved from the Internet <URL: http://class.fst.ohio-state.edu/fst821/>.
FS&T 821 "Food Lipids," [online], Oct. 2001 [retrieved on Oct. 29, 2002]. Retrieved from the Internet <URL: http://class.fst.ohio-state.edu/fst821/>.
FST 821 "Course Schedule," [online], [retrieved on Oct. 29, 2002]. Retrieved from the Internet <URL: http://class.fst.ohio-state.edu/fst821/>.
Hatayama, K., et al., "Anti-ulcer Effect of Isoprenyl Flavonoids. III.[1)] Synthesis and Anti-ulcer Activity of Metabolites of 2'-Carboxymethoxly-4,4'-bis(3-methyl-2-butenyloxy)chalcone[2)]," Chemical & Pharmaceutical Bulletin, 33(4), 1327-1333(Apr. 1985).
3805. 1006-001 (Jan. 26, 2009).
Heidekum, A., et al., "Nafion/Silica Composite Material Reveals High Catalytic Potential in Acylation Reactions," J. Catal. 188:230-232 (1999).
Hidalgo, M.E., et al., "Antioxidant Activity of Depsides and Depsidones," Phytochemistry, 37(6):1585-1587 (1994).
Hofer, K., et al., "[[(Anilinooxalyl)amino]phenyl] Phosphite Stabilizers for Polypropylene," Chemical Abstracts Service, ZCAPLUS, document No. 77:62780 (1972).
http://www.machinerylubrication.com/Read/1028/Oxidation-Lubricant, "Oxidation—The Lubricant's Nemesis," (Mar. 29, 2010, pp. 1-7).
Ikeda, R., et al., "Novel Synthetic Pathway to a Poly(phenylene oxide). Laccase-Catalyzed Oxidative Polymerization of Syringic Acid,"Macromolecules, 29:3053-3054 (1996).
Irgafos® 126, BASF publication, pp. 1-3, Jul. 2010.
Ismail, M.N. and Wazzan, A.A., "Evaluation of New Thermal Stabilizers and Antifatigue Agents for Rubber Vulcanizates," Polymer-Plastics Tech. and Eng., 45:751-758 (2006).
Jayaprakasha, G.K., et al., "Antioxidant Activity of Grape Seed (Vitis vinifera) Extracts on Peroxidation Models In Vitro," Food Chemistry, 73:285-290 (2001).
Jialanella, G.and Pilrma, I., "Synthesis of Poly(vinyl alcohol-co-vinyl gallate) by the Chemical Modification of Poly(vinyl alcohol)," Polymer Bulletin 18:385-389 (1987).
Joossens, J., et al., "Diphenyl Phosphonate Inhibitors for the Urokinase-Type Plasminogen Activator: Optimization of the P4 Position," J. Med. Chem., 49:5785-5793 (2006).
Kamitori, Y., et al., "Silica Gel as an Effective Catalyst for the Alkylation of Phenols and Some Heterocylic Aromatic Compounds," J. Org. Chem. 49: 4161-4165 (1984).
Kazandjian, R.Z., et al., "Enzymatic Analyses in Organic Solvents," Biotechnology and Bioengineering, XXVIII:417-421 (1986).
Khan, K.M., et al., "An Expedient Esterification of Aromatic Carboxylic Acids Using Sodium Bromate and Sodium Hydrogen Sulfite," Tetrahedron 59(29):5549-5554 (2003).
Kim, T. H., et al., "Melt Free-Radical Grafting of Hindered Phenol Antioxidant onto Polyethylene," J. Applied Polymer Science, 77:2968-2973 (2000).
Klibanov, A.M., et al., "Enzymatic Removal of Toxic Phenols and Anilines from Waste Waters," J. of Applied Biochemistry, 2(5):414-421 (1980).
Knobloch G: "Ein Neuer Weg Zu Polymergebudenen Alterungsschutzmitteln Technologisch Einfach Und Effektiv A New Way to Polymer Bound Antioxidants Technologically Simple and Efficient," Kautschuk Und Gummi, Kutststoffe, Huthig, Verlag, Heidelberg, DE, vol. 52, No. 1, Jan. 1, 1999, pp. 10-14.
Koshchii, V.A., et al. "Alkylation of Phenol by Alcohols in the Presence of Alumium Phenolate," Org. Chem. 24(7):1358-1361 (1988).

(56) References Cited

OTHER PUBLICATIONS

Lalancette, J.M., et al.,, "Metals Intercalated in Graphite. II. The Friedel-Crafts Reactions with ALCL₃-Graphite," *Can. J. Chem.* 52:589-591 (1974).

Li, X-G, et al., "Novel Multifunctional Polymers from Aromatic Diamines by Oxidative Polymerizations," Chemical Reviews, vol. 102(9): pp. 2925-2943 (2002).

Maki, M., et al., "Weather-Resistant Colored Polypropylene," Chemical Abstracts Service, ZCAPLUS, document No. 89:111364 (1978).

March, J., Advanced Organic Chemistry, McGraw Hill Book Company, New York, pp. 251-259 (1977).

Masada, H. and Oishi, Y., "A New Synthesis of aryl t-butyl Ethers," *Chem. Letters*, 57-58 (1978).

Masada, H. et al., "A New Heterogeneous Williamson Synthesis of Ethers Using t-alkyl Substrates," The *Chemical Society of Japan* 3:275-282 (1996).

Masada, H., et al., "A New Method for the Williamson Ether Synthesis Using t-alkyl Halides in Nonpolar Solvents," The *Chemical Society of Japan*, 2:164-166 (1995).

Mehdipour-Ataei, S., et al., "Novel Diols Containing Ester and Amide Groups and Resulting Poly(ester amide ester)s," *J. Applied Polymer Sci.*, 93:2699-2703 (2004), XP002420014.

Mejias, L., et al. "New Polymers From Natural Phenols Using Horseradish or Soybean Peroxidase," *Macromol. Biosci.*, 2:24-32 (2002).

Ol'dekop, Yu. A., et al. "Simple Synthesis of the tert-butyl Ether of Phenol" Inst. Fiz-Org. Khim., Minsk, USSR. *Zhurnal Obshchei Khimii*, 50(2):475-6 (1980).

Overgaag, M., et al., "Rearrangement of Alkyl Phenyl Ethers Over Dealuminated HY Zeolites Under Liquid-Phase Conditions," *Applied Catalysis A: General, Elsevier Sci.*, 175(1-2):139-146 (1998).

Pätoprstý, V., et al., "¹³C NMR Study of 3,9-Di(alkylphenoxy)-2,4,8,10-tetraoxa-3,9-diphosphaspiro[5.5]undecanes," *Magnetic Resonance in Chem*, 23(2):122-126 (1985).

PCT Application No. PCT/US2014/066935, filed Nov. 21, 2014, entitled "Macromolecular Antioxidants Based on Dual Type Moiety Per Molecule: Structures Methods of Making and Using the Same," Invitation to Pay Additional Fees and Where Applicable, Protest Fee of the International Searching Authority dated Feb. 3, 2015.

PCT Application No. PCT/US2014/066935, Notification Concerning Transmittal of International Preliminary Report on Patentability dated Jun. 2, 2016 entitled "Macromolecular Antioxidants Based on Dual Type Moiety Per Molecule: Structures, Methods of Making and Using the Same."

Pirozhenko, V.V., et al., "NMR Study of Topomerization of N-Aroyl-p-Benzoquinonemonoimines," *Russian J. of Organic Chem.*, 31(11):1514-1519 (1995).

Quaschning, V., et al., "Properties of Modified Zirconia Used as Friedel-Crafts-Acylation Catalysts," *J. Catal.* 177:164-174 (1998). RN 85650-63-1, Nov. 16, 1984.

Ryu, K., et al., "Peroxidase-Catalyzed Polymerization of Phenols," Biocatalysis in Agricultural Biotechnology, Chapter 10:141-157 (1988).

Sakthivel, A., et al., "Vapour Phase Tertiary Butylation of Phenol Over Sulfated Zirconia Catalyst," *Catal. Lett.*, 72(3-4):225-228 (2001).

Sartori G., et al., "Highly Selective Mono-tert-butylation of Aromatic Compounds," *Chem. Ind.*, (London), (22):762-763 (1985).

Scharpe, S.L., et al., "Serine Peptidase Modulators, Their Preparation, and Their Therapeutic Use," Chemical Abstracts Service, ZCAPLUS, document No. 131:223514 (1999).

Singh, A. and Kaplan, D. L., "Biocatalytic Route to Ascorbic Acid-Modified Polymers for Free-Radical Scavenging," *Adv. Matter.*, 15(15):1291-1294 (2003).

Spano, R., et al., "Substituted Anilides of 3-Monoethyl Ester of 4 Hydroxyisophthalic Acid," *J. of Med Chem.*, 15(5):552-553 (1972).

Thompson, C. Ray, "Stability of Carotene in Alfalfa Meal: Effect of Antioxidants," *Industrial & Engineering Chemistry*, 24(5): 922-925 (1950).

Tsvetkov, O.N., et al., "Alkylation of Phenols with Higher Olefins. Part I," *Int. Chem. Eng.* 7(1):104-121 (1967).

XP-002419239, "Discover Our World of Effects for Polyolefins," *Ciba Speciality Chemicals*, (2003).

Parmar, V.S., et al., "Hydrolytic Reactions on Polyphenolic Perpropanoates by Porcine Pancreatic Lipase Immobilized in Microemulsion-based Gels," Bioorganic & Medicinal Chemistry Letters, 6(19): 2269-2274 (1996).

Database CA [online] Chemical Abstracts Service, Columbus, Ohio, US, May 30, 2018, Takaoka, Kyo et al. "Synthesis of some methyl 10, 11-diarylundecanoates and methyl 11-aryl-9-undecenoates and their activity as antioxidants and corrosion inhibitors," XP002781515, retrieved from STN Database accession No. 1968:466867 (abstract); Yukagaku, 17(7): 387-91 (1968).

Zinke, Ott, and Garrana, "Zur Kenntnis des Hartungsprozesses von Phenol-Formaldehyd-Harzen," Afh. Chem., Bd. 89, pp. 135-142 (1958).

Kamalakar, K. et al., "Influence of structural modification on lubricant properties of sal fat-based lubricant base stocks," Industrial Crops and Products, 76: 456-466 (2015).

Kammerer, Hermann et al., "Der aufbau einiger homologer Reihen von Hydroxyphenylenmethylen-Verbindungen und ihr Schmelzverhalten," Die Afakromolekulare Chemie, 169: 1-13 (1973).

Orlando, M. et al., "Elimination of Acetic Acid from Protonated 4,5-Diacetoxyphenanthrene and 2,2'-Diacetoxybiphenyl: an Example of an Ion Chemistry Proximity Effect," Organic Mass Spectrometry, 28(10): 1184-1188 (1993).

Smith, M.E.B. et al., "Development of chemical probes: Toward the mode of action of a methylene-linked di(aryl acetate) EI," Bioorganic & Medicinal Chemistry, 18(14): 4917-4927 (2010).

International Search Report and Written Opinion for Int'l Application No. PCT/US2014/066935, titled: Macromolecular Antioxidants Based on Dual Type Moiety Per Molecule: Structures Methods of Making and Using the Same, dated Sep. 17, 2015.

\* cited by examiner

MACROMOLECULAR ANTIOXIDANTS BASED ON DUAL TYPE MOIETY PER MOLECULE: STRUCTURES, METHODS OF MAKING AND USING THE SAME

RELATED APPLICATION(S)

This application is a divisional of U.S. application Ser. No. 15/038,361 filed May 20, 2016, which is a U.S. National Stage of International Application No. PCT/US2014/066935, filed Nov. 21, 2014, which designates the U.S., published in English, and claims the benefit of U.S. Provisional Application No. 61/907,863, filed on Nov. 22, 2013. The entire teachings of the above applications are incorporated herein by reference.

GOVERNMENT SUPPORT

This invention was made with government support under IIP-1138520 from the National Science Foundation. The government has certain rights in the invention.

BACKGROUND OF THE INVENTION

Antioxidants are employed to prevent oxidation in a wide range of materials, for example, plastics, elastomers, lubricants, bio- and petroleum-based products (lubricants, gasoline, aviation fuels, and engine oils), cooking oil, cosmetics, processed food products, and the like. While many small molecule antioxidants exist, there is a continuing need for new antioxidants that have improved properties and thermal stability to function at high operating temperatures in a wide range of applications.

SUMMARY OF THE INVENTION

The present invention relates to compounds containing dual functionalities of aromatic amines and hindered phenols that can be useful as stabilizers for organic materials, lubricants and petroleum based products, plastics and elastomers, cosmetics, foods and cooking oils, and other materials. In particular, the present invention pertains to highly effective antioxidant macromolecules described herein. This invention also reports an improved, highly efficient and economical process for the synthesis of amine (nitrogen) and sterically hindered phenol containing dual functional macromolecules. The design of macromolecules in this invention can incorporate at least two antioxidant moieties having different reactivities. The present invention also discloses their superior antioxidant performance compared to presently used commercial antioxidants. This is demonstrated especially in biobased lubricants and oils. In general one unique feature and design of the antioxidants described herein is their improved compatibility and performance in many oils and fuels including bio-, petroleum- and synthetic oils and fuels such gasoline, diesel, and biodiesel compared with currently available antioxidants.

The present invention pertains to a compound represented by structural formula I:

Structural Formula I

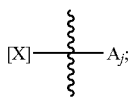

wherein when j is 2, X is:

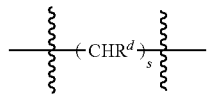

wherein $R^d$ is —H or OH or an optionally substituted C1-C10 linear or branched alkyl chain;
s is an integer from 1-10; and
wherein when j is 3, X is

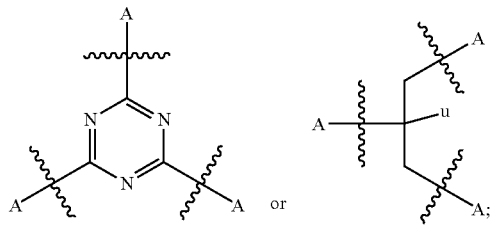

and
wherein u is H or —CH$_2$CH$_3$, or C1-C10 linear or branched alkyl chain.
wherein A, for each occurrence independently, is selected from:

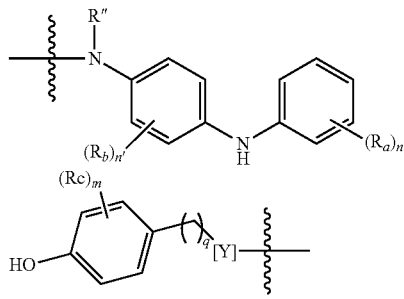

$R^d$, independently for each occurrence, is —H, —OH, an optionally substituted C1-C10 linear or branched alkyl chain, e.g., a tertiary butyl group.
[Y] is —(C=O)—, —(C=O)O—, —O(C=O)—, —O—, —S—, —NH—, —N(R)—
$R_c$, independently for each occurrence, is H, a alkyl group substituent bonded to a ring carbon atom adjacent (ortho) to a ring carbon atom substituted with an —OH group. Each $R_c$ is H, independently an optionally substituted C1-C20 alkyl group, an optionally substituted C1-C10 alkyl group, a tertiary carbon group, an optionally substituted aryl group, and optionally substituted alkoxy group, an optionally substituted carbonyl group, an optionally substituted alkoxycarbonyl group, an optionally substituted aryloxycarbonyl group, —OH, —SH or —NH$_2$ or an optionally substituted carbocyclic or heterocyclic non-aromatic ring.
m is an integer from 0 to 2.
q is an integer from 0 to 10
R", independently for each occurrence, is H, an optionally substituted C1-C20 alkyl group, an optionally substituted C1-C10 alkyl group, an optionally substituted aryl group, and optionally substituted alkoxy group, an optionally substituted carbonyl group, an optionally substituted alkoxycarbonyl group, an optionally substituted aryloxycarbonyl group, —OH, —SH or —NH$_2$ or an optionally substituted carbocyclic or heterocyclic non-aromatic ring.

$R_a$, independently for each occurrence, is H, independently an optionally substituted C1-C20 alkyl group, an optionally substituted C1-C10 alkyl group, an optionally substituted aryl group, and optionally substituted alkoxy group, an optionally substituted carbonyl group, an optionally substituted alkoxycarbonyl group, an optionally substituted aryloxycarbonyl group, —OH, —SH or —NH$_2$ or an optionally substituted carbocyclic or heterocyclic non-aromatic ring.

n is an integer from 0 to 5.

Each $R_b$, is H, independently an optionally substituted C1-C20 alkyl group, an optionally substituted C1-C10 alkyl group, an optionally substituted aryl group, and optionally substituted alkoxy group, an optionally substituted carbonyl group, an optionally substituted alkoxycarbonyl group, an optionally substituted aryloxycarbonyl group, —OH, —SH or —NH$_2$ or an optionally substituted carbocyclic or heterocyclic non-aromatic ring.

n' is an integer from 0 to 4.

In another embodiment, the present invention addresses relates to a compound represented by structural formula II:

Structural Formula II

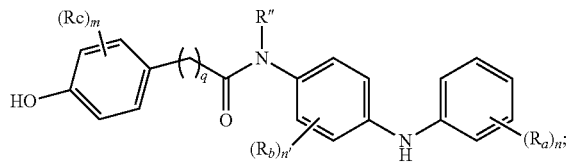

wherein q is an integer from 0 to 10; in some instances, q is 0, in some instances, q is 2; in some instances, q is 4;

$R_c$ is a bulky alkyl group substituent bonded to a ring carbon atom adjacent (ortho) to a ring carbon atom substituted with an —OH group. Each $R_c$ is H, independently an optionally substituted C1-C10 alkyl group, a tertiary carbon group, an optionally substituted aryl group, and optionally substituted alkoxy group, an optionally substituted carbonyl group, an optionally substituted alkoxycarbonyl group, an optionally substituted aryloxycarbonyl group, —OH, —SH or —NH$_2$ or an optionally substituted carbocyclic or heterocyclic non-aromatic ring.

m is an integer from 0 to 2.

R" is H, independently an optionally substituted C1-C10 alkyl group, an optionally substituted aryl group, and optionally substituted alkoxy group, an optionally substituted carbonyl group, an optionally substituted alkoxycarbonyl group, an optionally substituted aryloxycarbonyl group, —OH, —SH or —NH$_2$ or an optionally substituted carbocyclic or heterocyclic non-aromatic ring.

Each $R_a$, is H, independently an optionally substituted C1-C10 alkyl group, an optionally substituted aryl group, and optionally substituted alkoxy group, an optionally substituted carbonyl group, an optionally substituted alkoxycarbonyl group, an optionally substituted aryloxycarbonyl group, —OH, —SH or —NH$_2$ or an optionally substituted carbocyclic or heterocyclic non-aromatic ring.

n is an integer from 0 to 5.

Each $R_b$, is H, independently an optionally substituted C1-C10 alkyl group, an optionally substituted aryl group, and optionally substituted alkoxy group, an optionally substituted carbonyl group, an optionally substituted alkoxycarbonyl group, an optionally substituted aryloxycarbonyl group, —OH, —SH or —NH$_2$ or an optionally substituted carbocyclic or heterocyclic non-aromatic ring.

n' is an integer from 0 to 4.

In another embodiment, the present invention is a compound represented by structural formula III:

Structural Formula III

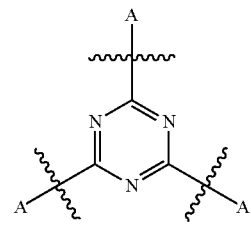

wherein each A is independently

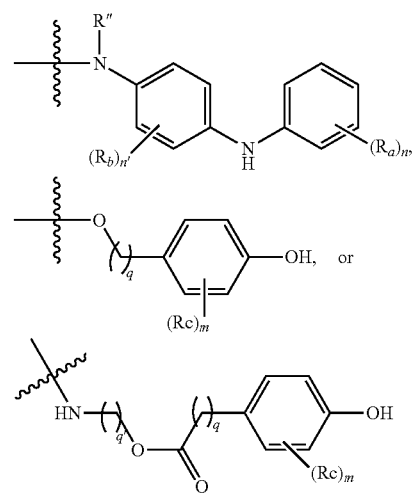

q' is an integer between 0 and 10; in some instances, q' is 2; in some instances, q' is 3; in some instances, q' is 4; in some instances, q is 2; in some instances, q is 3; in some instances, q is 4; and the remaining variables are as described in the immediately preceding paragraph or for structural formula (I).

In yet another embodiment, the present invention is a compound represented by structural formula IV:

Structural Formula IV

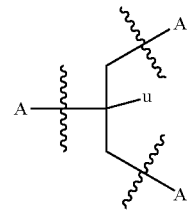

wherein each A is independently

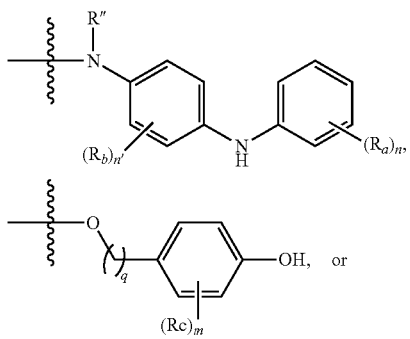

-OH, or

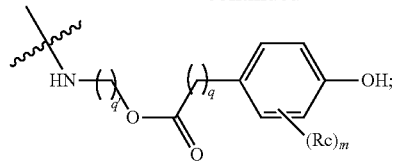

q' is an integer between 0 and 10; in some instances, q' is 2; in some instances, q' is 3; in some instances, q' is 4; in some instances, q is 2; in some instances, q is 3; in some instances, q is 4; and the remaining variables are as described in the immediately preceding paragraph or for structural formula (I).

In another embodiment, the present invention is a compound represented by structural formula V:

Structural Formulas V

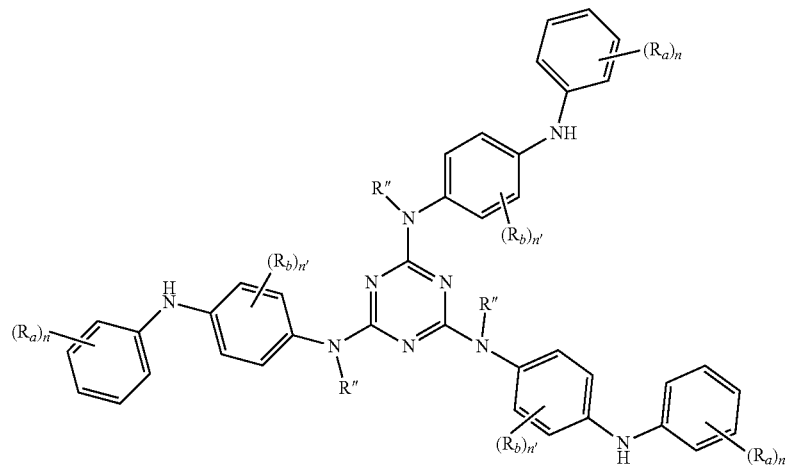

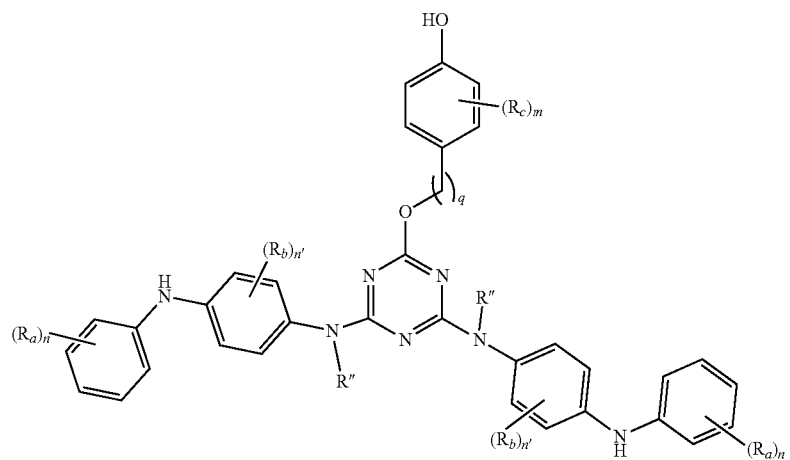

-continued
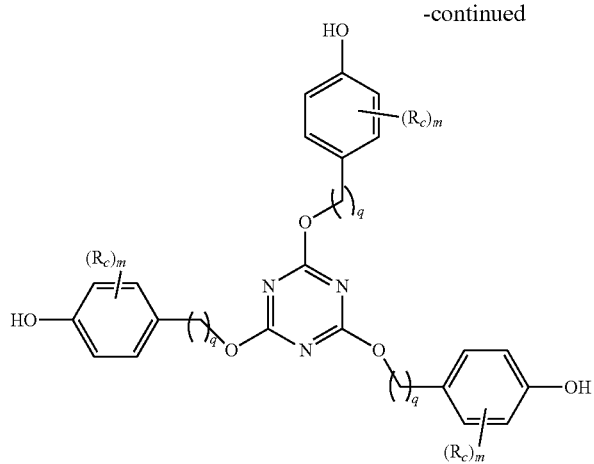
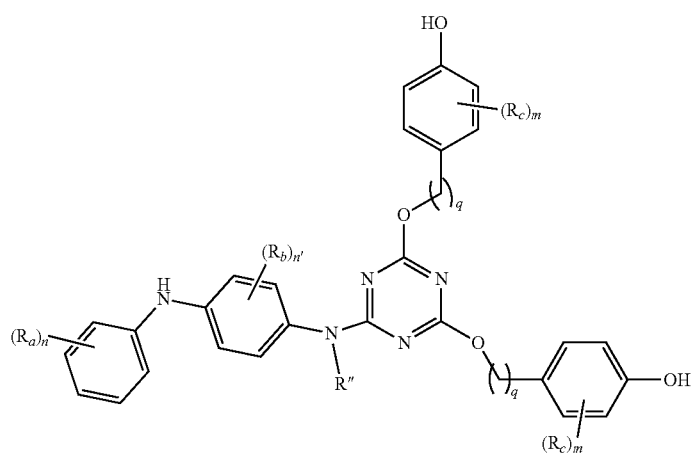
wherein in the variables are as described in the immediately preceding paragraph or structural formula (I). Each q independently is 2. Each q independently is 3. Each q independently is 4.
In another embodiment, the present invention is a compound represented by structural formulas VI:
Structural Formulas VI
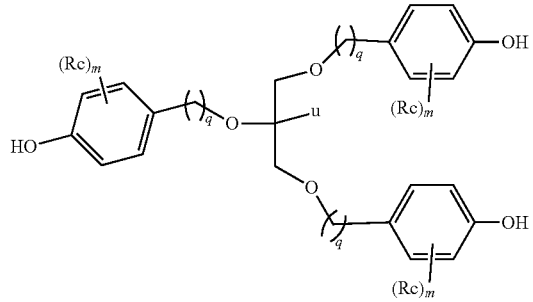
-continued
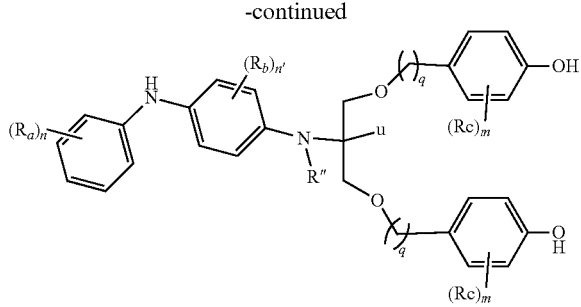
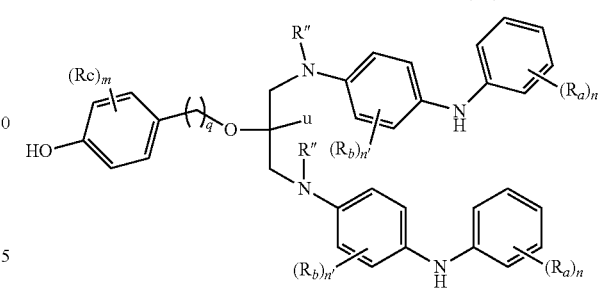

-continued

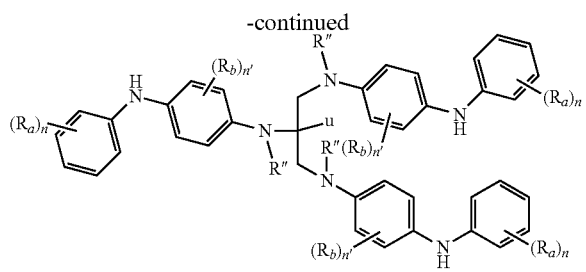

Where in the variables are as described in the immediately preceding paragraph or structural formula (I). Each q independently is 2. Each q independently is 3. Each q independently is 4.

In another embodiment, the present invention is a method of producing a compound represented by structural formula (I). The method comprises combining a linker, an amine and a phenol derivative in the presence of catalyst, wherein the phenol derivative comprises at least one unsubstituted ring-carbon atom. In yet another embodiment, the present invention is a method of producing a compound represented structural formula (I). The method comprises combining a phenolic-carbonyl derivative represented by the following structural formula:

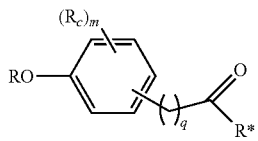

Wherein $R_c$ is a bulky alkyl group substituent bonded to a ring carbon atom adjacent (ortho) to a ring carbon atom substituted with an —OH group. R is H, independently an optionally substituted C1-C10 alkyl group, a tertiary carbon group, an optionally substituted aryl group, and optionally substituted alkoxy group, an optionally substituted carbonyl group, an optionally substituted alkoxycarbonyl group, an optionally substituted aryloxycarbonyl group, an optionally substituted carbocyclic or heterocyclic non-aromatic ring. m is an integer from 0 to 2. R* independently is H, NH, $NH_2$, Cl, or an optionally substituted aryloxycarbonyl group, —OH, —SH or —$NH_2$ or an optionally substituted carbocyclic or heterocyclic non-aromatic ring. q is 0 to 10.

In another embodiment the present invention is a method of preventing oxidation in an oxidizable material, comprising combining the oxidizable material with a compound of the present invention.

The antioxidants described herein which are prepared by the disclosed processes in general are superior antioxidants (compared to currently available antioxidants) against oxidative, thermal degradation of organic materials. These macromolecular antioxidants generally have comparatively higher antioxidant activities along with improved thermal stability and performance in a wide range of materials including but not limited to plastics; elastomers; thermoplastic elastomers; lubricants; petroleum, bio- and synthetic oil based products (lubricants, gasoline, aviation fuels, and engine oils, biolubricants; metal working fluids, hydraulic fluids, drilling fluids, marine lubricants, environmentally acceptable lubricants (EALs), grease, and bio- and synthetic-oil based grease); cooking oil; cosmetics; processed food products.

The processes of the present invention have many advantages which can allow improved synthesis of these macromolecular antioxidants. For example, the disclosed processes can be economically carried out in the melt phase without the presence of catalysts. Moreover, the processes described herein generally reduce or eliminate purification steps for the final product compared to existing syntheses, which can lead to a superior performance/cost ratio for the product and reduced amounts of waste.

DETAILED DESCRIPTION OF THE INVENTION

A description of preferred embodiments of the invention follows.

As used herein, "dual functional" means any molecule with two functional groups which can optionally be the same or in certain embodiment are different, such as amine and hydroxy.

As used herein "adduct" means chemically linked.

Sterically hindered, as used herein means that the substituent group (e.g., bulky alkyl group) on a ring carbon atom adjacent (or para) to a ring carbon atom substituted with a phenolic hydroxy group (or thiol or amine group), is large enough to sterically hinder the phenolic hydroxy group (or thiol or amine groups). This steric hindrance, in certain embodiments results in more labile or weak bonding between the oxygen and the hydrogen (or sulfur or nitrogen and hydrogen) and in turn enhances the stability and antioxidant activity (proton donating activity) of the sterically hindered antioxidant.

Repeat units of the antioxidants of the invention include substituted benzene molecules. Some of these benzene molecules are typically based on phenol or a phenol derivative, such that they have at least one hydroxyl or ether functional group. In certain embodiments, the benzene molecules have a hydroxyl group. The hydroxyl group can be a free hydroxyl group and can be protected or have a cleavable group attached to it (e.g., an ester group). Such cleavable groups can be released under certain conditions (e.g., changes in pH), with a desired shelf life or with a time-controlled release (e.g., measured by the half-life), which allows one to control where and/or when an antioxidant can exert its antioxidant effect. The repeat units can also include analogous thiophenol and aniline derivatives, e.g., where the phenol —OH can be replaced by —SH, —NH—, and the like.

Substituted benzene repeat units of an antioxidant of the invention are also typically substituted with a bulky alkyl group or an n-alkoxycarbonyl group. In certain embodiments, the benzene monomers are substituted with a bulky alkyl group. In certain other embodiments, the bulky alkyl group is located ortho or meta to a hydroxyl group on the benzene ring, typically ortho. A "bulky alkyl group" is defined herein as an alkyl group that is branched alpha- or beta- to the benzene ring. In certain other embodiments, the alkyl group is branched alpha to the benzene ring. In certain other embodiments, the alkyl group is branched twice alpha to the benzene ring, such as in a tert-butyl group. Other examples of bulky alkyl groups include isopropyl, 2-butyl, 3-pentyl, 1, 1-dimethylpropyl, 1-ethyl-1-methylpropyl and 1, 1-diethylpropyl. In certain other embodiments, the bulky alkyl groups are unsubstituted, but they can be substituted with a functional group that does not interfere with the antioxidant activity of the molecule. Straight chained alkoxycarbonyl groups include methoxycarbonyl, ethoxycarbonyl, n-propoxycarbonyl, n-butoxycarbonyl and n-pentoxycarbonyl. N-propoxycarbonyl is a preferred group. Similar to the bulky alkyl groups, n-alkoxycarbonyl groups are optionally substituted with a functional group that does not interfere with the antioxidant activity of the molecule.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

In one embodiment the present invention is a compound represented by structural formula (I) wherein the variables are as described as follows:

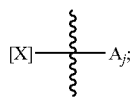

wherein when j is 2, X is:

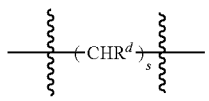

wherein $R^d$ is —H or OH or an optionally substituted C1-C10 linear or branched alkyl chain;
s is an integer from 1-10; and
wherein when j is 3, X is

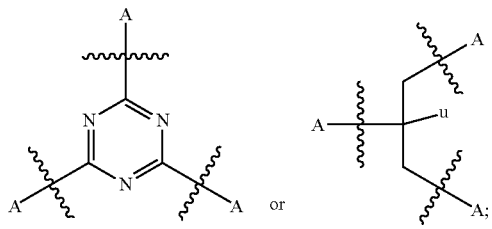

and
wherein u is H or —CH$_2$CH$_3$, or C1-C10 linear or branched alkyl chain.
wherein A, for each occurrence independently, is selected from:

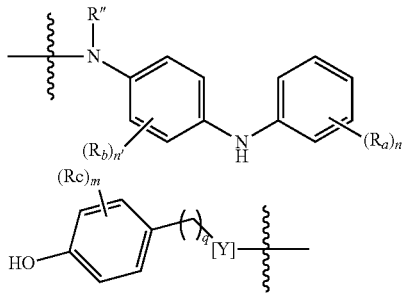

s is an integer from 0 to 10;
q is 0 to 10.

Each variable $R^d$ is independently —H, —OH, an optionally substituted C1-C10 linear or branched alkyl chain, e.g., a tertiary butyl group. u is H or —CH$_2$CH$_3$, or C1-C10 linear or branched alkyl chain.

[Y] is —(C=O)—, —(C=O)O—, —O(C=O)—, —O—, —S—, —NH—, —N(R)—

In one embodiment, each R'', $R_a$, and $R_b$ is H, independently an optionally substituted C1-C20 alkyl group, an optionally substituted C1-C10 alkyl group, an optionally substituted aryl group, an optionally substituted aralkyl, an optionally substituted alkoxy group, an optionally substituted carbonyl group, an optionally substituted alkoxycarbonyl group, an optionally substituted aryloxycarbonyl group, —OH, —SH or —NH$_2$ or an optionally substituted carbocyclic or heterocyclic non-aromatic ring. In another embodiment, each R'', $R_a$ and $R_b$ is independently an optionally substituted alkyl. In one embodiment, each R'', $R_a$, and $R_b$ is independently a C1-C20 alkyl. In another embodiment, each R'', $R_a$, and $R_b$ is independently a C1-C10 alkyl. In another embodiment, each R'', $R_a$ and $R_b$ is independently selected from the group consisting of:

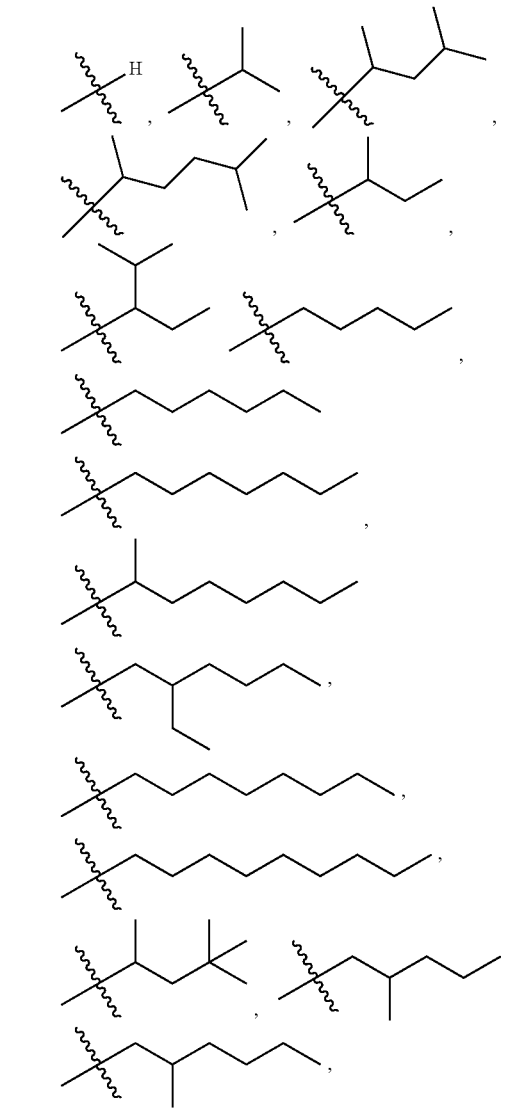

-continued

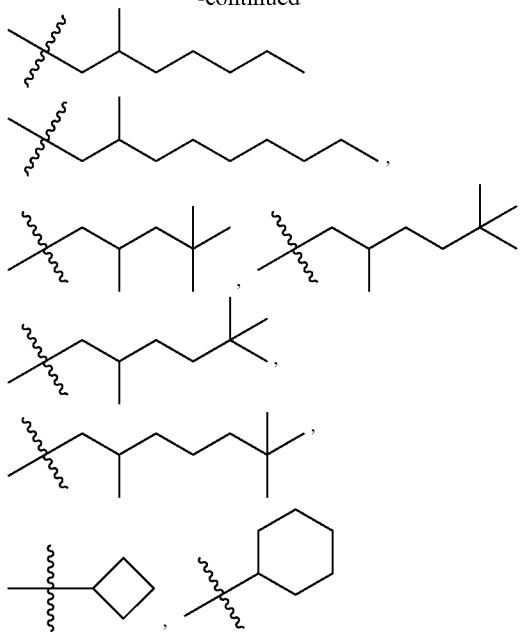

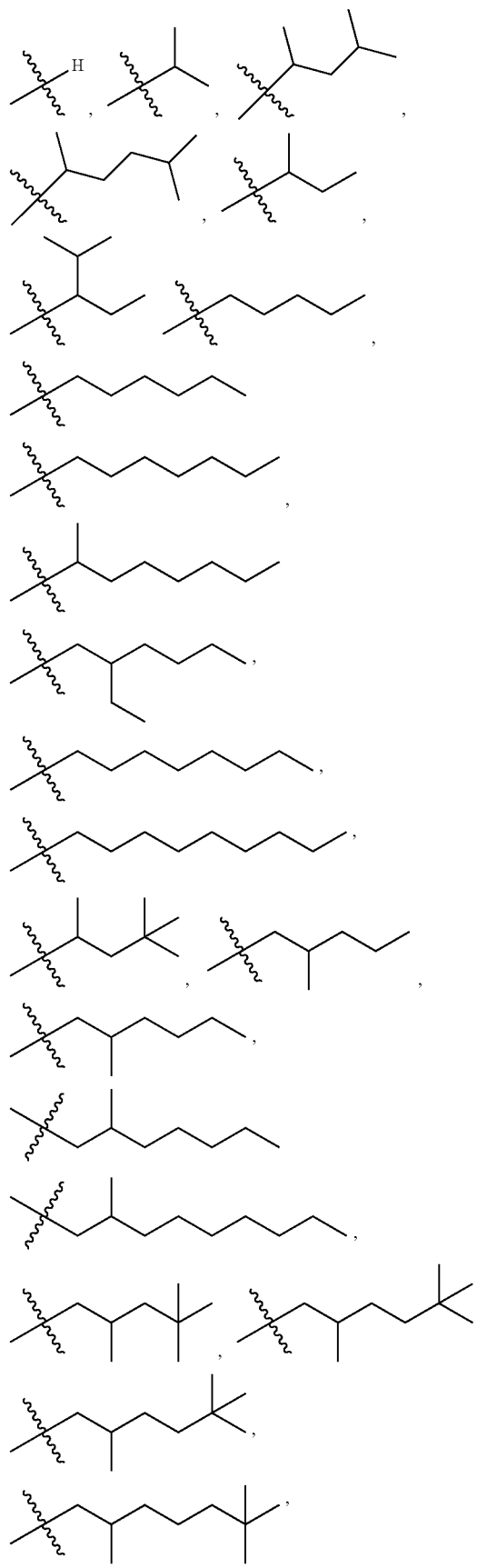

Each $R_b$ is independently an optionally substituted alkyl.

Each $R_c$ is independently an optionally substituted alkyl or an optionally substituted alkoxycarbonyl.

In another embodiment, each $R_c$ is independently a C1-C10 alkyl. Each $R_c$ is a bulky alkyl group substituent bonded to a ring carbon atom adjacent (ortho) to a ring carbon atom substituted with an —OH group. Each $R_c$ is H, independently an optionally substituted C1-C10 alkyl group, a tertiary carbon group, an optionally substituted aryl group, and optionally substituted alkoxy group, an optionally substituted carbonyl group, an optionally substituted alkoxycarbonyl group, an optionally substituted aryloxycarbonyl group, —OH, —SH or —NH$_2$ or an optionally substituted carbocyclic or heterocyclic non-aromatic ring. m is an integer from 0 to 2.

R" is —H, an optionally substituted alkyl, an optionally substituted aryl or an optionally substituted aralkyl. In one embodiment, R" is —H, a C1-C20 alkyl or an optionally substituted aralkyl. In another embodiment, R" is —H, a C1-C10 alkyl or a substituted benzyl group. In yet another embodiment, R" is —H. In yet another embodiment, R" is:

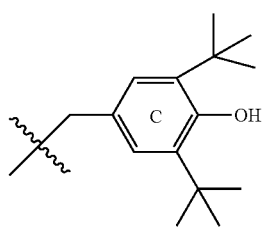

In yet another embodiment, q is an integer from 0 to 10. In one embodiment, q is an integer from 1 to 6. In another embodiment, q is 1. In yet another embodiment, q is 2. In yet another embodiment, q is 3. In yet another embodiment, q is 4.

In yet another embodiment R" is selected from the group consisting of:

-continued

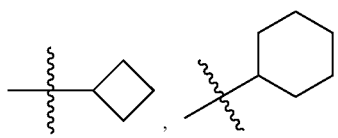 [SMILES: *C1CCC1 ; *C1CCCCC1]

In yet another embodiment, q is an integer from 0 to 10. In one embodiment, q is an integer from 1 to 6. In another embodiment, q is 1. In yet another embodiment, q is 2. In yet another embodiment, q is 3. In yet another embodiment, q is 4.

m is an integer from 0 to 2. In another embodiment m is 0. In one embodiment, m is 1 or 2. In another embodiment, m is 1. In another embodiment, m is 2.

n is an integer from 0 to 5. In one embodiment n is 0. In yet another embodiment n is 1. In another embodiment n is 4. In one embodiment n is 2. In another embodiment, n is 3 or 5.

n' is an integer from 0 to 4. In one embodiment, n' is 0; in another embodiment, n' is 1; in another embodiment, n' is 2; in another embodiment, n' is 3; in another embodiment, n' is 4.

In one embodiment of the present invention for the compounds represented by structural formula (II):

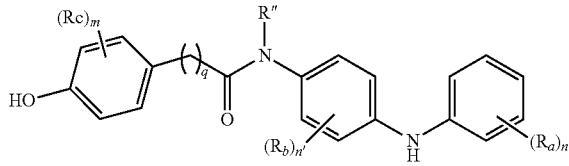

Structural Formula II

Each $R_a$ is independently a C1-C20 alkyl. Each $R_c$ is independently a C1-C10 alkyl. R" is —H, a C1-C20 alkyl or an optionally substituted aralkyl, and the remainder of the variables are as described above for structural formula (I).

In another embodiment, the compound of structural formula (II) is represented by structural formula (VII):

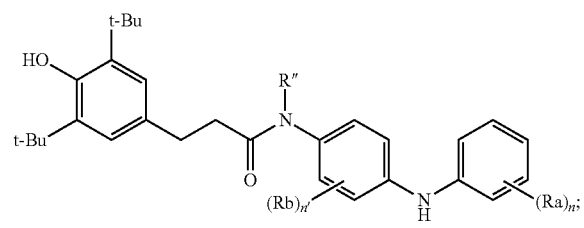

Structural Formula VII wherein the remainder of the variables is as described in the immediately preceding paragraph or for structural formula (I).

In another embodiment, the compound of structural formula (II) is represented by structural formula (VIII):

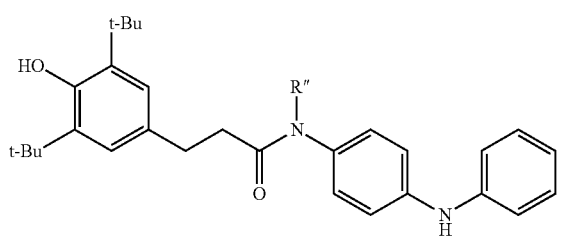

Structural Formula VIII wherein in R" is as defined for Structural Formula (I); in some instances, R" is H or a C10 alkyl.

In another embodiment, R" in structural formula (VIII) is selected from the group of consisting of

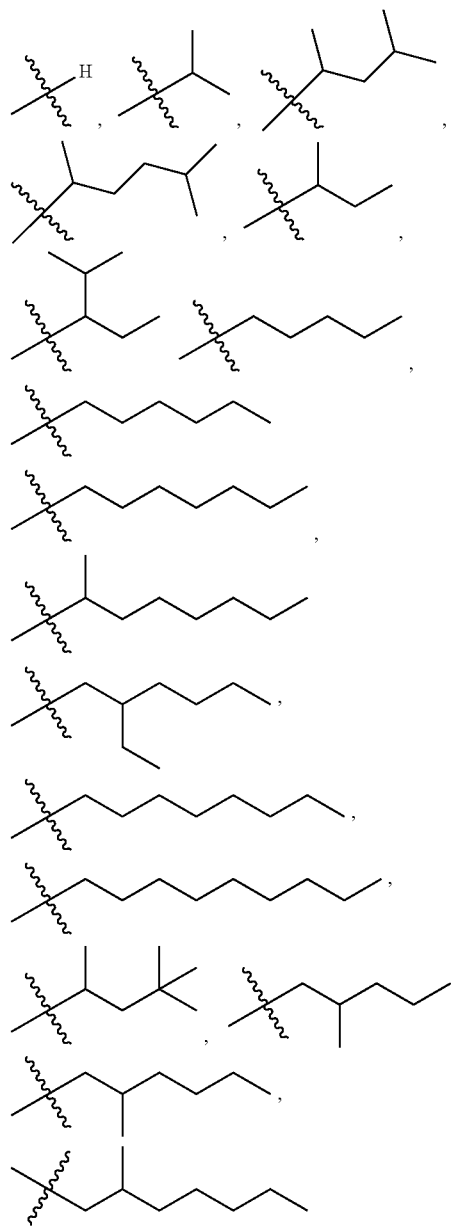

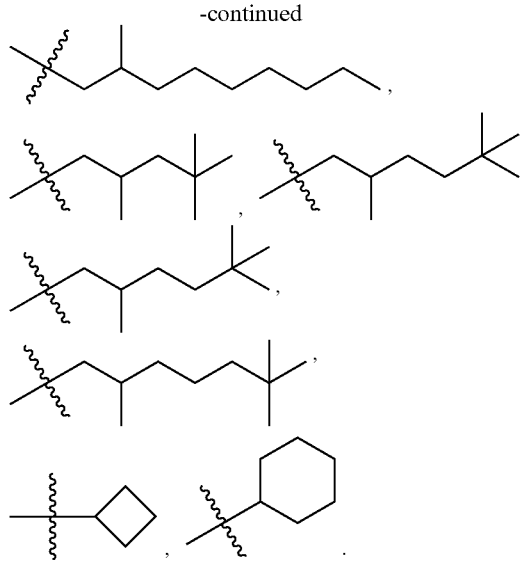

In certain embodiments, the invention is a composition that is a mixture of the compounds having Structures (VIII) with varying R". In one embodiment, the invention is a composition that is a mixture of the following two structures:

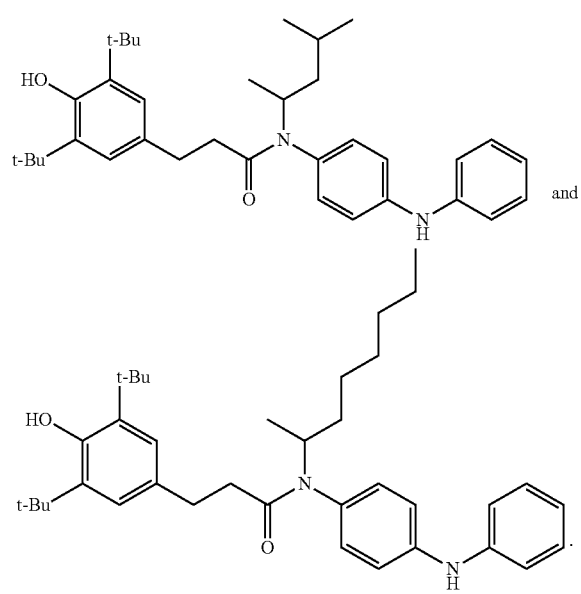

In certain embodiments of the present invention the compounds represented by structural formula (VIII) are represented by the following structural formulas:

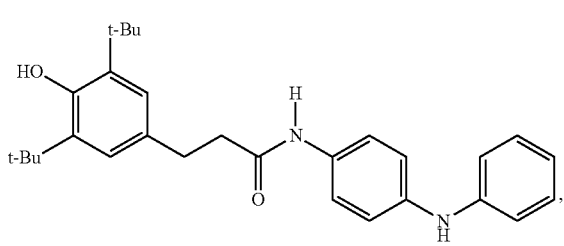

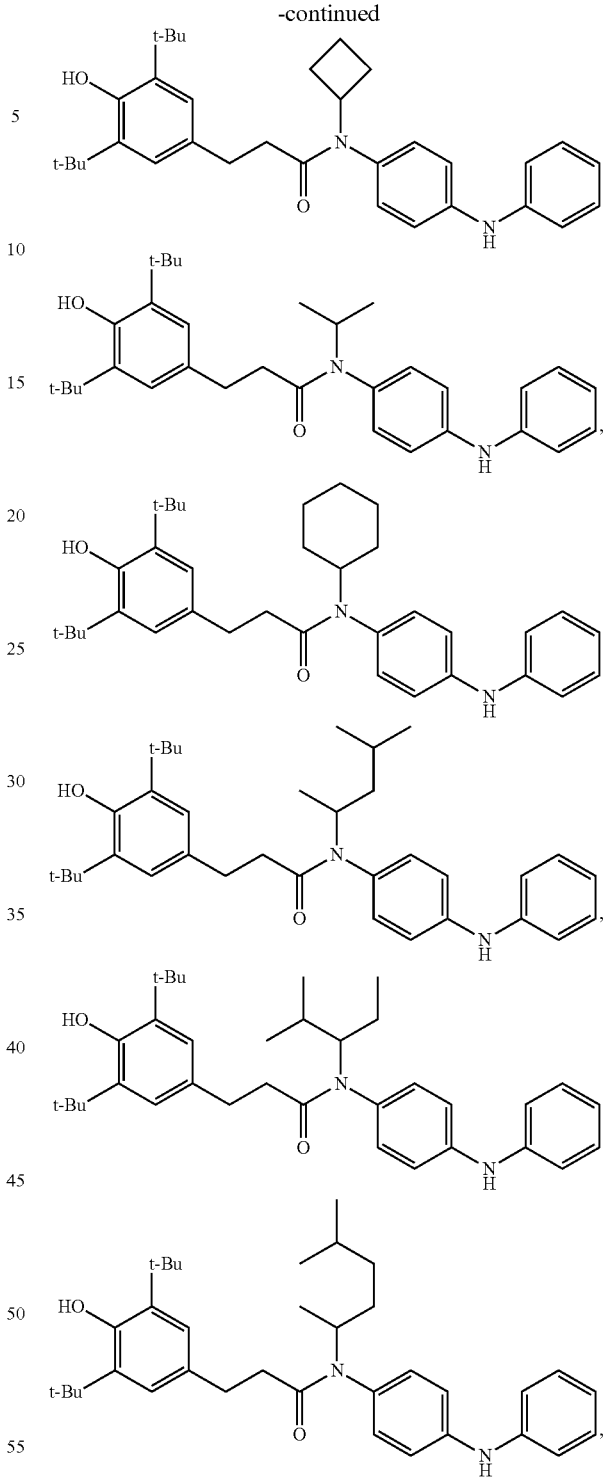

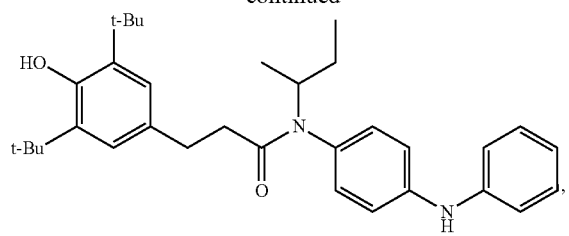
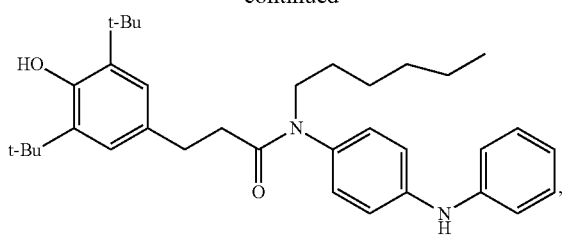
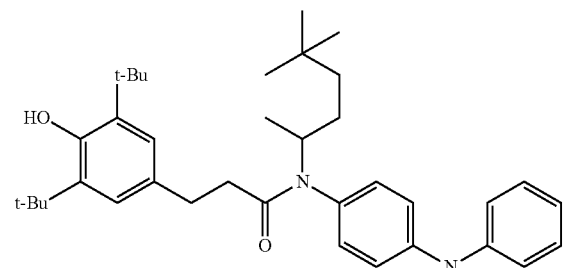
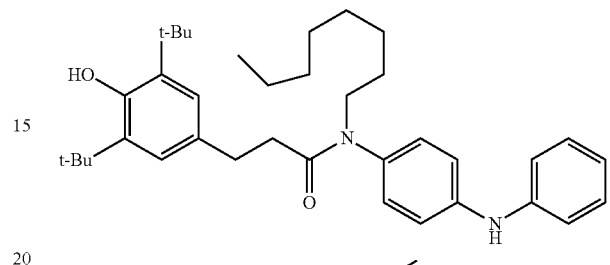
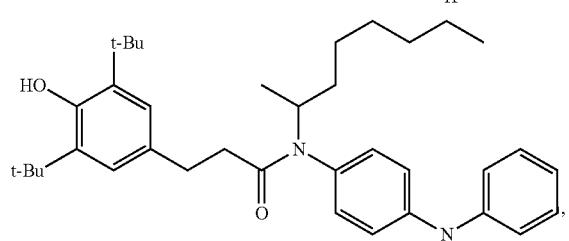
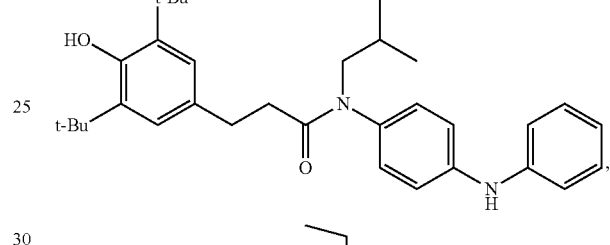
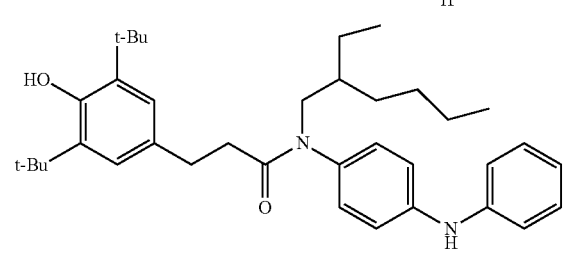
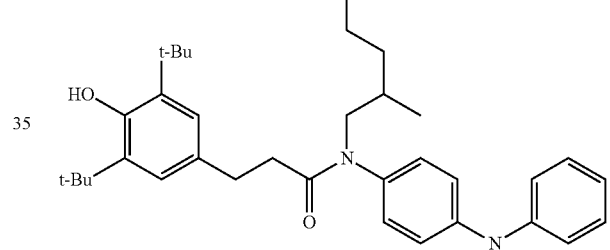
In yet other embodiments of the present invention the compounds represented by structural formula (VIII) are represented by the following structural formulas:
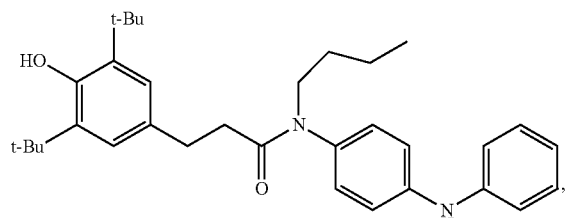
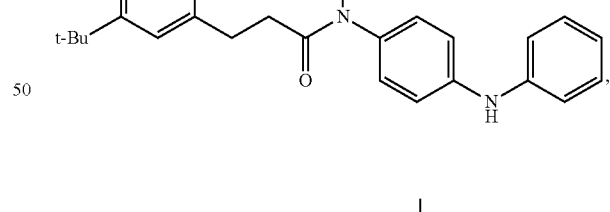
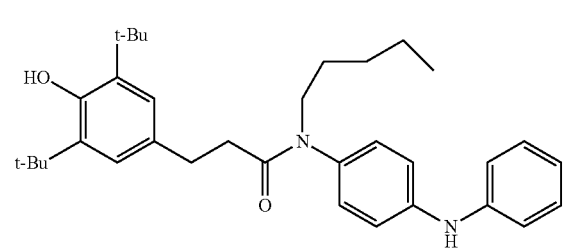
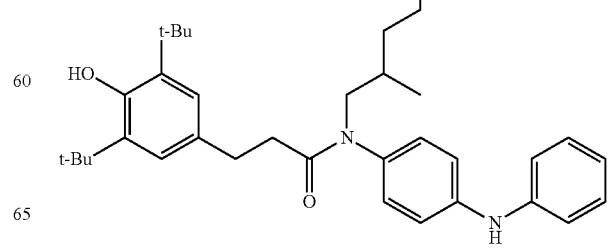

-continued
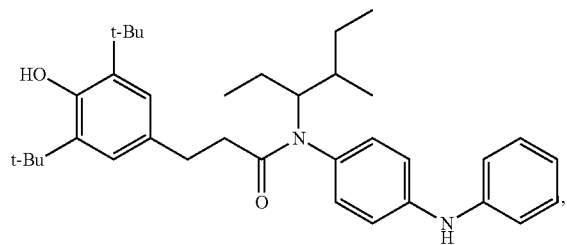
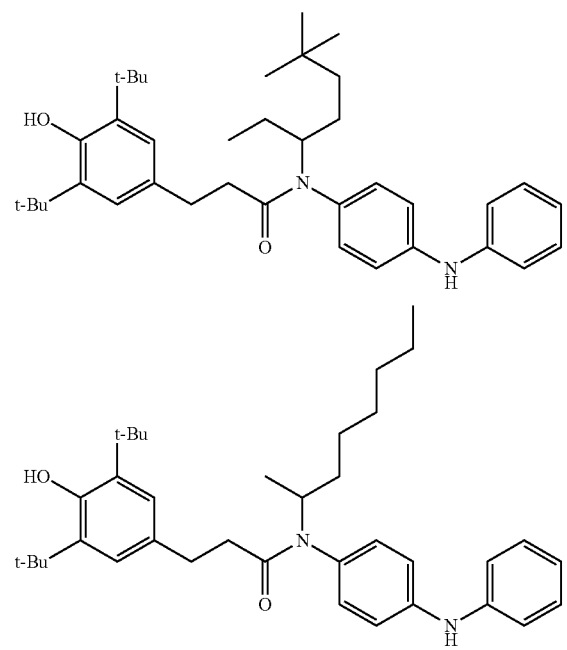
In another embodiment, the present invention is a compound or mixture of compounds represented by structural formula (VIII):
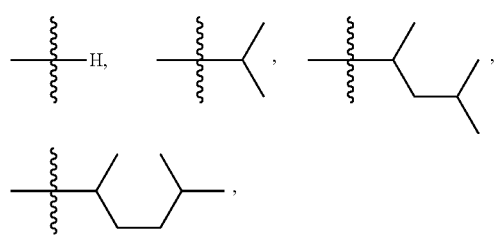
wherein R″ is
-continued
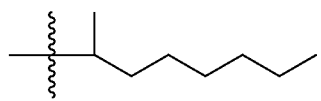
In yet other embodiments, the invention is a composition that is a mixture of compounds with the following structures (i), (ii), (iii), (iv) and (v):
(i)
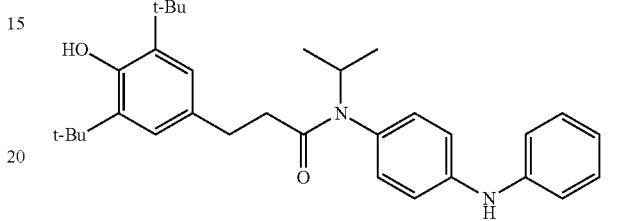
(ii)
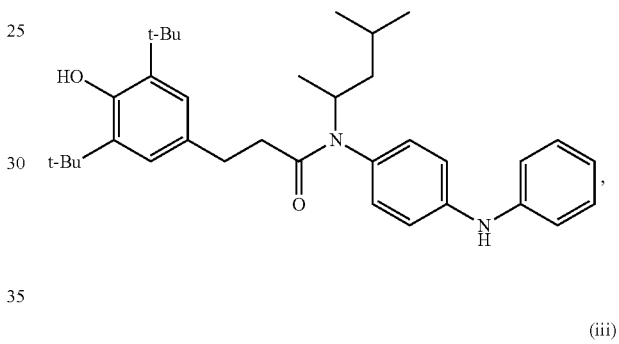
(iii)
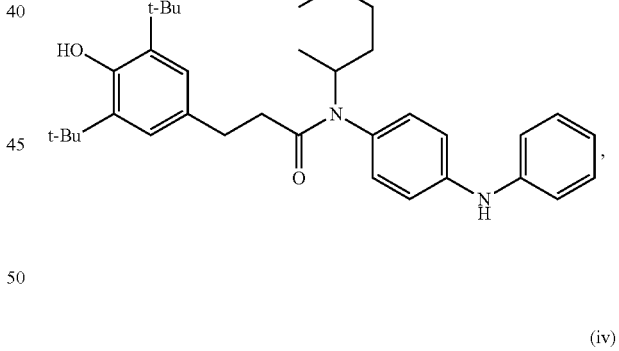
(iv)
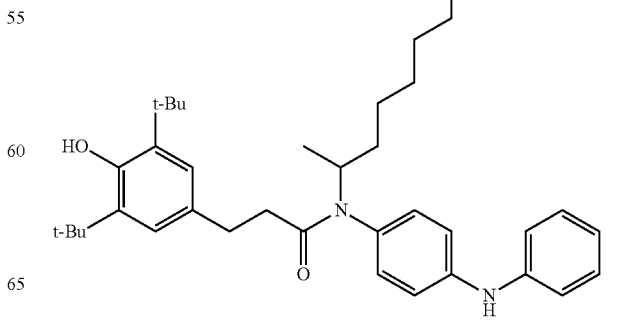

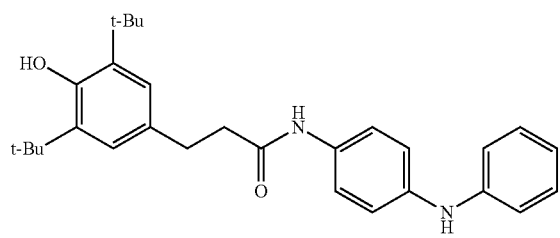 [SMILES: CC(C)(C)c1cc(CCC(=O)Nc2ccc(Nc3ccccc3)cc2)cc(C(C)(C)C)c1O]

(v)

In certain embodiments, the present invention is a composition that is a mixture of the compounds (i), (ii), (iii), (iv) in the following ratio: 1:1:1:1; 0:1:1:1; 1:0:1:1; 1:1:0:1 or 1:1:1:0.

In certain embodiments, the present invention is a composition that is a mixture of the compounds. The composition can include a mixture of two compounds, such as the mixture of the following compounds: (i):(ii), (i):(iii), (ii):(iii), (ii):(iv), (iii):(iv), (v):(i), (v):(ii), (v):(iii), (v):(iv). As shown in Tables 1-9, each of these mixtures can be presented in a ratio of 10:90, 20:80, 30:70, 40:60, 50:50, 60:40, 70:30, 80:20, 90:10.

TABLE 1

| i | ii |
|---|---|
| 10 | 90 |
| 20 | 80 |
| 30 | 70 |
| 40 | 60 |
| 50 | 50 |
| 60 | 40 |
| 70 | 30 |
| 80 | 20 |
| 90 | 10 |

TABLE 2

| i | iii |
|---|---|
| 10 | 90 |
| 20 | 80 |
| 30 | 70 |
| 40 | 60 |
| 50 | 50 |
| 60 | 40 |
| 70 | 30 |
| 80 | 20 |
| 90 | 10 |

TABLE 3

| ii | iii |
|---|---|
| 10 | 90 |
| 20 | 80 |
| 30 | 70 |
| 40 | 60 |
| 50 | 50 |
| 60 | 40 |
| 70 | 30 |
| 80 | 20 |
| 90 | 10 |

TABLE 4

| ii | iv |
|---|---|
| 10 | 90 |
| 20 | 80 |
| 30 | 70 |
| 40 | 60 |
| 50 | 50 |
| 60 | 40 |
| 70 | 30 |
| 80 | 20 |
| 90 | 10 |

TABLE 5

| iii | iv |
|---|---|
| 10 | 90 |
| 20 | 80 |
| 30 | 70 |
| 40 | 60 |
| 50 | 50 |
| 60 | 40 |
| 70 | 30 |
| 80 | 20 |
| 90 | 10 |

TABLE 6

| v | i |
|---|---|
| 10 | 90 |
| 20 | 80 |
| 30 | 70 |
| 40 | 60 |
| 50 | 50 |
| 60 | 40 |
| 70 | 30 |
| 80 | 20 |
| 90 | 10 |

TABLE 7

| v | ii |
|---|---|
| 10 | 90 |
| 20 | 80 |
| 30 | 70 |
| 40 | 60 |
| 50 | 50 |
| 60 | 40 |
| 70 | 30 |
| 80 | 20 |
| 90 | 10 |

TABLE 8

| v | iii |
|---|---|
| 10 | 90 |
| 20 | 80 |
| 30 | 70 |
| 40 | 60 |
| 50 | 50 |
| 60 | 40 |
| 70 | 30 |
| 80 | 20 |
| 90 | 10 |

TABLE 9

| v | IV |
|---|---|
| 10 | 90 |
| 20 | 80 |
| 30 | 70 |
| 40 | 60 |
| 50 | 50 |
| 60 | 40 |
| 70 | 30 |
| 80 | 20 |
| 90 | 10 |

In certain embodiments of the present invention is a composition that is a mixture of three compounds, such as the mixture of the following compounds (i):(ii):(iii), (ii):(iii):(iv), (iii):(iv):(i), (i):(ii):(iv). The ratio of these compounds in each of these mixtures is listed in Tables 10-28 below. Each of Tables 10-28 below describes the relative amounts of the different compounds. For example, Table 10 lists the relative amounts of compounds (i):(ii):(iii); the relative amounts of compounds (ii):(iii):(iv); the relative amounts of compounds (iii):(iv)(i); and the relative amounts of compounds (i):(ii):(iv).

TABLE 10

| Mixture | i | ii | iii |
| | ii | iii | iv |
| | iii | iv | i |
| | i | ii | iv |
| Ratio | 10 | 10 | 80 |
| | 20 | 10 | 70 |
| | 30 | 10 | 60 |
| | 40 | 10 | 50 |
| | 50 | 10 | 40 |
| | 60 | 10 | 30 |
| | 70 | 10 | 20 |
| | 80 | 10 | 10 |
| | 90 | 10 | 0 |
| | 100 | 0 | 0 |

TABLE 11

| Mixture | i | ii | iii |
| | ii | iii | iv |
| | iii | iv | i |
| | i | ii | iv |
| Ratio | 10 | 20 | 70 |
| | 20 | 20 | 60 |
| | 30 | 20 | 50 |
| | 40 | 20 | 40 |
| | 50 | 20 | 30 |
| | 60 | 20 | 20 |
| | 70 | 20 | 10 |
| | 80 | 20 | 0 |
| | 90 | 0 | 10 |

TABLE 12

| Mixture | i | ii | iii |
| | ii | iii | iv |
| | iii | iv | i |
| | i | ii | iv |
| Ratio | 10 | 30 | 60 |
| | 20 | 30 | 50 |
| | 30 | 30 | 40 |
| | 40 | 30 | 30 |
| | 50 | 30 | 20 |
| | 60 | 30 | 10 |

TABLE 12-continued

| 70 | 30 | 0 |
| 80 | 0 | 20 |
| 90 | 0 | 10 |

TABLE 13

| Mixture | i | ii | iii |
| | ii | iii | iv |
| | iii | iv | i |
| | i | ii | iv |
| Ratio | 10 | 40 | 50 |
| | 20 | 40 | 40 |
| | 30 | 40 | 30 |
| | 40 | 40 | 20 |
| | 50 | 40 | 10 |
| | 60 | 40 | 0 |
| | 70 | 0 | 30 |
| | 80 | 0 | 20 |
| | 90 | 0 | 10 |

TABLE 14

| Mixture | i | ii | iii |
| | ii | iii | iv |
| | iii | iv | i |
| | i | ii | iv |
| Ratio | 10 | 50 | 40 |
| | 20 | 50 | 30 |
| | 30 | 50 | 20 |
| | 40 | 50 | 10 |
| | 50 | 50 | 0 |

TABLE 15

| Mixture | i | ii | iii |
| | ii | iii | iv |
| | iii | iv | i |
| | i | ii | iv |
| Ratio | 10 | 60 | 30 |
| | 20 | 60 | 20 |
| | 30 | 60 | 10 |
| | 40 | 60 | 0 |
| | 50 | 0 | 50 |

TABLE 16

| Mixture | i | ii | iii |
| | ii | iii | iv |
| | iii | iv | i |
| | i | ii | iv |
| Ratio | 10 | 70 | 20 |
| | 20 | 70 | 10 |
| | 30 | 70 | 0 |
| | 40 | 0 | 60 |

TABLE 17

| Mixture | i | ii | iii |
| | ii | iii | iv |
| | iii | iv | i |
| | i | ii | iv |
| Ratio | 10 | 80 | 10 |
| | 20 | 80 | 0 |
| | 30 | 0 | 70 |

TABLE 18

| Mixture | i | ii | iii |
|---|---|---|---|
| | ii | iii | iv |
| | iii | iv | i |
| | i | ii | iv |
| Ratio | 10 | 90 | 0 |
| | 20 | 0 | 80 |

TABLE 19

| Mixture | i | ii | iii |
|---|---|---|---|
| | ii | iii | iv |
| | iii | iv | i |
| | i | ii | iv |
| Ratio | 0 | 100 | 0 |

TABLE 20

| Mixture | i | ii | iii |
|---|---|---|---|
| | ii | iii | iv |
| | iii | iv | i |
| | i | ii | iv |
| Ratio | 80 | 10 | 10 |
| | 70 | 10 | 20 |
| | 60 | 10 | 30 |
| | 50 | 10 | 40 |
| | 40 | 10 | 50 |
| | 30 | 10 | 60 |
| | 20 | 10 | 70 |
| | 10 | 10 | 80 |
| | 0 | 10 | 90 |
| | 0 | 0 | 100 |

TABLE 21

| Mixture | i | ii | iii |
|---|---|---|---|
| | ii | iii | iv |
| | iii | iv | i |
| | i | ii | iv |
| Ratio | 70 | 20 | 10 |
| | 60 | 20 | 20 |
| | 50 | 20 | 30 |
| | 40 | 20 | 40 |
| | 30 | 20 | 50 |
| | 20 | 20 | 60 |
| | 10 | 20 | 70 |
| | 0 | 20 | 80 |
| | 10 | 0 | 90 |

TABLE 22

| Mixture | i | ii | iii |
|---|---|---|---|
| | ii | iii | iv |
| | iii | iv | i |
| | i | ii | iv |
| Ratio | 60 | 30 | 10 |
| | 50 | 30 | 20 |
| | 40 | 30 | 30 |
| | 30 | 30 | 40 |
| | 20 | 30 | 50 |
| | 10 | 30 | 60 |
| | 0 | 30 | 70 |
| | 20 | 0 | 80 |
| | 10 | 0 | 90 |

TABLE 23

| Mixture | i | ii | iii |
|---|---|---|---|
| | ii | iii | iv |

TABLE 23-continued

| | iii | iv | i |
|---|---|---|---|
| | i | ii | iv |
| Ratio | 50 | 40 | 10 |
| | 40 | 40 | 20 |
| | 30 | 40 | 30 |
| | 20 | 40 | 40 |
| | 10 | 40 | 50 |
| | 0 | 40 | 60 |
| | 30 | 0 | 70 |
| | 20 | 0 | 80 |
| | 10 | 0 | 90 |

TABLE 24

| Mixture | i | ii | iii |
|---|---|---|---|
| | ii | iii | iv |
| | iii | iv | i |
| | i | ii | iv |
| Ratio | 40 | 50 | 10 |
| | 30 | 50 | 20 |
| | 20 | 50 | 30 |
| | 10 | 50 | 40 |
| | 0 | 50 | 50 |

TABLE 25

| Mixture | i | ii | iii |
|---|---|---|---|
| | ii | iii | iv |
| | iii | iv | i |
| | i | ii | iv |
| Ratio | 30 | 60 | 10 |
| | 20 | 60 | 20 |
| | 10 | 60 | 30 |
| | 0 | 60 | 40 |
| | 50 | 0 | 50 |

TABLE 26

| Mixture | i | ii | iii |
|---|---|---|---|
| | ii | iii | iv |
| | iii | iv | i |
| | i | ii | iv |
| Ratio | 20 | 70 | 10 |
| | 10 | 70 | 20 |
| | 0 | 70 | 30 |
| | 60 | 0 | 40 |

TABLE 27

| Mixture | i | ii | iii |
|---|---|---|---|
| | ii | iii | iv |
| | iii | iv | i |
| | i | ii | iv |
| Ratio | 10 | 80 | 10 |
| | 0 | 80 | 20 |
| | 70 | 0 | 30 |

TABLE 28

| Mixture | i | ii | iii |
|---|---|---|---|
| | ii | iii | iv |
| | iii | iv | i |
| | i | ii | iv |
| Ratio | 10 | 90 | 10 |
| | 80 | 0 | 20 |

In certain embodiments, the present invention is a composition that is a mixture of compounds in the following ratio: (i):(ii) is 50:50.

In certain embodiments, the present invention is a composition that is a mixture of compounds in the following ratio: (i):(iii) is 50:50.

In certain embodiments, the present invention is a composition that is a mixture of compounds in the following ratio: (i):(iv) is 50:50.

In certain embodiments, the present invention is a composition that is a mixture of compounds in the following ratio: (ii):(iii) is 50:50.

In certain embodiments, the present invention is a composition that is a mixture of compounds in the following ratio: (ii):(iv) is 50:50.

In certain embodiments, the present invention is a composition that is a mixture of compounds in the following ratio: (iii):(iv) is 50:50.

In certain embodiments, the present invention is a composition that is a mixture of the following compounds: (v):(i), (v):(ii), (v):(iii), (v):(iv). Each of these mixtures can be present in a ratio of is 10:90, 20:80, 30:70, 40:60, 50:50, 60:40, 70:30, 80:20, 90:10.

In yet other embodiments of the present invention the compound is represented by the following structural formula:

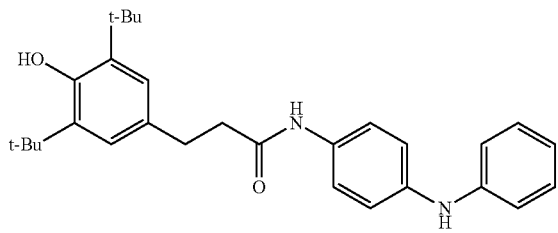

In one embodiments, the present invention is represented by the following structural formula:

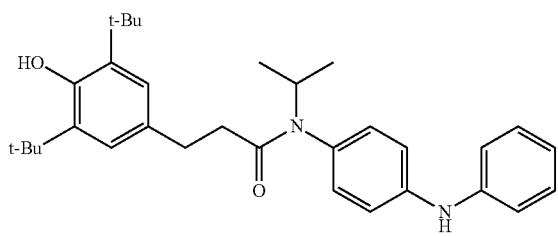 [SMILES: CC(C)N(C(=O)CCc1cc(C(C)(C)C)c(O)c(C(C)(C)C)c1)c1ccc(Nc2ccccc2)cc1]

In other embodiments, the present invention is represented by the following structural formula:

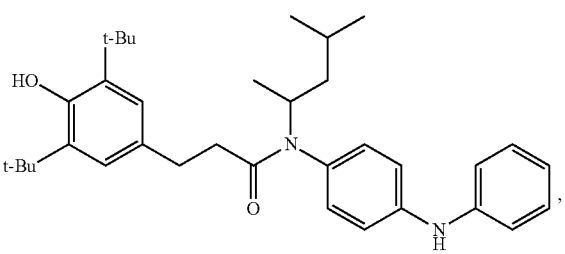 [SMILES: CC(C)CC(C)N(C(=O)CCc1cc(C(C)(C)C)c(O)c(C(C)(C)C)c1)c1ccc(Nc2ccccc2)cc1]

In one embodiments, the present invention is represented by the following structural formula:

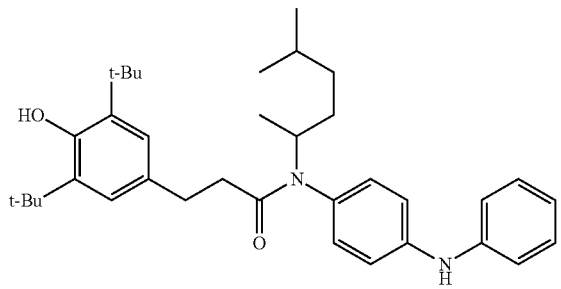 [SMILES: CC(C)CCC(C)N(C(=O)CCc1cc(C(C)(C)C)c(O)c(C(C)(C)C)c1)c1ccc(Nc2ccccc2)cc1]

In yet other embodiments, the present invention is represented by the following structural formula:

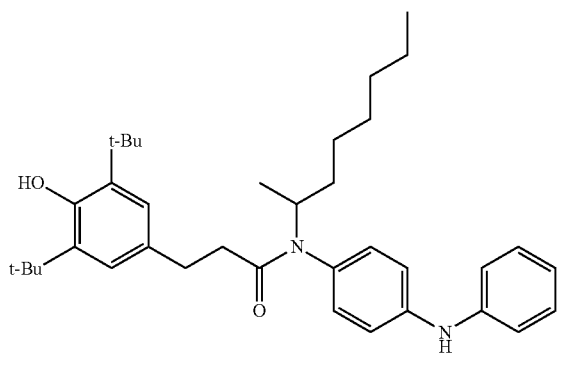 [SMILES: CCCCCCC(C)N(C(=O)CCc1cc(C(C)(C)C)c(O)c(C(C)(C)C)c1)c1ccc(Nc2ccccc2)cc1]

In one embodiment, the present invention is represented by structural formula (III):

Structural Formulas III

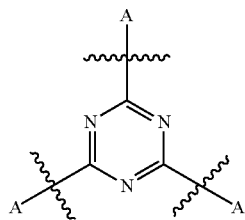

wherein each A is independently selected from

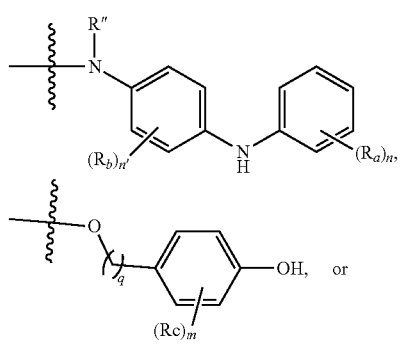

OH, or

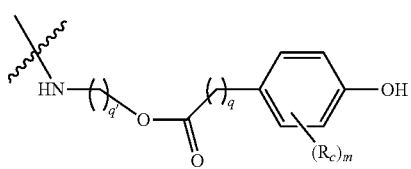

and the remaining variables are as described in the immediately preceding paragraphs or structural formula (I). Each q, q' independently is 2. Each q, q' independently is 3. Each q, q' independently is 4.

In yet another embodiment, the compounds of structural formula (III) are represented by the following structural formulas:

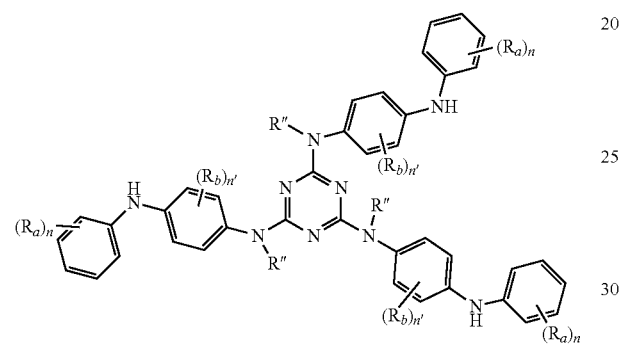

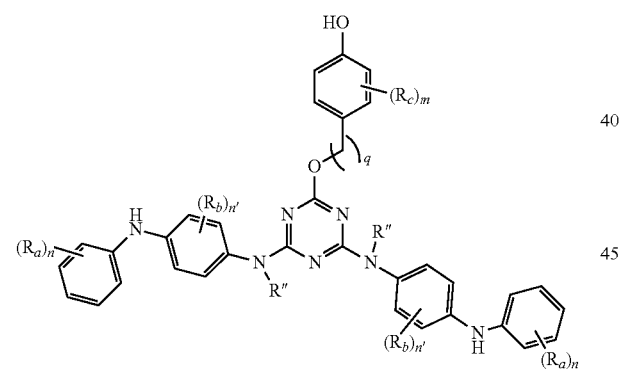

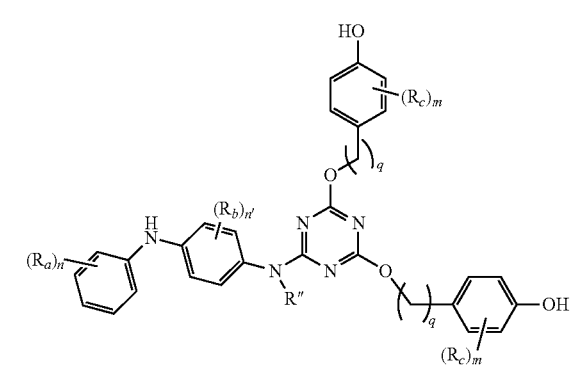

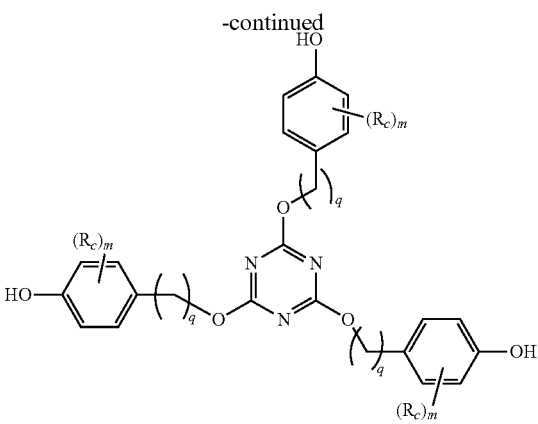

wherein $R_c$ is a bulky alkyl group substituent bonded to a ring carbon atom adjacent (ortho) to a ring carbon atom substituted with an —OH group. Each $R_c$ is H, independently an optionally substituted C1-C10 alkyl group, a tertiary carbon group, an optionally substituted aryl group, and optionally substituted alkoxy group, an optionally substituted carbonyl group, an optionally substituted alkoxycarbonyl group, an optionally substituted aryloxycarbonyl group, —OH, —SH or —NH$_2$ or an optionally substituted carbocyclic or heterocyclic non-aromatic ring. m is an integer from 0 to 2.

R" is H, independently an optionally substituted C1-C10 alkyl group, an optionally substituted aryl group, and optionally substituted alkoxy group, an optionally substituted carbonyl group, an optionally substituted alkoxycarbonyl group, an optionally substituted aryloxycarbonyl group, or an optionally substituted carbocyclic or heterocyclic non-aromatic ring.

Each $R_a$, is H, independently an optionally substituted C1-C10 alkyl group, an optionally substituted aryl group, and optionally substituted alkoxy group, an optionally substituted carbonyl group, an optionally substituted alkoxycarbonyl group, an optionally substituted aryloxycarbonyl group, —OH, —SH or —NH$_2$ or an optionally substituted carbocyclic or heterocyclic non-aromatic ring. n is an integer from 0 to 5.

Each $R_b$, is H, independently an optionally substituted C1-C10 alkyl group, an optionally substituted aryl group, and optionally substituted alkoxy group, an optionally substituted carbonyl group, an optionally substituted alkoxycarbonyl group, an optionally substituted aryloxycarbonyl group, —OH, —SH or —NH$_2$ or an optionally substituted carbocyclic or heterocyclic non-aromatic ring. n' is an integer from 0 to 4.

In another embodiment, the compound of structural formula (III) is represented by structural formulas (IX):

Structural Formulas IX

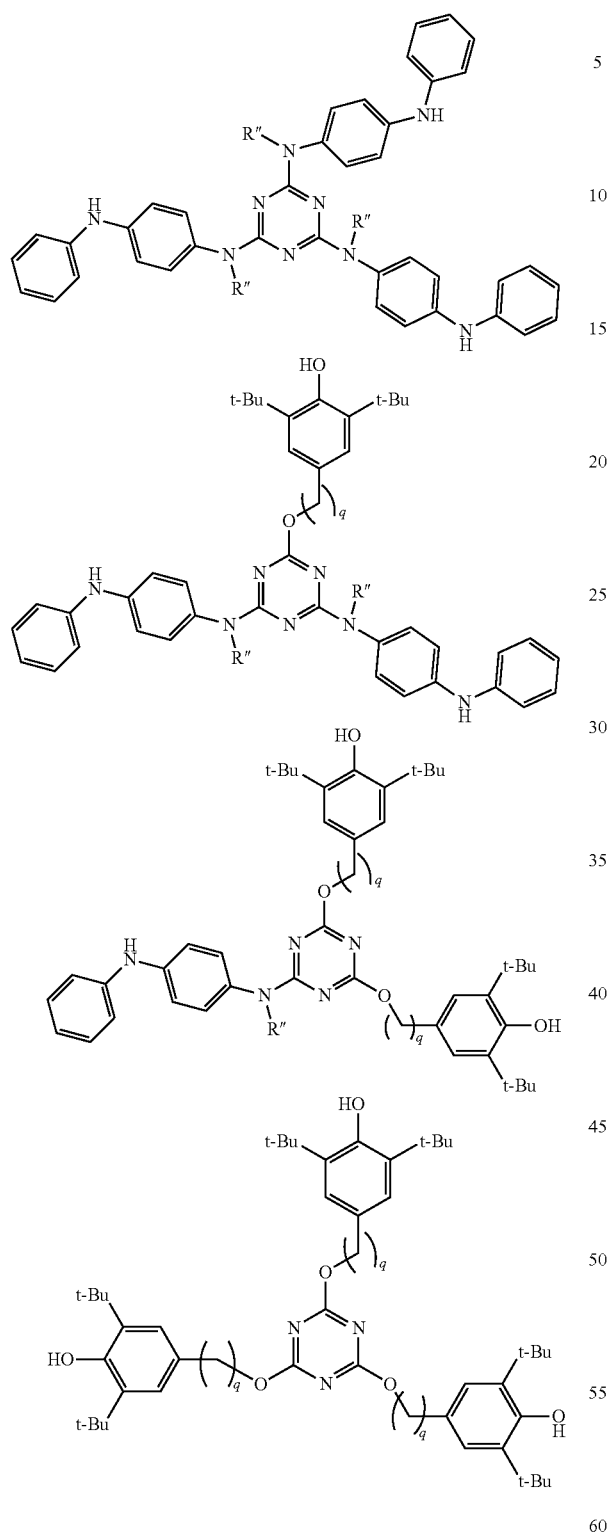

wherein the remainder of the variables are as defined above.

In some embodiments of Structural Formula IX, q is an integer 1-8; in other embodiments, q is 1-4; in other embodiments, q is 2

In some embodiments of Structural Formula IX, R″ is a C1-C10 alkyl.

In another embodiment of Structural Formula IX, q is 3, where in R″ is H, a C1-C10 alkyl.

In another embodiment of Structural Formula IX, R″ is selected from the group of consisting of

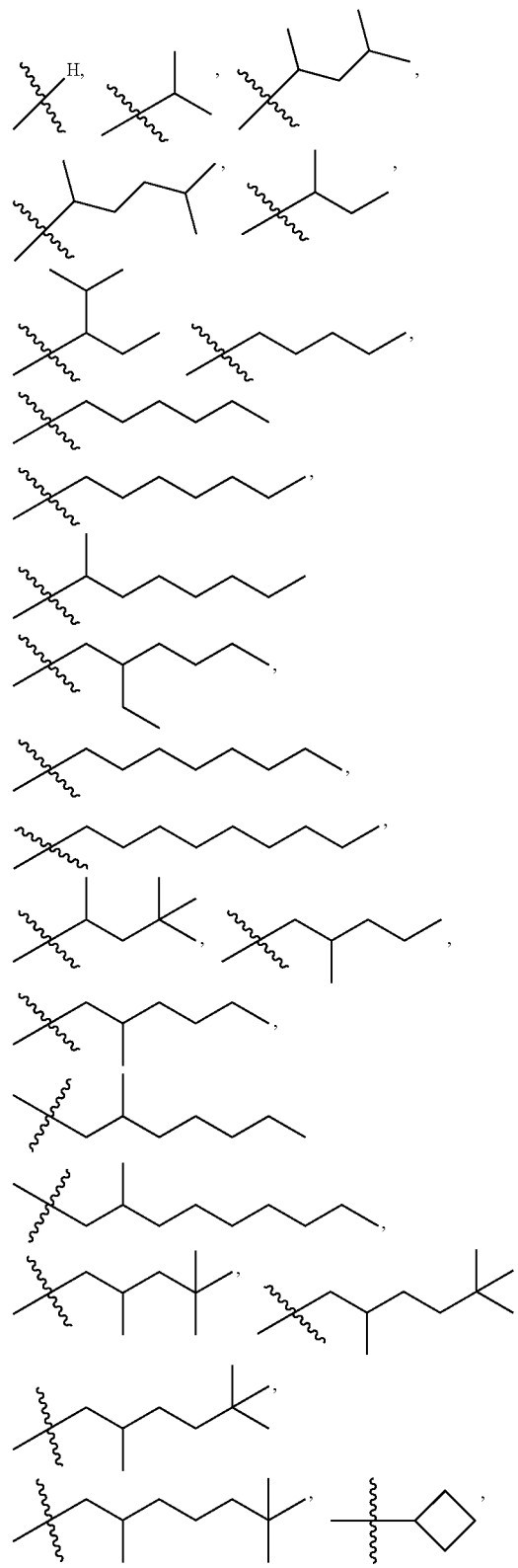

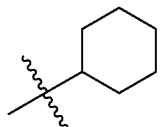
In yet other embodiments, the compounds of structural formulas (IX) are represented by the following structural formulas:
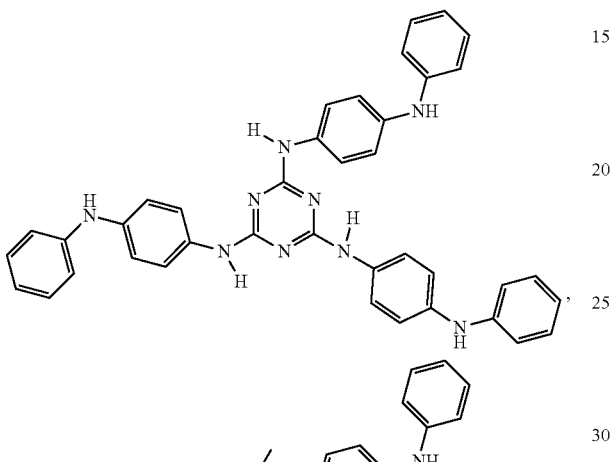
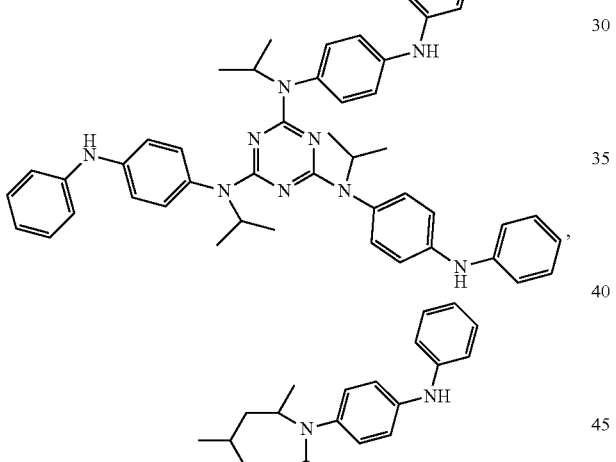
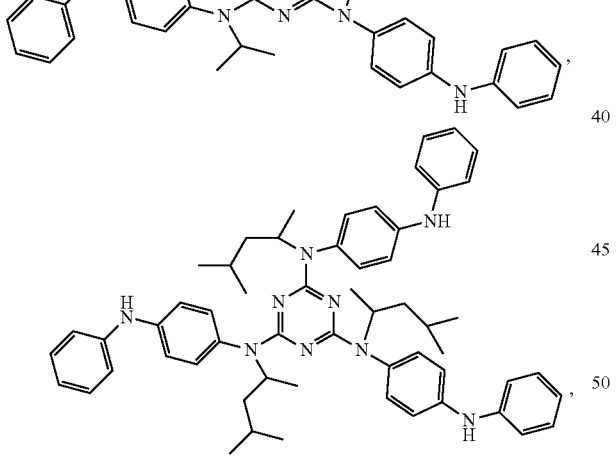
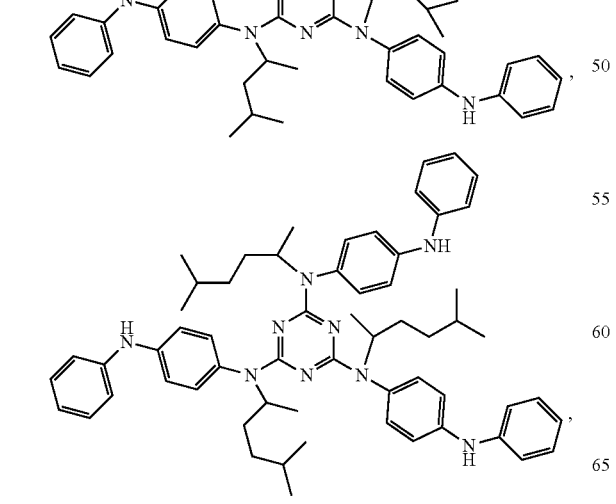
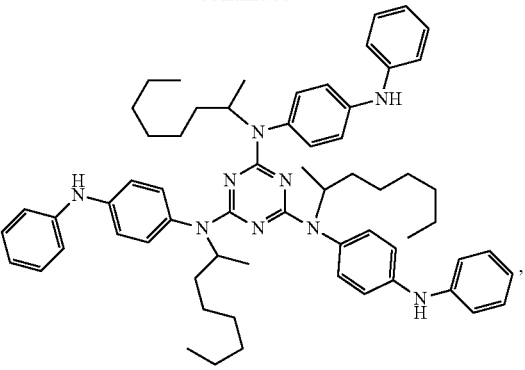
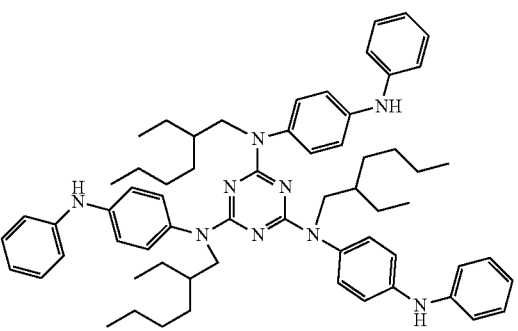
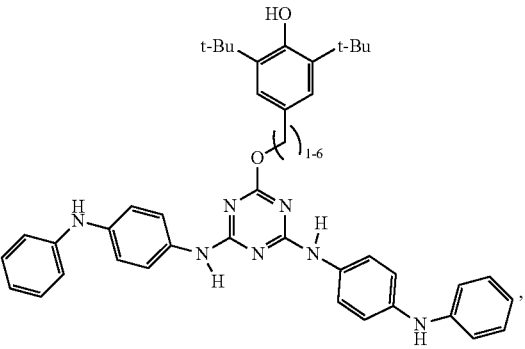
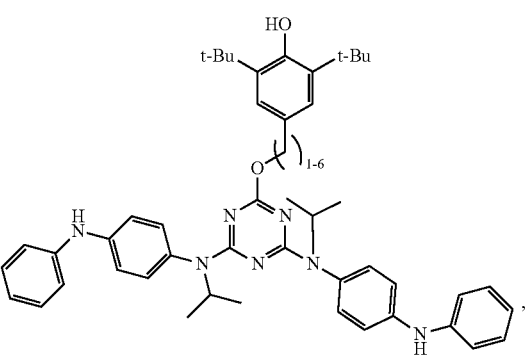

37
-continued
38
-continued
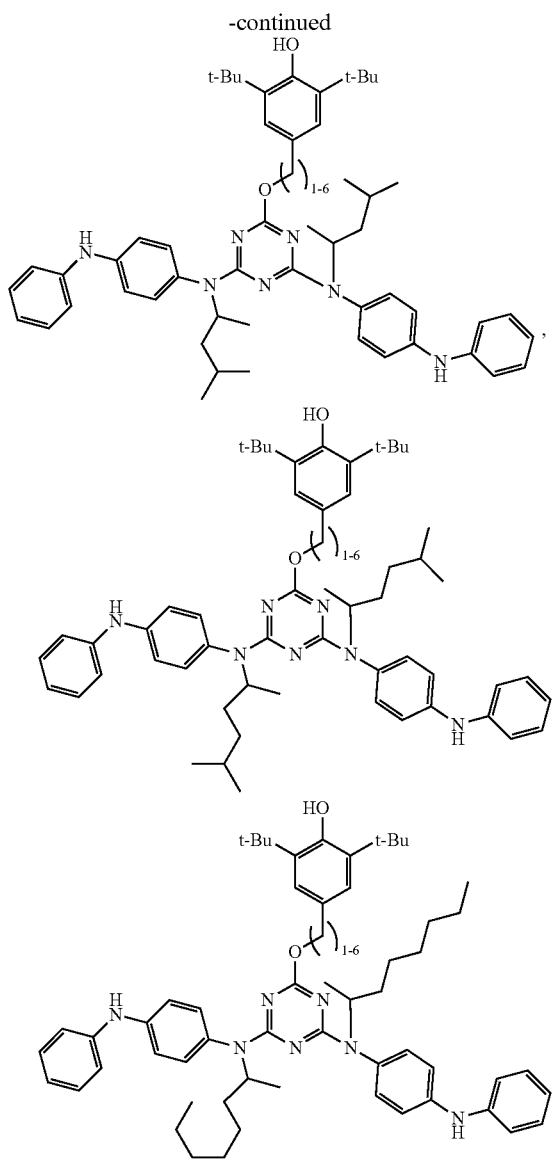
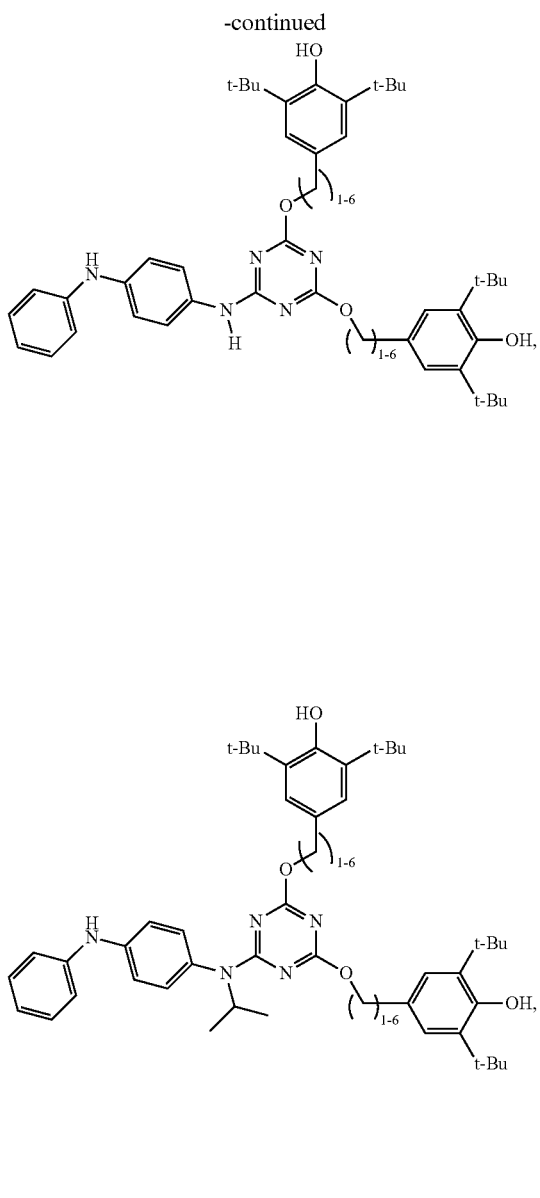
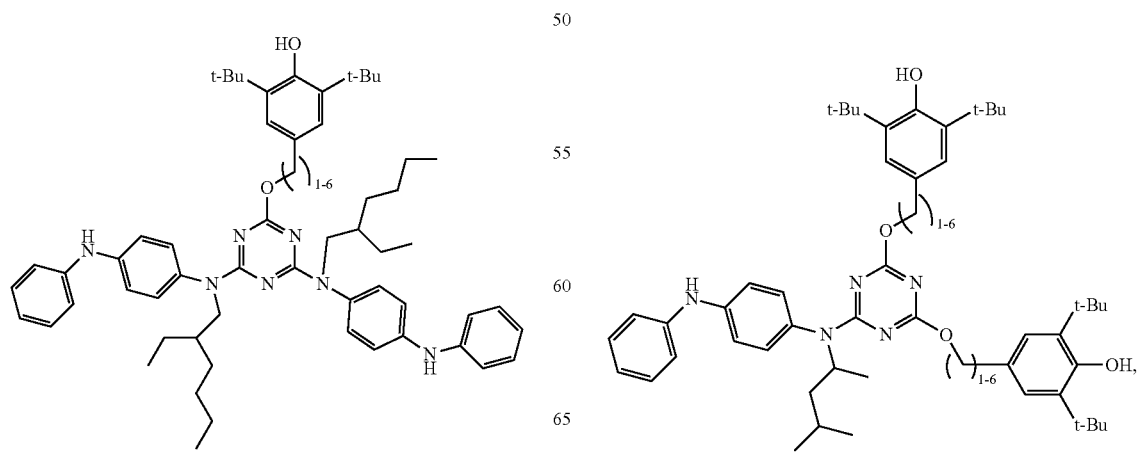

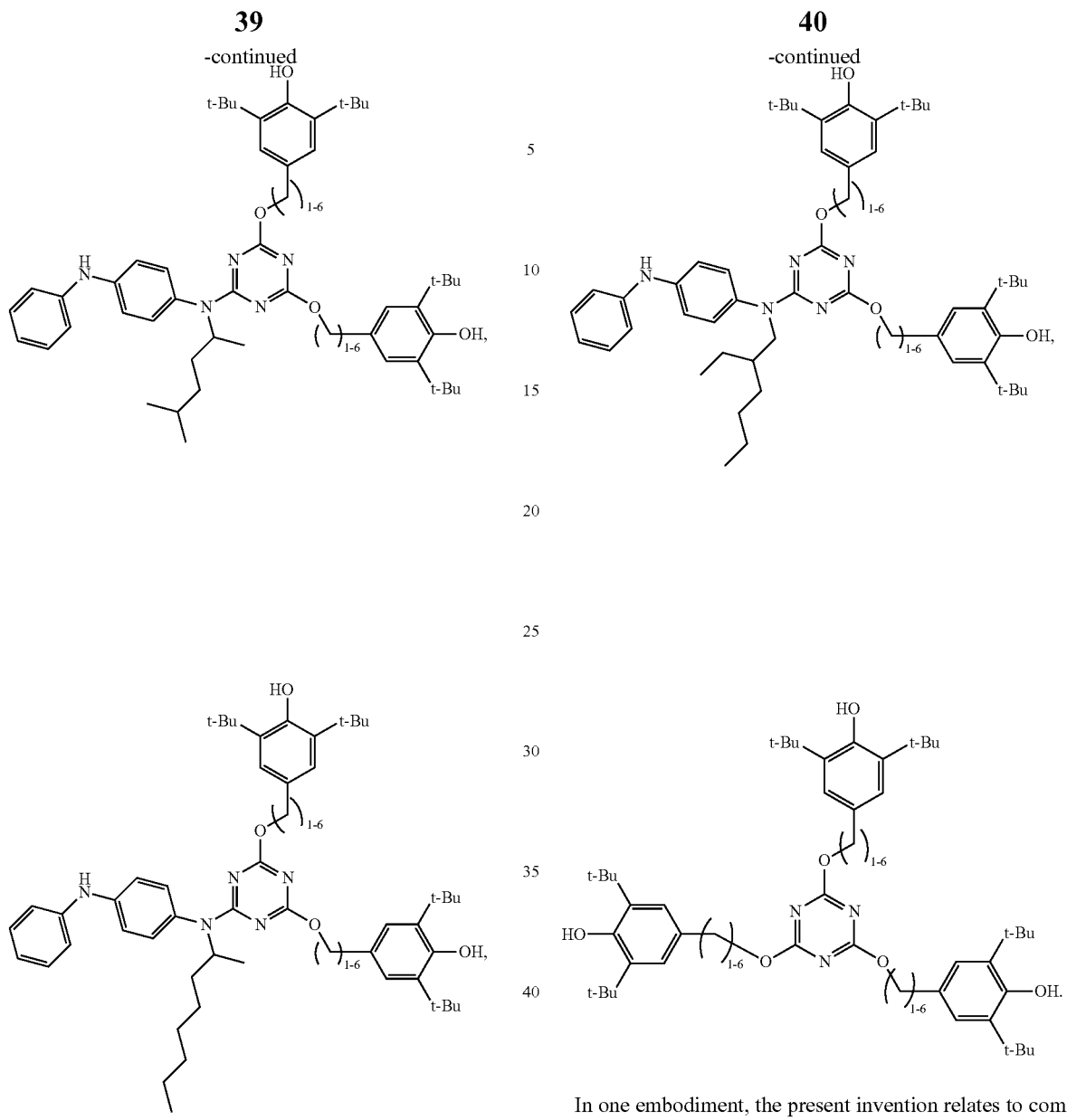
In one embodiment, the present invention relates to compounds represented by structural formulas (X):
Structural Formulas X
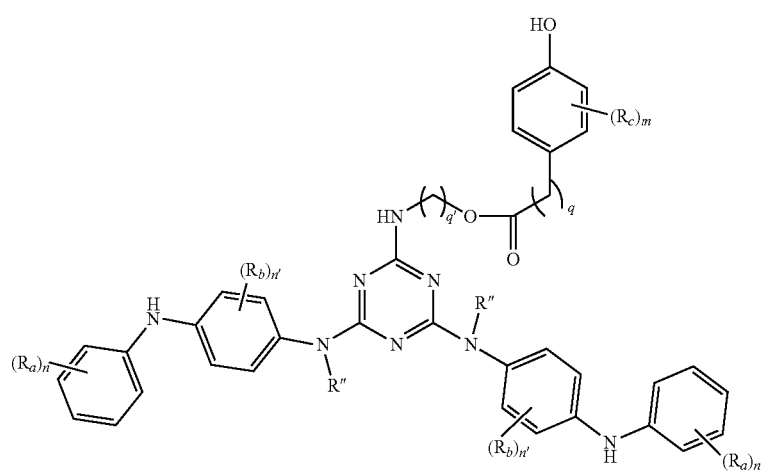

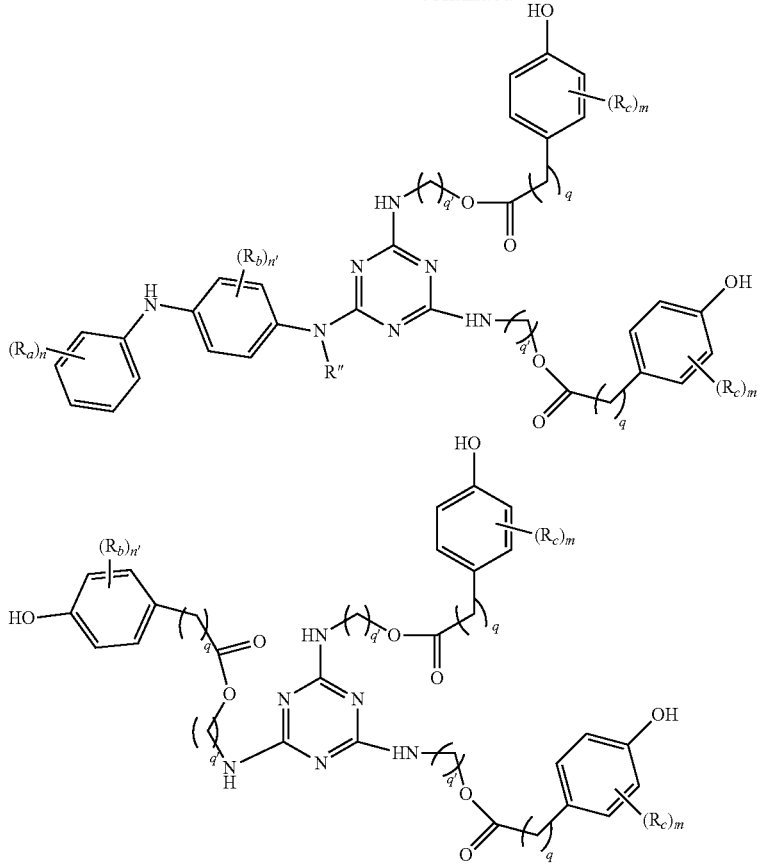

wherein q is an integer from 1 to 8; in some embodiments, q is an integer from 1 to 4; in some embodiments, q is 2;

R" is C1-C10 alkyl;

q' is an integer from 1 to 8; in some embodiments, q' is an integer from 2 to 6; in some embodiments, q' is 2;

m is 2;

$R_c$ is tertiary butyl group;

and n is 0.

In another embodiment, q and q' are 2.

In another embodiment, R" in structural formula (X) is selected from the group of consisting of

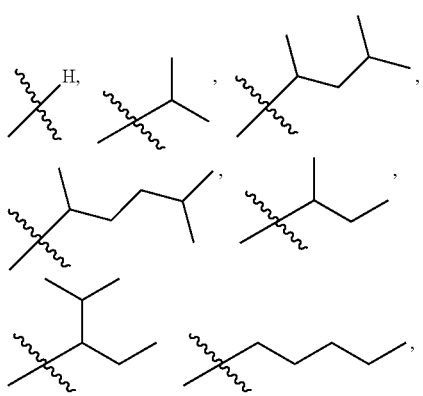

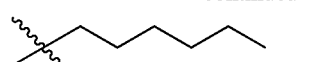

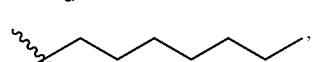

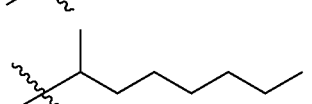

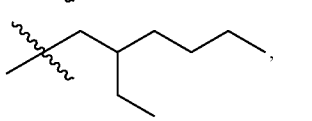

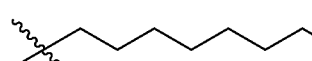

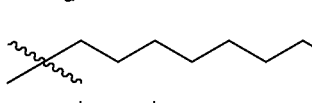

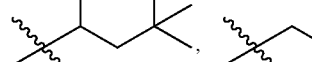

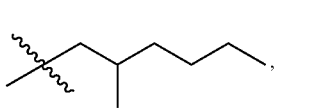

-continued

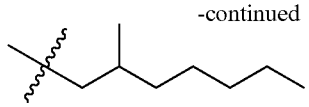

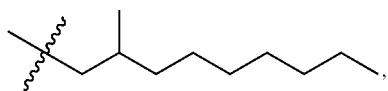

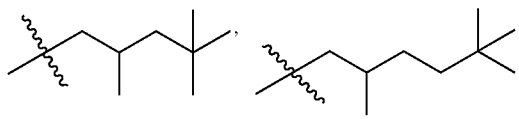

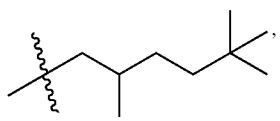

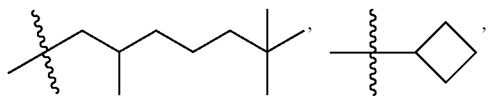

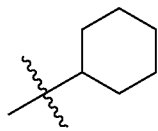

In yet another embodiment, the present invention is a compound represented by structural formula IV Structural Formula IV

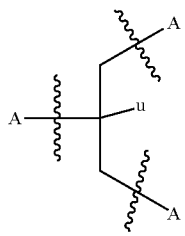

wherein each A is independently

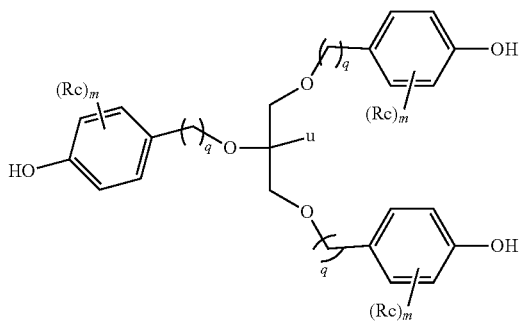

and the remaining variables are as described in the immediately preceding paragraph or structural formula (I). q, independently for each occurrence, is an integer from 1 to 10. Each q, q' independently is 2. Each q, q' independently is 3. Each q, q' independently is 4.

In one embodiment, the compounds are represented by structural formulas (XI):

Structural Formulas XI

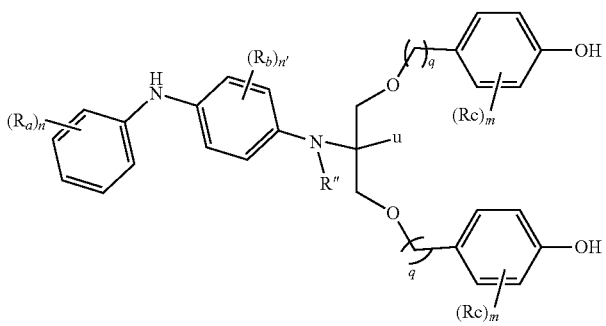

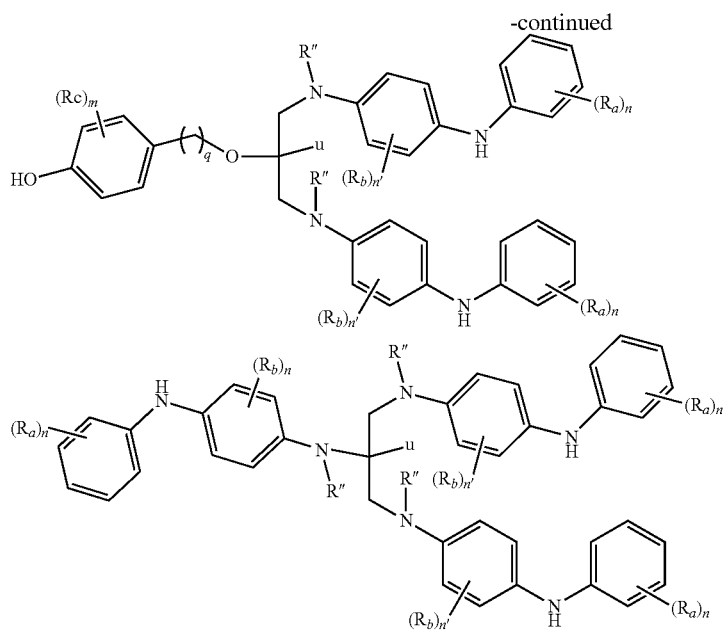
Wherein u is —H or —CH$_2$CH$_3$, q is an integer 1-8. q is 1-4. q is preferably 3. R" is C1-C10 alkyl. m is 2, R$_c$ is tertiary butyl group and n is 0, and R" is selected from
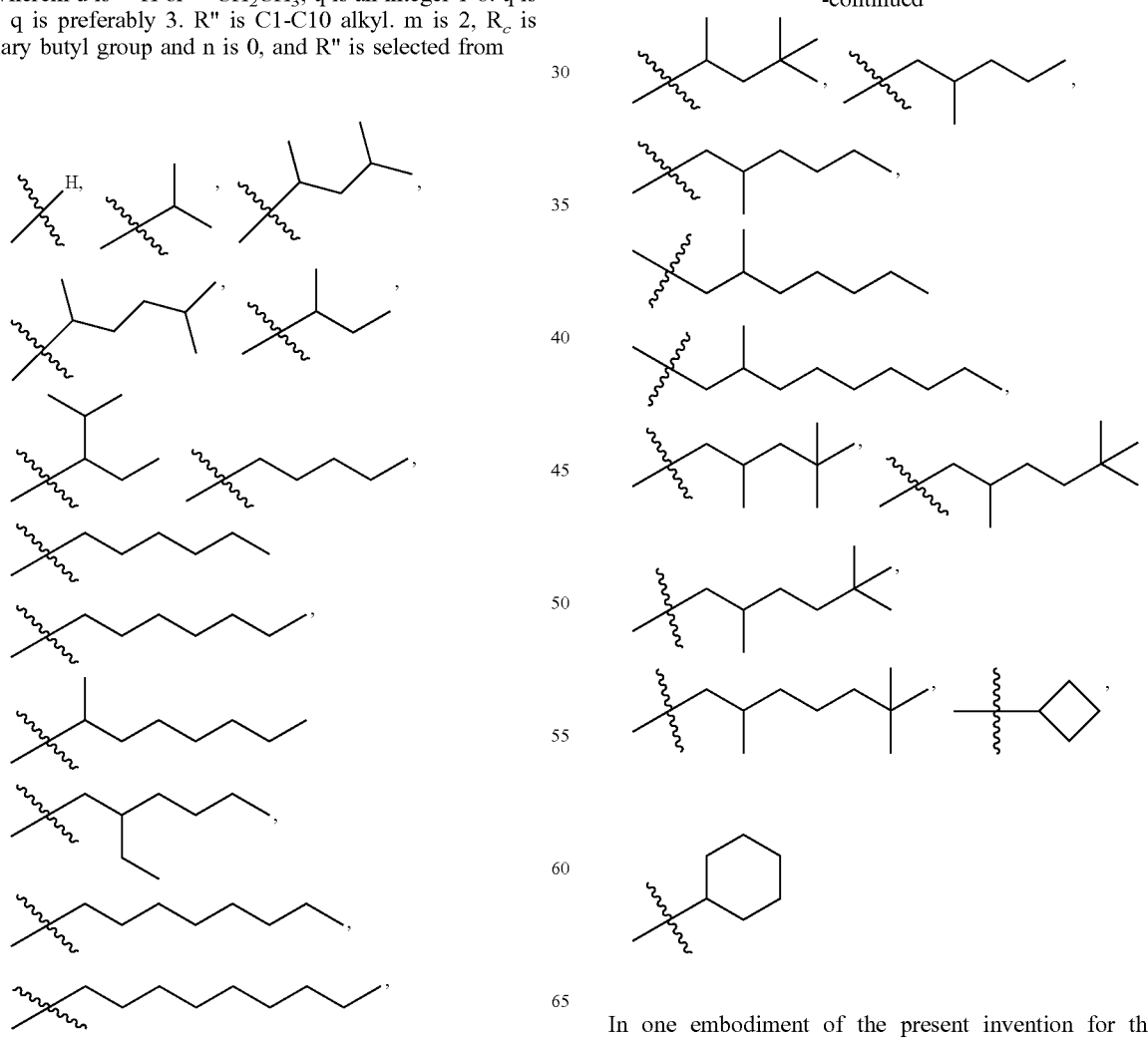
In one embodiment of the present invention for the compounds represented by structural formulas (XII):

Structural Formulas XII
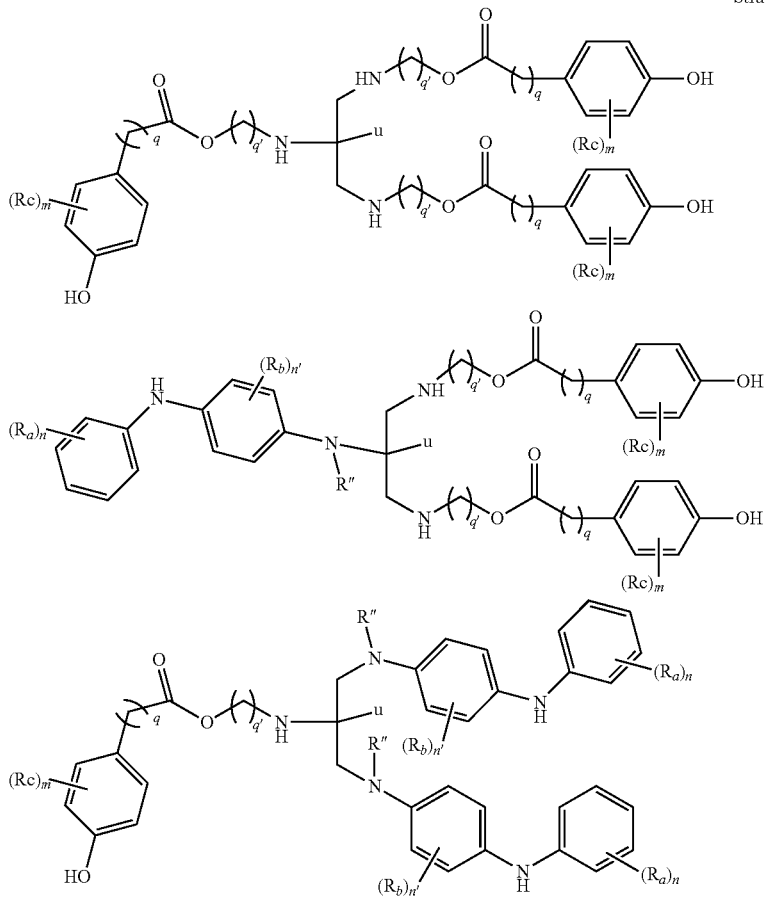
Wherein q is an integer 1-8. q is 1-4. q is preferably 2. R" is C1-C10 alkyl. q' is 1-8. q' is 2-6. Preferably q' is 2. m is 2, $R_c$ is tertiary butyl group and n is 0,
In another embodiment q and q' are 2; and R" is a C1-C10 alkyl. In another embodiment, R" in structural formula (XII) is selected from the group of consisting of
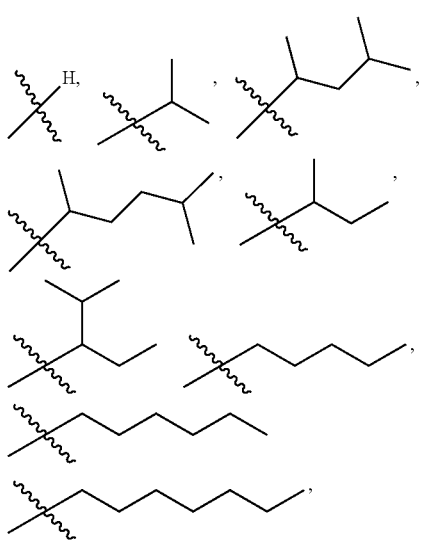
-continued
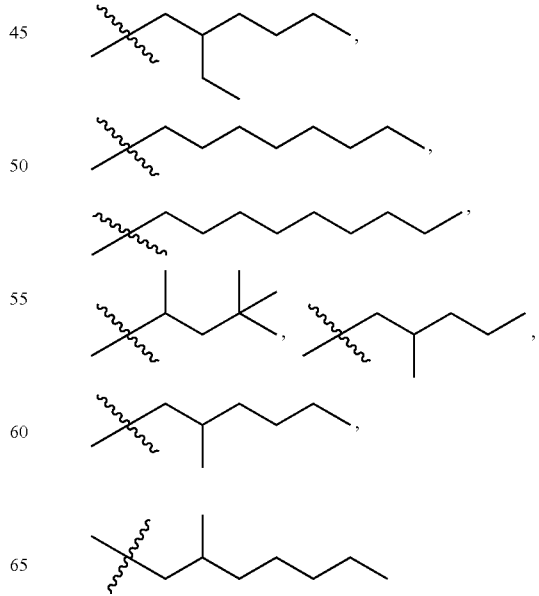

-continued
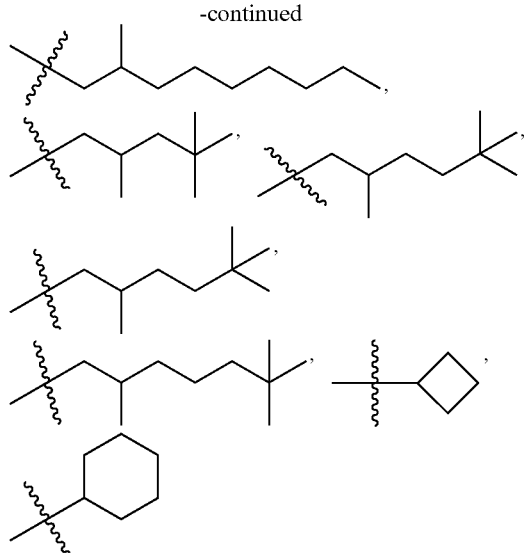
In yet other embodiments of the present invention the compounds represented by structural formulas (XII) are represented by the following structural formulas:
Wherein u is —H or —CH$_2$—CH$_3$, and R″ is selected from the group of consisting of
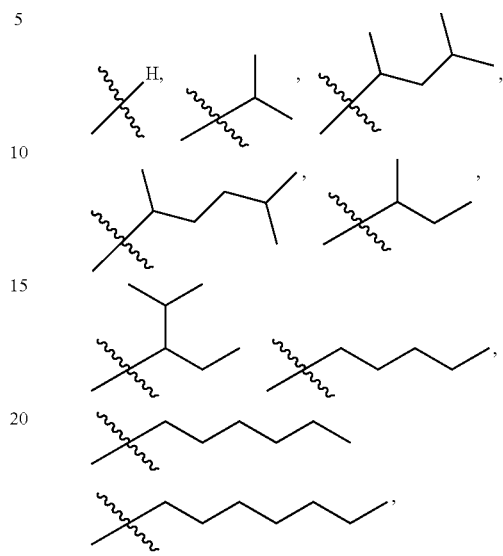
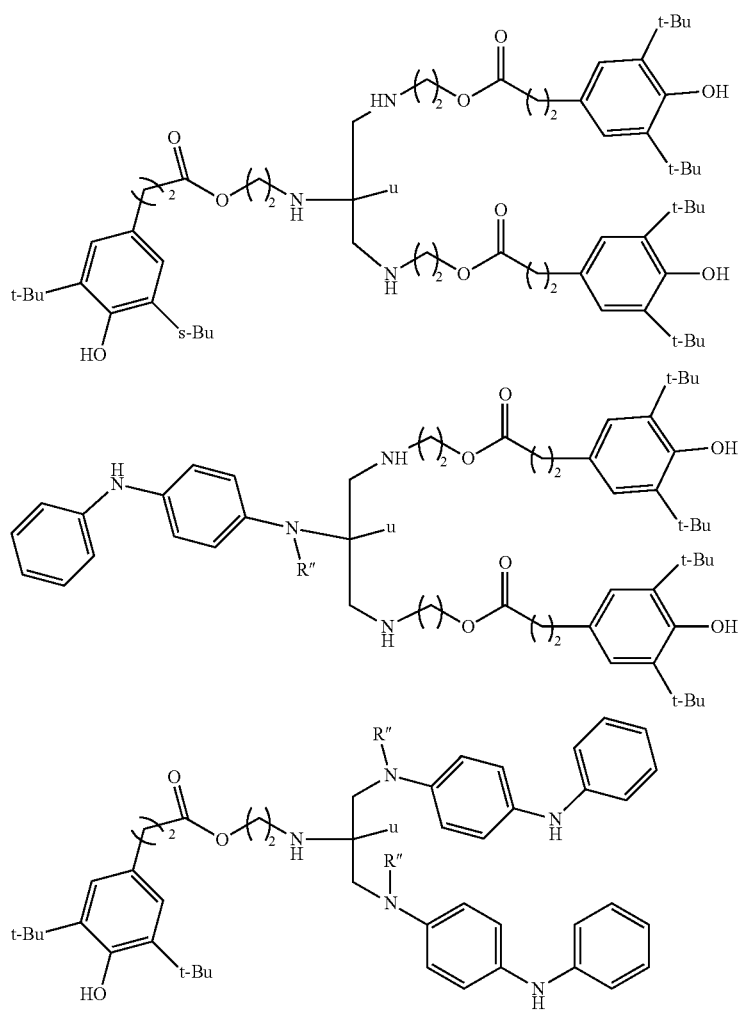

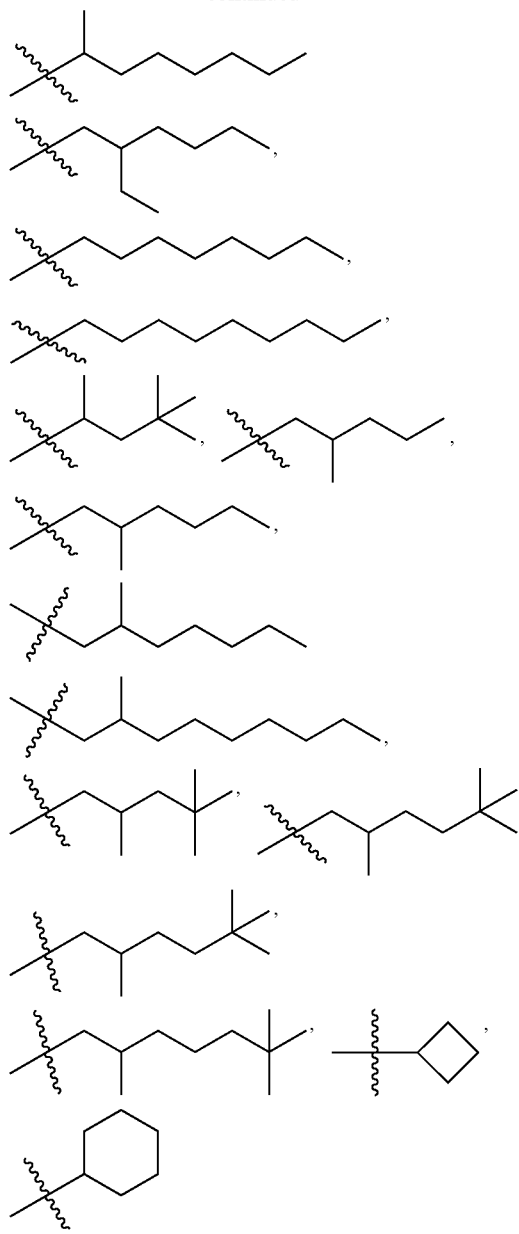

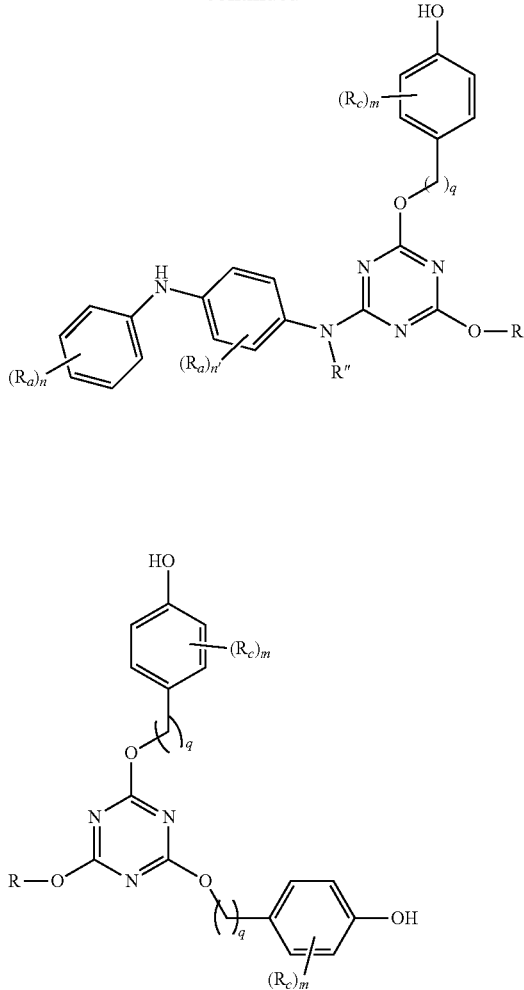

Wherein q is an integer 1-8. q is 1-4. q is preferably 2. R" is C1-C10 alkyl. q' is 1-8. q' is 2-6. Preferably q' is 2. m is 2, $R_c$ is tertiary butyl group and n is 0.

In another embodiment q and q' are 2, where in R" is a C1-C10 alkyl. R is C1-10 alkyl chain, linear or branched. R is C2 to C6. Preferably R is C6 or C8 linear or branched carbon chain.

In yet other embodiments of the present invention the compounds represented by structural formulas (XIII) are represented by the following structural formulas:

In yet other embodiments of the present invention the compounds represented by structural formula (XIII):

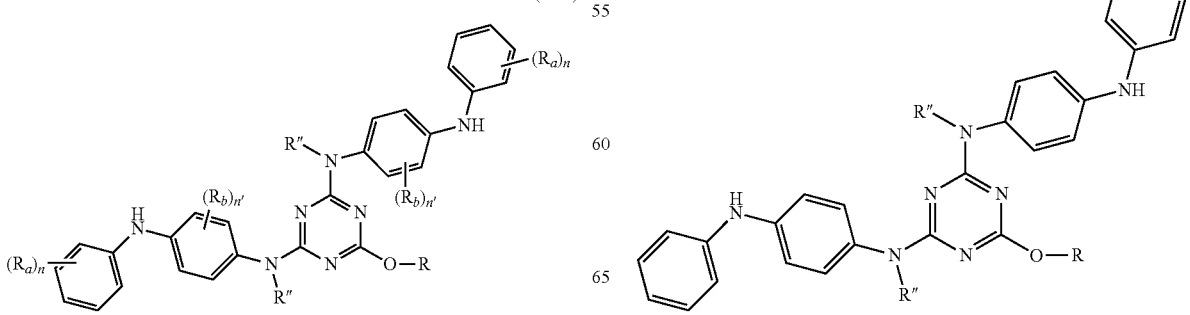

Structural Formula (XIII)

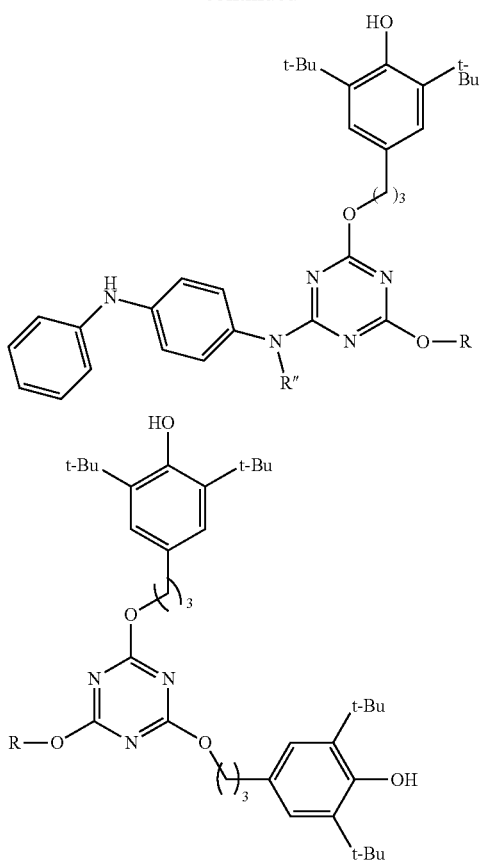
Wherein u is —H or —CH$_2$—CH$_3$, R is C1-10 linear or branched alkyl chain, preferably C4 or C6 carbon linear or branched chain, and R″ is selected from the group of consisting of
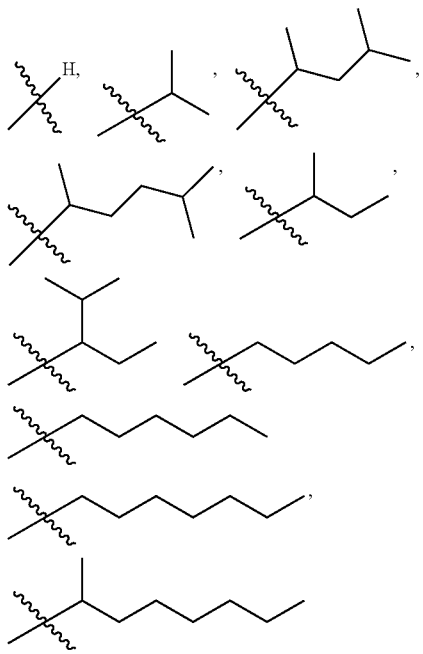
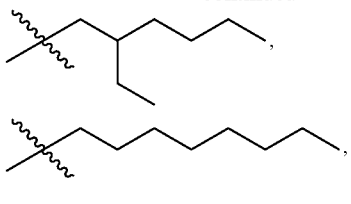
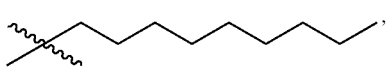
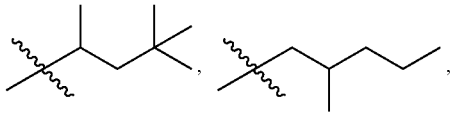
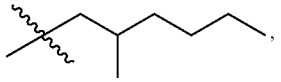
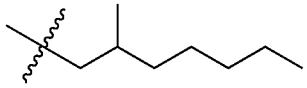
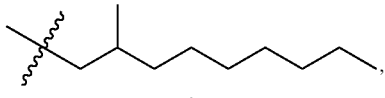
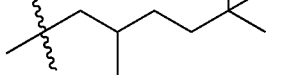
In another embodiment of the present invention the compounds represented by structural formula (XIV):
Structural Formula (XIV)
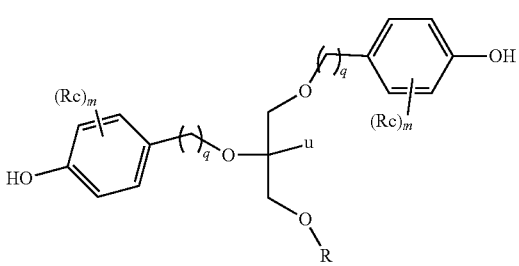

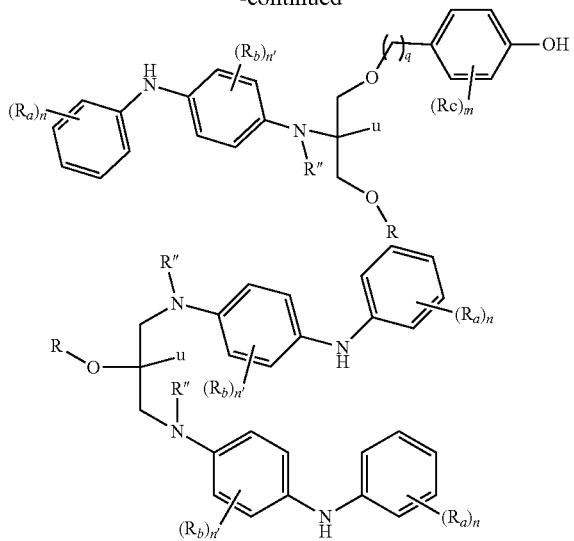

Wherein u is H or —CH$_2$—CH$_3$, R is C1-10 linear or branched alkyl chain, preferably C4 or C6 carbon linear or branched chain, and R″ is selected from the group of consisting of

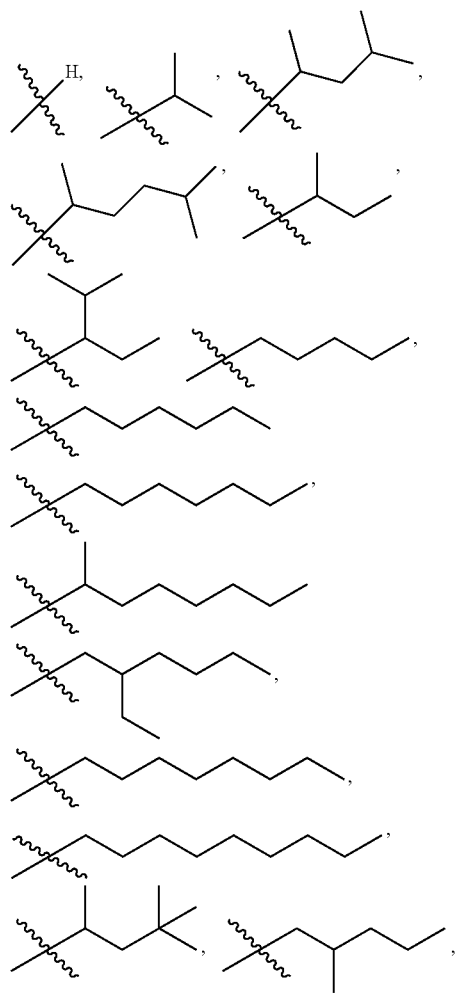

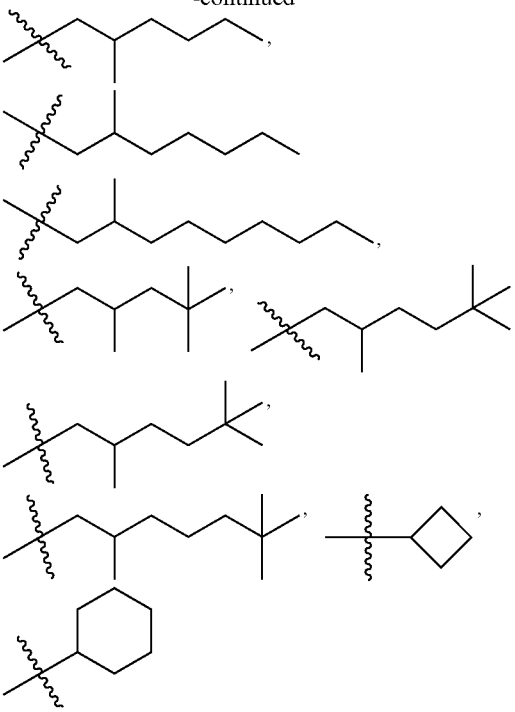

In certain embodiments, the antioxidant composition of the present invention comprising first antioxidant compound of Structural formula (I) and optionally a second antioxidant selected from the group consisting of: amine antioxidants, phenolic antioxidants, sulfurized organic compounds, organo-borate compounds, phosphite and phosphate antioxidants, copper compounds, zinc dithiodiphosphates, and phenolic antioxidants and/or aminic antioxidants.

In other embodiments, the weight ratio of the first antioxidant to the second antioxidant is 99:1 to 1:99.

In yet other embodiments, the weight ratio of the second antioxidant to the first antioxidant is 1:1.

In other embodiments, the weight ratio of the second antioxidant to the first antioxidant is 1:1.

In other embodiments the weight ratio of the second antioxidant to the first antioxidant is 2:1 to 10:1.

In certain other embodiments of the present invention after combining the amine and amino-phenol derivative in a suitable solvent the combination is refluxed at a temperature between 50 and 180° C., between 90 and 130° C., between 100 and 110° C. In certain embodiments, the combination is refluxed for between 1 and 48 hours, between 6 and 36 hours, between 12 and 24 hours or between 18 and 20 hours.

In certain embodiments, in the methods of the present invention the solvent is selected from the group consisting of toluene, tetrahydrofuran, acetonitrile, dichloromethane, methanol, ethanol and butanol.

In certain embodiments of the present invention equimolar amounts of the phenol derivative and the amine are combined. In certain embodiments of the present invention the phenol derivative and the amine are combined a 1:0.5, 1:1.2, 1:1.5, 1:1.0 molar ratio of phenol derivative:amine.

In one embodiment the above method can be conducted in one step and can be conducted without catalyst. The process can be conducted by mixing two starting components in a suitable solvent and heating the reaction mixture to reflux.

In one embodiment, the above method involves mixing of sterically hindered phenolic acid derivatives, preferably 3-(3,5-ditert-butyl-4-hydroxyphenyl)propanoic acid with substituted amines e.g., N-phenyl-1,4-phenylene-diamine in a suitable solvent. The solvent can be a single solvent or mixture of two solvents. In another embodiment, the solvent is toluene.

One embodiment of the present invention is directed to combining equimolar amounts of the starting components, e.g., 3-(3,5-ditert-butyl-4-hydroxyphenyl)propanoic acid and N-phenyl-1,4-phenylene-diamine, in toluene and refluxing the reaction mixture at, e.g., 110° C.

In certain embodiment the methods of the present invention are simple, efficient, and economical and can be conducted without catalyst.

In certain other embodiments in the methods of the present invention, when solvent is used it can be recycled by separating the solvents from the reaction mixture using distillation.

In yet another embodiment, in the above method involves mixing of sterically hindered phenolic acid derivatives, 3-(3,5-ditert-butyl-4-hydroxyphenyl) propanoic acid with substituted amines e.g., $N^1$-isopropyl-$N^4$-phenylbenzene-1,4-diamine in a suitable solvent. The solvent can be a single solvent or mixture of two solvents. In another embodiment, the solvent is toluene.

In yet another embodiment, in the above method involves mixing of sterically hindered phenolic acid derivatives, 3-(3,5-ditert-butyl-4-hydroxyphenyl)propanoic acid with substituted amines e.g., $N^1$-(1,3-dimethylbutyl)-$N^4$-phenylbenzene-1,4-diamine in a suitable solvent. The solvent can be a single solvent or mixture of two solvents. In another embodiment, the solvent is toluene.

In yet another embodiment, in the above method involves mixing of sterically hindered phenolic acid derivatives, 3-(3,5-ditert-butyl-4-hydroxyphenyl)propanoic acid with substituted amines e.g., $N^1$-(1,4-dimethylpentyl)-$N^4$-phenylbenzene-1,4-diamine in a suitable solvent. The solvent can be a single solvent or mixture of two solvents. In another embodiment, the solvent is toluene.

In another embodiment, in the above method involves mixing of sterically hindered phenolic acid derivatives, 3-(3,5-ditert-butyl-4-hydroxyphenyl)propanoic acid with substituted amines e.g. N-sec-octyl-N'-phenyl-p-phenylene-diamine in a suitable solvent. The solvent can be a single solvent or mixture of two solvents. In another embodiment, the solvent is toluene.

In one embodiment, in the above method involves mixing of equimolar amounts of the starting components, e.g. 3-(3,5-ditert-butyl-4-hydroxyphenyl)propanoic acid and mixture of at least two amines selected from N-phenyl-1,4-phenylene-diamine; $N^1$-isopropyl-$N^4$-phenylbenzene-1,4-diamine; $N^1$-(1,3-dimethylbutyl)-$N^4$-phenylbenzene-1,4-diamine; $N^1$-(1,4-dimethylpentyl)-$N^4$-phenylbenzene-1,4-diamine; N-sec-octyl-N'-phenyl-p-phenylenediamine in toluene and refluxing the reaction mixture at, e.g., 110° C.

In one embodiment, the above method involves mixing of sterically hindered phenolic acid derivatives, preferably methyl 3-(3,5-ditert-butyl-4-hydroxyphenyl)propanoate with substituted amines e.g., N-phenyl-1,4-phenylene-diamine in a suitable solvent. The solvent can be a single solvent or mixture of two solvents. In another embodiment, the solvent is toluene.

One embodiment of the present invention is directed to combining equimolar amounts of the starting components, e.g., methyl 3-(3,5-ditert-butyl-4-hydroxyphenyl)propanoate and N-phenyl-1,4-phenylene-diamine, in toluene and refluxing the reaction mixture at, e.g., 110° C.

In certain embodiment the methods of the present invention are simple, efficient, and economical and can be conducted without catalyst.

In certain other embodiments in the methods of the present invention, when solvent is used it can be recycled by separating the solvents from the reaction mixture using distillation.

In yet another embodiment, in the above method involves mixing of sterically hindered phenolic acid derivatives, methyl 3-(3,5-ditert-butyl-4-hydroxyphenyl)propanoate with substituted amines e.g., $N^1$-isopropyl-$N^4$-phenylbenzene-1,4-diamine in a suitable solvent. The solvent can be a single solvent or mixture of two solvents. In another embodiment, the solvent is toluene.

In yet another embodiment, in the above method involves mixing of sterically hindered phenolic acid derivatives methyl 3-(3,5-ditert-butyl-4-hydroxyphenyl)propanoate with substituted amines e.g., $N^1$-(1,3-dimethylbutyl)-$N^4$-phenylbenzene-1,4-diamine in a suitable solvent. The solvent can be a single solvent or mixture of two solvents. In another embodiment, the solvent is toluene.

In yet another embodiment, in the above method involves mixing of sterically hindered phenolic acid derivatives, 3-(3,5-ditert-butyl-4-hydroxyphenyl)propionyl chloride with substituted amines e.g., $N^1$-(1,4-dimethylpentyl)-$N^4$-phenylbenzene-1,4-diamine in a suitable solvent. The solvent can be a single solvent or mixture of two solvents. In another embodiment, the solvent is toluene.

In yet another embodiment, in the above method involves mixing of sterically hindered phenolic acid derivatives, 3-(3,5-ditert-butyl-4-hydroxyphenyl)propionyl chloride with substituted amines e.g., N-sec-octyl-N'-phenyl-p-phenylenediamine in a suitable solvent. The solvent can be a single solvent or mixture of two solvents. In another embodiment, the solvent is toluene.

In one embodiment, in the above method involves mixing of equimolar amounts of the starting components, e.g. 3-(3,5-ditert-butyl-4-hydroxyphenyl)propionyl chloride and mixture of at least two amines selected from N-phenyl-1,4-phenylene-diamine; $N^1$-isopropyl-$N^4$-phenylbenzene-1,4-diamine; $N^1$-(1,3-dimethylbutyl)-$N^4$-phenylbenzene-1,4-diamine; $N^1$-(1,4-dimethylpentyl)-$N^4$-phenylbenzene-1,4-diamine; N-sec-octyl-N'-phenyl-p-phenylenediamine in toluene and refluxing the reaction mixture at, e.g., 110° C.

In one embodiment, the above method involves mixing of sterically hindered phenolic acid derivatives, preferably 3-(3,5-ditert-butyl-4-hydroxyphenyl)propionyl chloride with substituted amines e.g., N-phenyl-1,4-phenylene-diamine in a suitable solvent. The solvent can be a single solvent or mixture of two solvents. In another embodiment, the solvent is toluene.

One embodiment of the present invention is directed to combining equimolar amounts of the starting components, e.g. 3-(3,5-ditert-butyl-4-hydroxyphenyl)propionyl chloride and N-phenyl-1,4-phenylene-diamine, in toluene and refluxing the reaction mixture at, e.g., 110° C.

In certain embodiment the methods of the present invention are simple, efficient, and economical and can be conducted without catalyst.

In certain other embodiments in the methods of the present invention, when solvent is used it can be recycled by separating the solvents from the reaction mixture using distillation.

In yet another embodiment, in the above method involves mixing of sterically hindered phenolic acid derivatives, 3-(3,5-ditert-butyl-4-hydroxyphenyl)propionyl chloride with substituted amines e.g., $N^1$-isopropyl-$N^4$-phenylbenzene-1,4-diamine in a suitable solvent. The solvent can be a single solvent or mixture of two solvents. In another embodiment, the solvent is toluene.

In yet another embodiment, in the above method involves mixing of sterically hindered phenolic acid derivatives 3-(3,5-ditert-butyl-4-hydroxyphenyl)propionyl chloride with substituted amines e.g., $N^1$-(1,3-dimethylbutyl)-$N^4$-phenylbenzene-1,4-diamine in a suitable solvent. The solvent can be a single solvent or mixture of two solvents. In another embodiment, the solvent is toluene.

In yet another embodiment, in the above method involves mixing of sterically hindered phenolic acid derivatives, 3-(3,5-ditert-butyl-4-hydroxyphenyl)propionyl chloride with substituted amines e.g., $N^1$-(1,4-dimethylpentyl)-$N^4$-phenylbenzene-1,4-diamine in a suitable solvent. The solvent can be a single solvent or mixture of two solvents. In another embodiment, the solvent is toluene.

In yet another embodiment, in the above method involves mixing of sterically hindered phenolic acid derivatives, 3-(3,5-ditert-butyl-4-hydroxyphenyl)propionyl chloride with substituted amines e.g., N-sec-octyl-N'-phenyl-p-phenylenediamine in a suitable solvent. The solvent can be a single solvent or mixture of two solvents. In another embodiment, the solvent is toluene.

In one embodiment, in the above method involves mixing of equimolar amounts of the starting components, e.g. 3-(3,5-ditert-butyl-4-hydroxyphenyl)propionyl chloride and mixture of at least two amines selected from N-phenyl-1,4-phenylene-diamine; $N^1$-isopropyl-$N^4$-phenylbenzene-1,4-diamine; $N^1$-(1,3-dimethylbutyl)-$N^4$-phenylbenzene-1,4-diamine; $N^1$-(1,4-dimethylpentyl)-$N^4$-phenylbenzene-1,4-diamine; N-sec-octyl-N'-phenyl-p-phenylenediamine in toluene and refluxing the reaction mixture at, e.g., 110° C.

In another embodiment of the present invention, a compound is formed by reacting a an amine represented by the following structural formula:

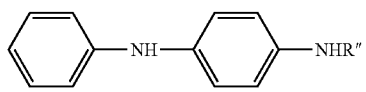

wherein R" is selected from the group of consisting of

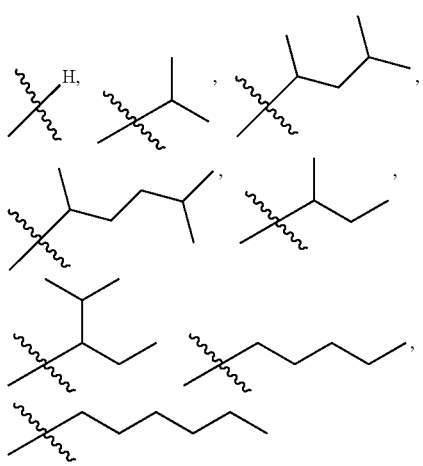

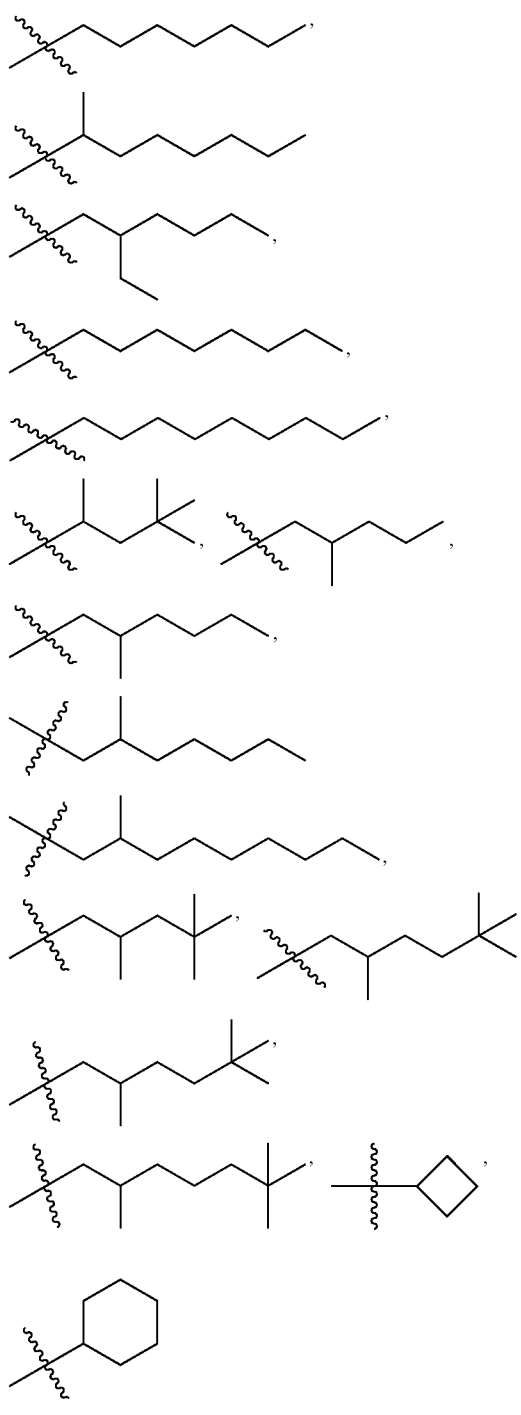

In another embodiment of the present invention, a mixture of compounds is formed by reacting a mixture of amine selected from the compounds represented by structural formula

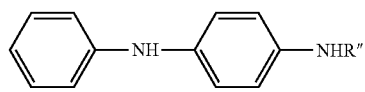

wherein R" is

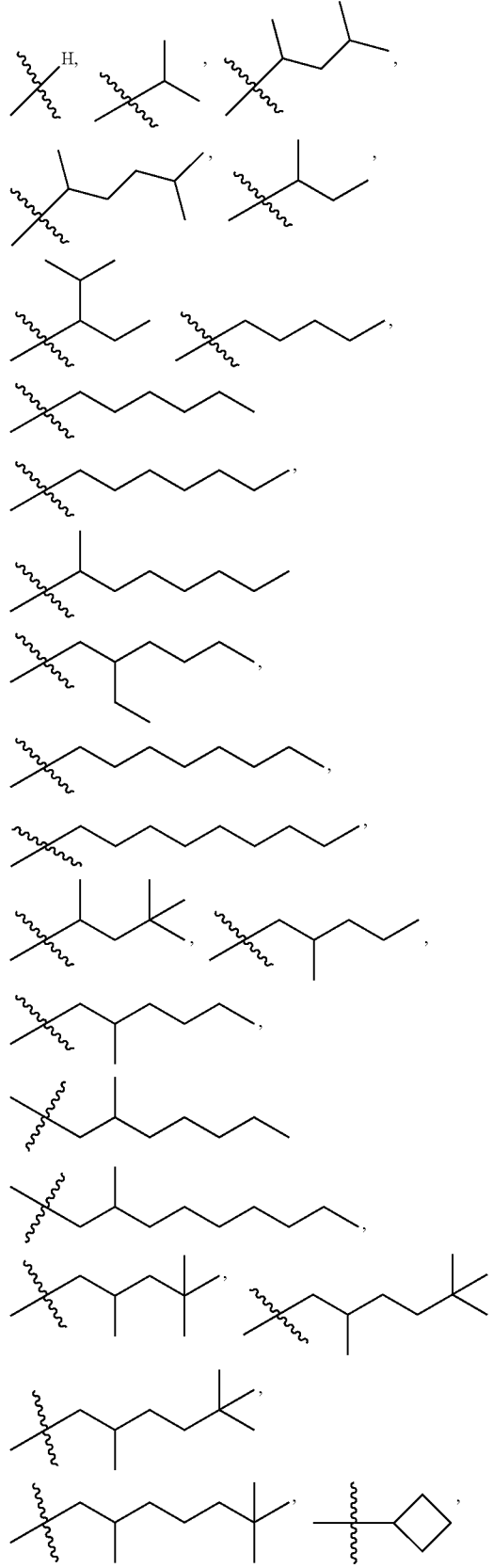

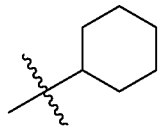

Yet in another embodiment, R" is represented by

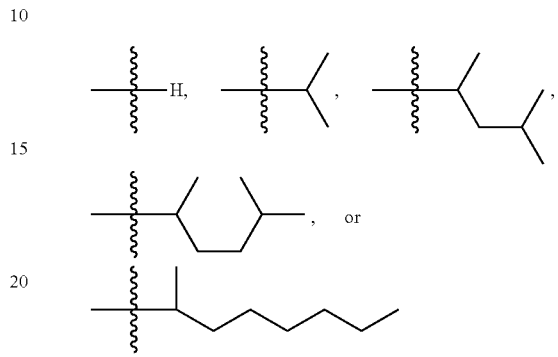

In other embodiments of the present invention the linker [X] is a compound selected from ethane-1,2-diamine, ethane-1,2-diol, 1,2-dichloro-ethane, butanedioic acid, [1,3,5]triazine-2,4,6-triol, propane-1,2,3-triol, trimethylolpropane, trichloromethylopropane, propane-1,2,3-triamine, 2,4,6-Trichloro-[1,3,5]triazine, 3-carboxy-pentanedioic acid, 1,2,3-trichloro-propane with phenol derivatives and amines (A) of Structures I-V In certain other embodiments of the present invention the linker [X] is a compound selected from:

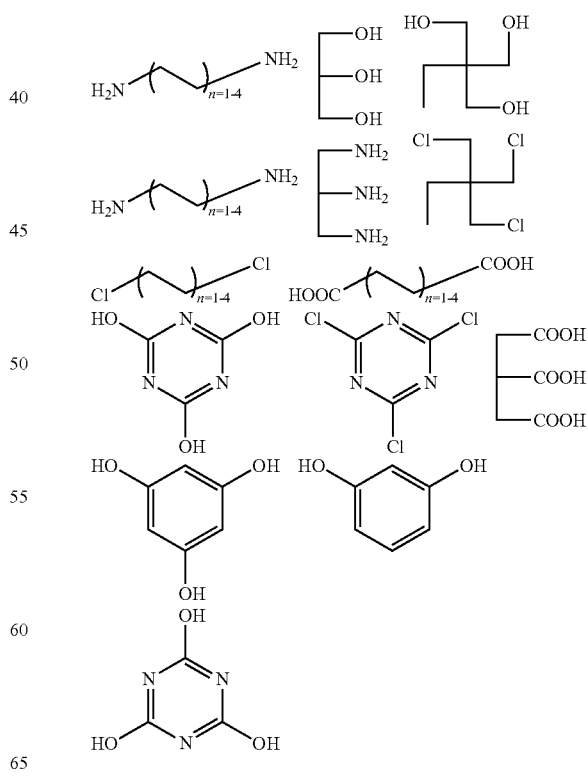

with phenol derivatives and amines (A) of Structures I-V

In certain other embodiments of the present invention after combining the amine and/or phenol derivatives and multifunctional linker in a suitable solvent the combination is refluxed at a temperature between 0 and 150° C., between 90 and 130° C., between 100 and 110° C. In certain embodiments, the combination is refluxed for between 1 and 48 hours, between 6 and 36 hours, between 12 and 24 hours or between 18 and 20 hours. The linkers are di-, tri- or tetrafunctional to attach to amine, amine derivatives, phenol derivatives, e.g., diols, dichloro compounds (e.g., 1,2 dichloroethane, dichlorobutane), cyanuric chloride, cyanuric acid, triglycerol, trichlrogyecrol, trimethyl propane, or trichloro trimethyl propane, pentaerythirtol, tetrachloropentaerythritol.

In certain embodiments, the linker for a compound represented by the following structural formula:

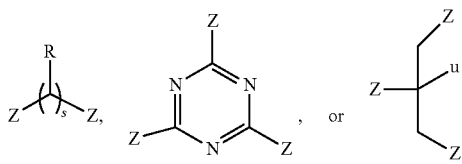

wherein Z is OH or Cl, u is —H or —CH$_2$CH$_3$, or —C1-C10 linear or branched alkyl chain, s is 1-10. R is —H or —OH or an optionally substituted C1-C10 linear or branched alkyl chain.

In other embodiments the amines are represented by the following structural formula:

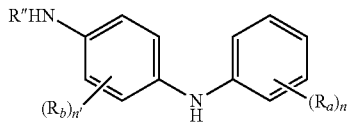

wherein:
each R$_a$ is independently an optionally substituted alkyl;
each R$_b$ is independently an optionally substituted alkyl;
R" is independently —H or an optionally substituted alkyl; and
n is an integer from 0 to 5. n' is an integer from 0 to 4.

In another embodiment, the phenol derivatives are represented by the following structural formula:

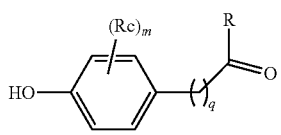

wherein:
each R$_c$ is independently an optionally substituted alkyl or alkoxycarbonyl;
R is —H, —OH, —OCH$_3$, —Cl, or an optionally substituted alkyl;
q is an integer from 0 to 10; and
m is 0 to 4.

In one embodiment, the solvent is selected from the group consisting of methanol, butanol, ethanol, tetrahydrofuran, acetone, acetonitrile, dichloromethane and toluene.

In yet other embodiments, the linker and phenol derivative are first combined in 1:1 or 1:2 or 1:3 molar ratios and the combination is refluxed between 0 and 110° C. It is then followed by further addition of amine to the reaction in 0 or 1 or 2 molar ratio to the linker and refluxed further to complete the reaction.

In other embodiment, the linker and amine are first combined in 1:1 or 1:2 or 1:3 molar ratios and the combination is refluxed between 110° C. It is then followed by further addition of phenol derivative to the reaction in 0 or 1 or 2 molar ratio to the linker and refluxed further to complete the reaction.

One embodiment of the present invention is directed to combining 1:1 or 2:1 or 3:1 or 4:1 molar amounts of the starting components, e.g. 3-(3,5-ditert-butyl-4-hydroxyphenyl) propanoic alcohol and/or amine to the linker molecule, in toluene and refluxing the reaction mixture at, e.g., 110° C.

In yet other embodiment of the present invention is directed to combining 3:1 molar amounts of the starting components, e.g. 3-(3,5-ditert-butyl-4-hydroxyphenyl) propanoic alcohol to the linker molecule (e.g., cyanuric chloride), in toluene at 0-5° C.

In yet other embodiment of the present invention is directed to combining 3:1 molar amounts of the starting components, e.g. 3-(3,5-ditert-butyl-4-hydroxyphenyl) propanoic alcohol to the linker molecule (e.g., cyanuric chloride), in toluene at 40-65° C.

In yet another embodiment of the present invention is directed to combining 3:1 molar amounts of the starting components, e.g. 3-(3,5-ditert-butyl-4-hydroxyphenyl) propanoic alcohol to the linker molecule (e.g., cyanuric chloride), in toluene at 70-110° C.

In yet other embodiment of the present invention is directed to combining 3:1 molar amounts of the starting components, e.g. N-phenyl-1,4-phenylene-diamine to the linker molecule (e.g., cyanuric chloride), in toluene at 0-5° C.

In yet other embodiment of the present invention is directed to combining 3:1 molar amounts of the starting components, e.g. N-phenyl-1,4-phenylene-diamine to the linker molecule (e.g., cyanuric chloride), in toluene at 40-65° C.

In yet another embodiment of the present invention is directed to combining 3:1 molar amounts of the starting components, e.g. N-phenyl-1,4-phenylene-diamine to the linker molecule (e.g., cyanuric chloride), in toluene at 70-110° C.

One embodiment of the present invention is directed to combining 3:1 molar amounts of the starting components, e.g. N$^1$-isopropyl-N$^4$-phenylbenzene-1,4-diamine, N$^1$-(1,3-dimethylbutyl)-N$^4$-phenylbenzene-1,4-diamine, N$^1$-(1,4-dimethylpentyl)-N$^4$-phenylbenzene-1,4-diamine and N-sec-octyl-N$^1$-phenyl-p-phenylenediamine to the linker molecule (e.g., cyanuric chloride), in toluene at 0-5° C., 40-65° C. and 70-110° C. separately.

One embodiment of the present invention is directed to combining 1:1 molar amounts of the starting components, e.g. 3-(3,5-ditert-butyl-4-hydroxyphenyl) propanoic alcohol to the linker molecule (e.g., cyanuric chloride), in toluene at 0-5° C.

In yet other embodiment of the present invention is directed to combining 2:1 molar amounts of the starting components, e.g. N-phenyl-1,4-phenylene-diamine to the linker molecule (e.g., cyanuric chloride), in toluene at 40-65° C.

In yet another embodiment of the present invention is directed to combining 2:1 molar amounts of the starting components, e.g. N-phenyl-1,4-phenylene-diamine to the linker molecule (e.g., cyanuric chloride), in toluene at 70-110° C.

One embodiment of the present invention is directed to combining 1:1 molar amounts of the starting components, e.g. 3-(3,5-ditert-butyl-4-hydroxyphenyl) propanoic alcohol to the linker molecule (e.g., cyanuric chloride), in toluene at 0-5° C.

In yet another embodiment of the present invention is directed to combining 2:1 molar amounts of the starting components, e.g. $N^1$-isopropyl-$N^4$-phenylbenzene-1,4-diamine, $N^1$-(1,3-dimethylbutyl)-$N^4$-phenylbenzene-1,4-diamine, $N^1$-(1,4-dimethylpentyl)-$N^4$-phenylbenzene-1,4-diamine and N-sec-octyl-N'-phenyl-p-phenylenediamine to the linker molecule (e.g., cyanuric chloride), in toluene at 40-65° C. and 70-110° C. separately.

One embodiment of the present invention, wherein linker and phenol derivative are first combined in 1:1 or 1:2 or 1:3 molar ratios and the combination is refluxed between 0 and 110° C. It is then followed by further addition of amine to the reaction in 0 or 1 or 2 molar ratio to the linker and refluxed further to complete the reaction.

In other embodiment, wherein linker and amine are first combined in 1:1 or 1:2 or 1:3 molar ratios and the combination is refluxed between 110° C. It is then followed by further addition of phenol derivative to the reaction in 0 or 1 or 2 molar ratio to the linker and refluxed further to complete the reaction.

One embodiment of the present invention is directed to combining 1:1 or 2:1 or 3:1 or 4; 1 molar amounts of the starting components, e.g. 3-(3,5-ditert-butyl-4-hydroxyphenyl) propanoic alcohol and/or amine to the linker molecule, in toluene and refluxing the reaction mixture at, e.g., 110° C.

In yet other embodiment of the present invention is directed to combining 3:1 molar amounts of the starting components, e.g. 3-(3,5-ditert-butyl-4-hydroxyphenyl) propanoic alcohol to the linker molecule (e.g., 1,2,3-Trichloro-propane), in toluene at 0-5° C.

In yet another embodiment of the present invention is directed to combining 3:1 molar amounts of the starting components, e.g. 3-(3,5-ditert-butyl-4-hydroxyphenyl) propanoic alcohol to the linker molecule (e.g., 1,2,3-Trichloro-propane), in toluene at 70-110° C.

In yet other embodiment of the present invention is directed to combining 3:1 molar amounts of the starting components, e.g. N-phenyl-1,4-phenylene-diamine to the linker molecule (e.g., 1,2,3-Trichloro-propane), in toluene at 0-5° C.

In yet another embodiment of the present invention is directed to combining 3:1 molar amounts of the starting components, e.g. N-phenyl-1,4-phenylene-diamine to the linker molecule (e.g., 1,2,3-Trichloro-propane), in toluene at 70-110° C.

One embodiment of the present invention is directed to combining 3:1 molar amounts of the starting components, e.g. $N^1$-isopropyl-$N^4$-phenylbenzene-1,4-diamine, $N^1$-(1,3-dimethylbutyl)-$N^4$-phenylbenzene-1,4-diamine, $N^1$-(1,4-dimethylpentyl)-$N^4$-phenylbenzene-1,4-diamine and N-sec-octyl-N'-phenyl-p-phenylenediamine to the linker molecule (e.g., 1,2,3-Trichloro-propane), in toluene at 0-5° C. and 70-110° C. separately.

One embodiment of the present invention is directed to combining 2:1 molar amounts of the starting components, e.g. 3-(3,5-ditert-butyl-4-hydroxyphenyl) propanoic alcohol to the linker molecule (e.g., 1,2,3-Trichloro-propane), in toluene at 0-5° C.

In yet another embodiment of the present invention is directed to combining 1:1 molar amounts of the starting components, e.g. N-phenyl-1,4-phenylene-diamine to the linker molecule (e.g., 1,2,3-Trichloro-propane), in toluene at 70-110° C.

One embodiment of the present invention is directed to combining 2:1 molar amounts of the starting components, e.g. 3-(3,5-ditert-butyl-4-hydroxyphenyl) propanoic alcohol to the linker molecule (e.g., 1,2,3-Trichloro-propane), in toluene at 0-5° C.

In yet another embodiment of the present invention is directed to combining 1:1 molar amounts of the starting components, e.g. $N^1$-isopropyl-$N^4$-phenylbenzene-1,4-diamine, $N^1$-(1,3-dimethylbutyl)-$N^4$-phenylbenzene-1,4-diamine, $N^1$-(1,4-dimethylpentyl)-$N^4$-phenylbenzene-1,4-diamine and N-sec-octyl-N'-phenyl-p-phenylenediamine to the linker molecule (e.g., 1,2,3-Trichloro-propane), in toluene at 40-65° C. and 70-110° C. separately.

The antioxidant compounds of the present invention can be employed to inhibit the oxidation of an oxidizable material, for example by contacting the material with an antioxidant compound made by the methods of the present invention.

For purposes of the present invention, a method of "inhibiting oxidation" is a method that inhibits the propagation of a free radical-mediated process. Free radicals can be generated by heat, light, ionizing radiation, metal ions and some proteins and enzymes. Inhibiting oxidation also includes inhibiting reactions caused by the presence of oxygen, ozone or another compound capable of generating these gases or reactive equivalents of these gases.

As used herein the term "oxidizable material" is any material which is subject to oxidation by free-radicals or oxidative reaction caused by the presence of oxygen, ozone or another compound capable of generating these gases or reactive equivalents thereof. In particular the oxidizable material is a lubricant or a mixture of lubricants or fuel (including but not limited to gasoline, kerosene, diesel, biodiesel). The oxidizable material is a polyolefin, polymers, co-polymers, biopolymers, bioplastics, plastics, elastomers, thermoplastics polymers, polyamides, and blends thereof.

The shelf life of many materials and substances contained within the materials, such as packaging materials, are enhanced by the presence of the antioxidants of the present invention. The addition of an antioxidant of the present invention to a packaging material is believed to provide additional protection to the product contained inside the package. In addition, the properties of many packaging materials themselves, particularly polymers, are enhanced by the presence of an antioxidant regardless of the application (i.e., not limited to use in packaging). Common examples of packaging materials include paper, cardboard and various plastics and polymers. A packaging material can be coated with an antioxidant (e.g., by spraying the antioxidant or by applying as a thin film coating), blended with or mixed with an antioxidant, or otherwise have an antioxidant present within it. In one example, a thermoplastic such as polyethylene, polypropylene or polystyrene can be melted in the presence of an antioxidant in order to minimize its degradation during the polymer processing.

The lifetime of fuels (including but not limited to gasoline, kerosene, diesel, and biodiesel), lubricants, lubricant oils, mixtures thereof and compositions comprising lubricants and lubricant oils in general can be improved by contacting the lubricant, lubricant oil, mixtures thereof or composition comprising the lubricant or lubricant oil or mixtures thereof with compounds of the present invention, as described herein.

As used here, the terms "lubricants" and "lubricant oils" can be used interchangeably. Examples of lubricants suitable for use in the compositions and methods of the present invention include, but are not limited to: i) petroleum based oils (Group I, II and III), ii) synthetic oils (Group IV, V) and iii) biolubricant oils (vegetable oils such as canola, soybean, high oleic canola, high oleic soybean oil, corn oil etc.). Group I oils, as defined herein are solvent refined base oils. Group II oils, as defined herein are modern conventional base oils made by hydrocracking and early wax isomerization, or hydroisomerization technologies and have significantly lower levels of impurities than Group I oils. Group III oils, as defined herein are unconventional base oils. Groups I-III differ in impurities, and viscosity index as is shown in Kramer et al. "The Evolution of Base Oil Technology" Turbine Lubrication in the 21$^{st}$ Century ASTM STP #1407 W. R. Herguth and T. M. Wayne, Eds., American Society for Testing and Materials, West Conshohocken, Pa., 2001 the entire contents of which are incorporated herein by reference. Group IV oils as defined herein are "synthetic" lubricant oils, including for example, poly-alpha olefins (PAOs). Biolubricants as defined herein are lubricants which contain at least 51% biomaterial (see Scott Fields, Environmental Health Perspectives, volume 111, number 12, September 2003, the entire contents of which are incorporated herein by reference). Other examples of lubricant oils can be found in Melvyn F. Askew "Biolubricants-Market Data Sheet" IENICA, August 2004 (as part of the IENICA work stream of the IENICA-INFORRM project); Taylor et al. "Engine lubricant Trends Since 1990" paper accepted for publication in the Proceedings I. Mech. E. Part J, Journal of Engineering Tribology, 2005 (Vol. 219 p 1-16); and Desplanches et al. "Formulating Tomorrow's Lubricants" page 49-52 of The Paths to Sustainable Development, part of special report published in October 2003 by Total; the entire contents of each of which are incorporated herein by reference. Biolubricants are often but not necessarily, based on vegetable oils. Vegetable derived, for example, from rapeseed, sunflower, palm and coconut can be used as biolubricants. They can also be synthetic esters which may be partly derived from renewable resources. They can be made from a wider variety of natural sources including solid fats and low grade or waste materials such as tallows. Biolubricants in general offer rapid biodegradability and low environmental toxicity.

As used herein, Group I, II and III oils are petroleum base stock oil. The petroleum industry differentiates their oil based on viscosity index and groups them as Group I, II and III. The synthetic oils are Group IV and Group V. In certain embodiments, synthetic oils are polyesters for example diesters, polyesters such as neopentyl glycols (NPGs), trimethylolpropanes (TMPs), penterythritols (PEs), and dipentaerythritols (DiPEs). In other embodiments, synthetic oils include monoesters and trimellitates. In other embodiments, synthetic oils include polyalkylene glycols (PAGs). In certain embodiments of the present invention, 50% to 20% by weight of the antioxidants of the present invention are added to lubricant oils. In certain other embodiments of the present invention, 10% to 5% by weight of the antioxidants of the present invention are added to lubricant oils. In certain other embodiments of the present invention, 0.1% to 2% by weight of the antioxidants of the present invention are added to lubricant oils. In certain other embodiments of the present invention, 0.001% to 0.5% by weight of the anti-oxidants of the present invention is added to lubricant oils. This percentage varies depending upon their end application and type of the base oil.

In certain embodiments of the present invention the antioxidants of the present invention are usually added to lubricant oils with stirring at between 0 and 100° C., between 20 and 80° C. or between 40-60° C.

In certain embodiments of the present invention the antioxidants of the present invention are usually added to lubricant and fuel oils (based on petroleum, synthetic, and/or bio-based oils) used in automotives and industrial applications such as but not limited to transmission fluid, engine oil, break oil, metal working fluids, greases, gear oils.

In certain embodiments, the mixture of antioxidants of the present invention is preferred due to improved solubility characteristics as compared to a single component antioxidant.

In yet other embodiments of the present invention the antioxidants of the present invention are usually added to lubricant and fuel oils along with other additional lubricant additives including but not limited to anti-corrosion, anti-foaming, viscosity modifier, pour point depressants, and other phenolic and aminic antioxidants.

In one embodiment, the present invention is a composition comprising present invention antioxidant, and at least one additive selected from the group consisting of i) a surface additive; ii) a performance enhancing additive; and iii) a lubricant protective additive.

In another embodiments the present invention is a lubricant composition comprising: a lubricant or a mixture of lubricants, a present invention antioxidant and at least one additive selected from the group consisting of i) a surface additive; ii) a performance enhancing additive; and iii) a lubricant protective additive.

In yet another embodiment the present invention is a method of improving a composition comprising combining the composition with present invention antioxidant; and at least one additive selected from the group consisting of i) a surface additive; ii) a performance enhancing additive; and iii) a lubricant protective additive.

In yet another embodiment the present invention is a method of improving a lubricant or a mixture of lubricants comprising combining the lubricant or mixture of lubricants with present invention antioxidant; and at least one additive selected from the group consisting of i) a surface additive; ii) a performance enhancing additive; and iii) a lubricant protective additive.

The compositions and methods of the present invention generally provide increased shelf life, increased oxidative resistance, enhanced performance and/or improved quality to materials, such as, for example, lubricants and lubricant oils and fuels. In general it is believed that because of the synergy of the antioxidants with the additives, the compositions described herein have superior oxidation resistance. The additives exhibit several key functions such as corrosion inhibition, detergency, viscosity modification, antiwear performance, dispersant properties, cleaning and suspending ability. The disclosed compositions, in general provide superior performance of lubricants in high temperatures applications due to the presence of antioxidants which are thermally stable at high temperatures with enhanced oxidation resistance.

Stabilized Lubricant Oil Compositions

Lubricants, lubricant oils, mixtures thereof and compositions comprising lubricants and lubricant oils can be improved by the methods of the present invention, by contacting the lubricant, lubricant oil, mixtures thereof or composition comprising the lubricant or lubricant oil or mixtures thereof with antioxidants, additives and mixtures thereof as described herein.

As used here, the terms "lubricants" and "lubricant oils" can be used interchangeably. Examples of lubricants suitable for use in the compositions and methods of the present invention include, but are not limited to: i) petroleum based oils (Group I, II and III), ii) synthetic oils (Group IV and V)) and iii) biolubricant oils (vegetable oils such as canola, soybean, corn oil etc.). Group I oils, as defined herein are solvent refined base oils. Group II oils, as defined herein are modern conventional base oils made by hydrocracking and early wax isomerization, or hydroisomerization technologies and have significantly lower levels of impurities than Group I oils. Group III oils, as defined herein are unconventional base oils. Groups I-III differ in impurities, and viscosity index as is shown in Kramer et al. "The Evolution of Base Oil Technology" *Turbine Lubrication in the 21$^{st}$ Century* ASTM STP #1407 W. R. Herguth and T. M. Wayne, Eds., American Society for Testing and Materials, West Conshohocken, Pa., 2001 the entire contents of which are incorporated herein by reference. Group IV oils as defined herein are "synthetic" lubricant oils, including for example, poly-alpha olefins (PAOs). Biolubricants as defined herein are lubricants which contain at least 51% biomaterial (see Scott Fields, Environmental Health Perspectives, volume 111, number 12, September 2003, the entire contents of which are incorporated herein by reference). Other examples of lubricant oils can be found in Melvyn F. Askew "Biolubricants-Market Data Sheet" IENICA, August 2004 (as part of the IENICA work stream of the IENICA-INFORRM project); Taylor et al. "Engine lubricant Trends Since 1990" paper accepted for publication in the Proceedings I. Mech. E. Part J, Journal of Engineering Tribology, 2005 (Vol. 219 p 1-16); and Desplanches et al. "Formulating Tomorrow's Lubricants" page 49-52 of The Paths to Sustainable Development, part of special report published in October 2003 by Total; the entire contents of each of which are incorporated herein by reference. Biolubricants are often but not necessarily, based on vegetable oils. Vegetable derived, for example, from rapeseed, sunflower, palm and coconut can be used as biolubricants. They can also be synthetic esters which may be partly derived from renewable resources. They can be made from a wider variety of natural sources including solid fats and low grade or waste materials such as tallows. Biolubricants in general offer rapid biodegradability and low environmental toxicity.

Additives

Examples of first additives suitable for use in the compositions and methods of the present invention include but are not limited to, surface additives, performance enhancing additives and lubricant protective additives.

Surface additives: In certain embodiments of the present invention, surface additives can protect the surfaces that are lubricated from wear, corrosion, rust, and frictions. Examples of these surface additives suitable for use in the compositions and methods of the present invention include, but are not limited to: (a) rust inhibitors, (b) corrosion inhibitors, (c) extreme pressure agents, (d) tackiness agents, (e) antiwear agents, (f) detergents and dispersants, (g) compounded oil (like fat or vegetable oil to reduce the coefficient of friction without affecting the viscosity), (h) antimisting, (i) seal swelling agents and (j) biocides.

Performance Enhancing Additives: In certain embodiments of the present invention, performance enhancing additives improve the performance of lubricants. Examples of these performance enhancing additives suitable for use in the Compositions and methods of the present invention include, but are not limited to: (a) pour-point depressants, (b) viscosity index modifiers (c) emulsifiers, and (d) demulsifiers.

Lubricant Protective Additives: In certain embodiments of the present invention, lubricant protective additives maintain the quality of oil from oxidation and other thermal degradation processes. Examples of these lubricant protective additives suitable for use in the compositions and methods of the present invention include, but are not limited to: (a) oxidation inhibitors and (b) foam inhibitors.

Other Lubricant Additives

In certain embodiments, a second additive can be used in the compositions and methods of the present invention in combination with the first antioxidant and the first additive as described above. Examples of second additives suitable for use in the compositions and methods of the present invention include, include but are not limited to, for example, dispersants, detergents, corrosion inhibitors, rust inhibitors, metal deactivators, antiwear and extreme pressure agents, antifoam agents, friction modifiers, seal swell agents, demulsifiers, viscosity index improvers, pour point depressants, and the like. See, for example, U.S. Pat. No. 5,498,809 for a description of useful lubricating oil composition additives, the disclosure of which is incorporated herein by reference in its entirety.

Dispersants: Examples of dispersants suitable for use in the compositions and methods of the present invention include, but are not limited to: polybutenylsuccinic acid-amides, -imides, or -esters, polybutenylphosphonic acid derivatives, Mannich Base ashless dispersants, and the like.

Detergents: Examples of detergents suitable for use in the compositions and methods of the present invention include, but are not limited to: metallic phenolates, metallic sulfonates, metallic salicylates, metallic phosphonates, metallic thiophosphonates, metallic thiopyrophosphonates, and the like.

Corrosion Inhibitors: Examples of corrosion inhibitors suitable for use in the compositions and methods of the present invention include, but are not limited to: phosphosulfurized hydrocarbons and their reaction products with an alkaline earth metal oxide or hydroxide, hydrocarbyl-thio-substituted derivatives of 1,3,4-thiadiazole, thiadiazole polysulphides and their derivatives and polymers thereof, thio and polythio sulphenamides of thiadiazoles such as those described in U.K. Patent Specification 1,560,830, and the like.

Rust Inhibitors: Examples of rust inhibitors suitable for use in the compositions and methods of the present invention include, but are not limited to: nonionic surfactants such as polyoxyalkylene polyols and esters thereof, anionic surfactants such as salts of alkyl sulfonic acids, and other compounds such as alkoxylated fatty amines, amides, alcohols and the like, including alkoxylated fatty acid derivatives treated with C9 to C16 alkyl-substituted phenols (such as the mono- and di-heptyl, octyl, nonyl, decyl, undecyl, dodecyl and tridecyl phenols).

Metal Deactivators: Metal deactivators as used herein, are the additives which form an inactive film on metal surfaces by complexing with metallic ions and reducing, for example, the catalytic effect on metal gum formation and other oxidation. Examples of metal deactivators suitable for use in the compositions and methods of the present invention include, but are not limited to: N,N-disubstituted aminomethyl-1,2,4-triazoles, N,N-disubstituted aminomethyl-benzotriazoles, mixtures thereof, and the like.

Antiwear and Extreme Pressure Additives: Antiwear and extreme pressure additives, as used herein, react with metal surfaces to form a layer with lower shear strength then metal, thereby preventing metal to metal contact and reducing friction and wear. Examples of antiwear additives suitable for use in the compositions and methods of the present invention include, but are not limited to: sulfurized olefins, sulfurized esters, sulfurized animal and vegetable oils, phosphate esters, organophosphites, dialkyl alkylphosphonates, acid phosphates, zinc dialkyldithiophosphates, zinc diaryldithiophosphates, organic dithiophosphates, organic phosphorothiolates, organic thiophosphates, organic dithiocarbamates, dimercaptothiadiazole derivatives, mercaptobenzothiazole derivatives, amine phosphates, amine thiophosphates, amine dithiophosphates, organic borates, chlorinated paraffins, and the like.

Antifoam Agents: Examples of antifoam agents suitable for use in the compositions and methods of the present invention include, but are not limited to: polysiloxanes and the like.

Friction Modifiers: Examples of friction modifiers suitable for use in the compositions and methods of the present invention include, but are not limited to: fatty acid esters and amides, organic molybdenum compounds, molybdenum dialkylthiocarbamates, molybdenum dialkyl dithiophosphates, molybdenum dithiolates, copper oleate, copper salicylate, copper dialkyldithiophosphates, molybdenum disulfide, graphite, polytetrafluoroethylene, and the like.

Seal Swell Agents: Seal swell agents, as used herein, react chemically with elastomers to cause slight swell thus improving low temperature performance especially in, for example, aircraft hydraulic oil. Examples of seal swell agents suitable for use in the compositions and methods of the present invention include, but are not limited to: dioctyl sebacate, dioctyl adipate, dialkyl phthalates, and the like.

Demulsifiers: Demulsifiers, as used herein promote separation of oil and water in lubricants exposed to water. Examples of demulsifiers suitable for use in the compositions and methods of the present invention include, but are not limited to: the esters described in U.S. Pat. Nos. 3,098,827 and 2,674,619 incorporated herein by reference.

Viscosity Index Improvers: Examples of viscosity index improvers suitable for use in the compositions and methods of the present invention include, but are not limited to: olefin copolymers, dispersant olefin copolymers, polymethacrylates, vinylpyrrolidone/methacrylate-copolymers, polyvinylpyrrolidones, polybutanes, styrene/-acrylate-copolymers, polyethers, and the like.

Pour Point Depressants: Pour point depressants as used herein reduce the size and cohesiveness of crystal structure resulting in low pour point and increased flow at low-temperatures. Examples of pour point depressants suitable for use in the compositions and methods of the present invention include, but are not limited to: polymethacrylates, alkylated naphthalene derivatives, and the like.

Other Antioxidants and Stabilizers

In certain embodiments, a second antioxidant or a stabilizer can be used in the compositions and methods of the present invention in combination with the first antioxidant and the first additive and optionally the second additive as described above. Examples of second antioxidants suitable for use in the compositions and methods of the present invention include, include but are not limited to:

1. Amine Antioxidants
1.1. Alkylated Diphenylamines, for example octylated diphenylamine; styrenated diphenylamine; mixtures of mono- and dialkylated tert-butyl-tert-octyldiphenylamines; and 4,4'-dicumyldiphenylamine.
1.2. Phenyl Naphthylamines, for example N-phenyl-1-naphthylamine; N-phenyl-2-naphthylamine; tert-octylated N-phenyl-1-naphthylamine.
1.3. Derivatives of para-Phenylenediamine, for example N,N'-diisopropyl-p-phenylenediamine; N,N'-di-sec-butyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N,N'-diphenyl-p-phenylenediamine; N,N'-di-(naphthyl-2)-p-phenylenediamine; N-isopropyl-N'-phenyl-p-phenylenediamine; N-(1,3-dimethylbutyl)-N'-phenyl-p-phenylenediamine; N-(1-methylheptyl)-N'-phenyl-p-phenylenediamine; N-cyclohexyl-N'-phenyl-p-phenylenediamine; N,N'-dimethyl-N,N'-di-sec-butyl-p-phenylenediamine.
1.4. Phenothiazines, for example phenothiazine; 2-methylphenothiazine; 3-octylphenothiazine; 2,8-dimethylphenothiazine; 3,7-dimethylphenothiazine; 3,7-diethylphenothiazine; 3,7-dibutylphenothiazine; 3,7-dioctylphenothiazine; 2,8-dioctylphenothiazine.
1.5. Dihydroquinolines, for example 2,2,4-trimethyl-1,2-dihydroquinoline or a polymer thereof.
2. Phenolic Antioxidants
2.1. Alkylated monophenols, for example 2,6-di-tert-butyl-4-methylphenol; 2,6-di-tert-butylphenol; 2-tert-butyl-4,6-dimethylphenol; 2,6-di-tert-butyl-4-ethylphenol; 2,6-di-tert-butyl-4-n-butylphenol; 2,6-di-tert-butyl-4-isobutylphenol; 2,6-di-tert-butyl-4-sec-butylphenol; 2,6-di-tert-butyl-4-octadecylphenol; 2,6-di-tert-butyl-4-nonylphenol; 2,6-dicyclopentyl-4-methylphenol; 2-(β-methylcyclohexyl)-4,6-dimethylphenol; 2,6-dioctadecyl-4-methylphenol; 2,4,6-tricyclohexylphenol; 2,6-di-tert-butyl-4-methoxymethylphenol; 2,6-di-tert-butyl-4-dimethylaminomethylphenol; o-tert-butylphenol.
2.2. Alkylated hydroquinones, for example 2,6-di-tert-butyl-4-methoxyphenol; 2,5-di-tert-butylhydroquinone; 2,5-di-tert-amylhydroquinone; 2,6-di-phenyl-4-octadecyloxyphenol.
2.3. Hydroxylated thiodiphenyl ethers, for example 2,2'-thiobis(6-tert-butyl-4-methyl-phenol); 2,2'-thiobis(4-octylphenol); 4,4'-thiobis(6-tert-butyl-3-methylphenol); 4,4'-thiobis(6-tert-butyl-2-methylphenol).
2.4. Alkylidenebisphenols, for example 2,2'-methylenebis(6-tert-butyl-4-methylphenol); 2,2'-methylenebis(6-tert-butyl-4-ethylphenol); 2,2'-methylenebis(4-methyl-6-(α-methylcyclohexyl)phenol); 2,2'-methylenebis(4-methyl-6-cyclohexylphenol); 2,2'-methylenebis(6-nonyl-4-methylphenol); 2,2'-methylenebis(4,6-di-tert-butylphenol); 2,2'-ethylidenebis(6-tert-butyl-4-isobutylphenol); 2,2'-methylenebis[6-□-methylbenzyl)-4-nonylphenol]; 2,2'-methylenebis[6-(a, a-dimethylbenzyl)-4-nonylphenol]; 4,4'-methylenebis(2,6-di-tert-butylphenol); 4,4'-methylenebis(6-tert-butyl-2-methylphenol); 1,1-bis(5-tert-butyl-4-hydroxy-2-methylphenyl)butane; 2,6-di(3-tert-butyl-5-methyl-2-hydroxybenzyl)-4-methylphenol; 1,1,3-tris(5-tert-butyl-4-hydroxy-2-methylphenyl)-3-n-dodecylmercaptobutane; ethylene glycol bis[3,3-bis(3'-tert-butyl-4'-hydroxylphenyl)butyrate]; di(3-tert-butyl-4-hydroxy-5-methylphenyl)dicyclopentadiene; di[2-(3'-tert-butyl-2'-hydroxy-5'-methylbenzyl)-6-tert-butyl-4-methylphenyl]terephthalate.
2.5. Benzyl compounds, for example 1,3,5-tris(3,5-di-tert-butyl-4-hydroxybenzyl)-2,4,6-trimethylbenzene; di(3,5-di-tert-butyl-4-hydroxybenzyl)sulfide; 3,5-di-tert-butyl- 4-hydroxybenzylmercaptoacetic acid isooctyl ester; bis (4-tert-butyl-3-hydroxy-2,6-dimethyl-benzyl)dithi- oterephthalate; 1,3,5-tris(3,5-di-tert-butyl-4-hydroxybenzyl) isocyanurate; 1,3,5-tris(4-tert-butyl-3-hydroxy-2,6-dimethylbenzyl)isocyanurate; 3,5-di-tert-butyl-4-hydroxy-benzylphosphonic acid dioctadecyl ester; 3,5-di-tert-butyl-4-hydroxybenzylphosphonic acid mono-ethyl ester calcium salt.

2.6. Acylaminophenols, for example 4-hydroxylauric acid anilide; 4-hydroxystearic acid anilide; 2,4-bis-octylmercapto-6-(3,5-di-tert-butyl-4-hydroxyaniline)-s-triazine; N-(3,5-di-tert-butyl-4-hydroxyphenyl)carbamic acid octyl ester.

2.7. Esters of β-(3,5-di-tert-butyl-4-hydroxyphenyl)propionic acid with mono- or polyhydric alcohols, e.g. with methanol; octadecanol; 1,6-hexanediol; neopentyl glycol; thiodiethylene glycol; diethylene glycol; triethylene glycol; pentaerythritol; tris(hydroxyethyl)isocyanurate; and di(hydroxyethyl)oxalic acid diamide.

2.8. Esters of β-(5-tert-butyl-4-hydroxy-3-methylphenyl) propionic acid with mono- or polyhydric alcohols, e.g. with methanol; octadecanol; 1,6-hexanediol; neopentyl glycol; thiodiethylene glycol; diethylene glycol; triethylene glycol; pentaerythritol; tris(hydroxyethyl)isocyanurate; and di(hydroxyethyl)oxalic acid diamide.

2.9. Amides of β-(3,5-di-tert-butyl-4-hydroxyphenyl)propionic acid, e.g., N,N'-di(3,5-di-tert-butyl-4-hydroxyphenyl-propionyl)hexamethylenediamine; N,N'-di(3,5-di-tert-butyl-4-hydroxyphenylpropionyl)trimethylenediamine; N,N'-di-(3,5-di-tert-butyl-4-hydroxyphenylpropionyl)hydrazine.

3. Sulfurized organic compounds, for example aromatic, alkyl, or alkenyl sulfides and polysulfines; sulfurized olefins; sulfurized fatty acid esters; sulfurized ester olefins; sulfurized oils; esters of β-thiodipropionic acid; sulfurized Diels-Alder adducts; sulfurized terpene compounds; and mixtures thereof.

4. Organo-borate compounds, for example alkyl- and aryl- (and mixed alkyl, aryl) substituted borates.

5. Phosphite and phosphate antioxidants, for example alkyl- and aryl- (and mixed alkyl, aryl) substituted phosphites, and alkyl- and aryl- (and mixed alkyl, aryl) substituted dithiophosphates such as O,O,S-trialkyl dithiophosphates, O,O,S-triaryldithiophosphates and dithiophosphates having mixed substitution by alkyl and aryl groups, phosphorothionyl sulfide, phosphorus-containing silane, polyphenylene sulfide, amine salts of phosphinic acid and quinone phosphates.

6. Copper compounds, for example copper dihydrocarbyl thio- or dithiophosphates, copper salts of synthetic or natural carboxylic acids, copper salts of alkenyl carboxylic acids or anhydrides such as succinic acids or anhydrides, copper dithiocarbamates, copper sulphonates, phenates, and acetylacetonates. The copper may be in cuprous (Cu) or cupric ($Cu^{II}$) form.

7. Zinc dithiodiphosphates, for example zinc dialkyldithiophosphates, diphenyldialkyldithiophosphates, and di(alkylphenyl)dithiophosphates.

In one embodiment, the compositions for use in the methods of the present invention, include but are not limited to:

a. a first antioxidant (in the concentration range, from about 0.0001% to about 50%, from about 0.0005% to about 20%, from about 0.005% to about 10%, from about 0.05% to about 5% or from about 0.01% to about 1%) with a first additive selected from the group comprising a surface additive, a performance enhancing additive and a lubricant performance additive, for example, in amounts of from about 0.0005% to about 50%, from about 0.0001% to about 20%, from about 0.005% to about 10%, from about 0.05% to about 5% or from about 0.01% to about 1% by weight, based on the weight of lubricant to be stabilized.

b. the first antioxidant and the first additive as described in a. and a second additive, for example, in concentrations of from about 0.0001% to about 50% by weight, about 0.0005% to about 20% by weight, about 0.001% to about 10% by weight, from about 0.01% to about 5% by weight, from about 0.05% to about 1% by weight from about 0.1% to about 1% by weight based on the overall weight of the lubricant to be stabilized.

c. the first antioxidant and the first additive as described in a. and optionally the second additive as described in b. and a second antioxidant, for example, Irganox® L 57, Irganox® 1010, Irganox® 1330, Irganox® 1076, Irganox® 5057 and Irganox® L 135 in the concentration range, from about 0.0001% to about 50%, from about 0.0005% to about 20%, from about 0.005% to about 10%, from about 0.05% to about 5% or from about 0.01% to about 1%) by weight, based on the weight of lubricant to be stabilized.

In yet another embodiment, the antioxidant compositions for use in the methods of the present invention, includes but is not limited to: the first antioxidant from the present invention and the second antioxidant from the section 'OTHER ANTIOXIDANTS AND STABILIZERS'. The antioxidant composition, where in the weight ratio of the second antioxidant to the first antioxidant of the present invention is from about 1:99 to 99:1, from about 10:90, 20:80, 30:70, 40:60, 50:50, 60:40, 70:30, 80:20, 90:10. The second antioxidant second antioxidant, for example, Irganox® L 57, Irganox® L64, Irganox® 1330, Irganox® 1076, Irganox® 5057 and Irganox® L 135.

The term "alkyl" as used herein means a saturated straight-chain, branched or cyclic hydrocarbon. When straight-chained or branched, an alkyl group is typically C1-C8, more typically C1-C6; when cyclic, an alkyl group is typically C3-C12, more typically C3-C7 alkyl ester. Examples of alkyl groups include methyl, ethyl, n-propyl, iso-propyl, n-butyl, sec-butyl and tert-butyl and 1, 1-dimethylhexyl.

The term "alkoxy" as used herein is represented by —OR, wherein R is an alkyl group as defined above.

The term "carbonyl" as used herein is represented by —C(=O)R, wherein R is an alkyl group as defined above.

The term "alkoxycarbonyl" as used herein is represented by —C(=O)OR, wherein R is an alkyl group as defined above.

The term "aromatic group" includes carbocyclic aromatic rings and heteroaryl rings. The term "aromatic group" may be used interchangeably with the terms "aryl", "aryl ring" "aromatic ring", "aryl group" and "aromatic group".

Carbocyclic aromatic ring groups have only carbon ring atoms (typically six to fourteen) and include monocyclic aromatic rings such as phenyl and fused polycyclic aromatic ring systems in which a carbocyclic aromatic ring is fused to one or more aromatic rings (carbocyclic aromatic or heteroaromatic)r. Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The term "heteroaryl", "heteroaromatic", "heteroaryl ring", "heteroaryl group" and "heteroaromatic group", used alone or as part of a larger moiety as in "heteroaralkyl" refers to heteroaromatic ring groups having five to fourteen members, including monocyclic heteroaromatic rings and polycyclic aromatic rings in which a monocyclic aromatic ring is fused to one or more other aromatic ring (carbocyclic or heterocyclic). Heteroaryl groups have one or more ring heteroatoms. Examples of heteroaryl groups include 2-furanyl, 3-furanyl, N-imidazolyl, 2-imidazolyl, 4-imidazolyl, 5-imidazolyl, 3-isoxazolyl, 4-isoxazolyl, 5-isoxazolyl, oxadiazolyl, oxadiazolyl, 2-oxazolyl, 4-oxazolyl, 5-oxazolyl, N-pyrazolyl, 3-pyrazolyl, 4-pyrazolyl, 5-pyrazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-thiazolyl, 4-thiazolyl, 5-thiazolyl, triazolyl, tetrazolyl, 2-thienyl, 3-thienyl, carbazolyl, benzothienyl, benzofuranyl, indolyl, quinolinyl, benzothiazole, benzooxazole, benzimidazolyl, isoquinolinyl and isoindolyl. Also included within the scope of the term "heteroaryl", as it is used herein, is a group in which an aromatic ring is fused to one or more non-aromatic rings (carbocyclic or heterocyclic), where the radical or point of attachment is on the aromatic ring.

The term non-aromatic heterocyclic group used alone or as part of a larger moiety refers to non-aromatic heterocyclic ring groups having three to fourteen members, including monocyclic heterocyclic rings and polycyclic rings in which a monocyclic ring is fused to one or more other non-aromatic carbocyclic or heterocyclic ring or aromatic ring (carbocyclic or heterocyclic). Heterocyclic groups have one or more ring heteroatoms, and can be saturated or unsaturated. Examples of heterocyclic groups include piperidinyl, piperizinyl, pyrrolidinyl, pyrazolidinyl, imidazolidinyl, tetrahydroquinolinyl, indolinyl, isoindolinyl, tetrahydrofuranyl, oxazolidinyl, thiazolidinyl, dioxolanyl, dithiolanyl, tetrahydropyranyl, dihydropyranyl, azepanyl and azetidinyl.

The term "heteroatom" means nitrogen, oxygen, or sulfur and includes any oxidized form of nitrogen and sulfur, and the quaternized form of any basic nitrogen. Also the term "nitrogen" includes substitutable nitrogen of a heteroaryl or non-aromatic heterocyclic group. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR" (as in N-substituted pyrrolidinyl), wherein R" is a suitable substituent for the nitrogen atom in the ring of a non-aromatic nitrogen-containing heterocyclic group, as defined below.

As used herein the term non-aromatic carbocyclic ring as used alone or as part of a larger moiety refers to a non-aromatic carbon containing ring which can be saturated or unsaturated having three to fourteen atoms including monocyclic and polycyclic rings in which the carbocyclic ring can be fused to one or more non-aromatic carbocyclic or heterocyclic rings or one or more aromatic (carbocyclic or heterocyclic) rings.

An optionally substituted aryl group as defined herein may contain one or more substitutable ring atoms, such as carbon or nitrogen ring atoms. Examples of suitable substituents on a substitutable ring carbon atom of an aryl group include halogen (e.g., —Br, Cl, I and F), —OH, C1-C4 alkyl, C1-C4 haloalkyl, —NO$_2$, C1-C4 alkoxy, C1-C4 haloalkoxy, —CN, —NH$_2$, C1-C4 alkylamino, C1-C4 dialkylamino, —C(O)NH$_2$, —C(O)NH(C1-C4 alkyl), —C(O)(C1-C4 alkyl), —OC(O)(C1-C4 alkyl), —OC(O)(aryl), —OC(O)(substituted aryl), —OC(O)(aralkyl), —OC(O)(substituted aralkyl), —NHC(O)H, —NHC(O)(C1-C4 alkyl), —C(O)N(C1-C4 alkyl)$_2$, —NHC(O)O—(C1-C4 alkyl), —C(O)OH, —C(O)O—(C1-C4 alkyl), —NHC(O)NH$_2$, —NHC(O)NH(C1-C4 alkyl), —NHC(O)N(C1-C4 alkyl)$_2$, —NH—C(=NH)NH$_2$, —SO$_2$NH$_2$—SO$_2$NH(C1-C3alkyl), —SO$_2$N(C1-C3alkyl)$_2$, NHSO$_2$H, NHSO$_2$(C1-C4 alkyl) and optionally substituted aryl. Preferred substituents on aryl groups are as defined throughout the specification. In certain embodiments aryl groups are unsubstituted.

Examples of suitable substituents on a substitutable ring nitrogen atom of an aryl group include C1-C4 alkyl, NH$_2$, C1-C4 alkylamino, C1-C4 dialkylamino, —C(O)NH$_2$, —C(O)NH(C1-C4 alkyl), —C(O)(C1-C4 alkyl), —CO$_2$R, —C(O)C(O)R, —C(O)CH$_3$, —C(O)OH, —C(O)O—(C1-C4 alkyl), —SO$_2$NH$_2$—SO$_2$NH(C1-C3alkyl), —SO$_2$N(C1-C3alkyl)$_2$, NHSO$_2$H, NHSO$_2$(C1-C4 alkyl), —C(=S)NH$_2$, —C(=S)NH(C1-C4 alkyl), —C(=S)N(C1-C4 alkyl)$_2$, —C(=NH)—N(H)$_2$, —C(=NH)—NH(C1-C4 alkyl) and —C(=NH)—N(C1-C4 alkyl)$_2$, An optionally substituted alkyl group or non-aromatic carbocyclic or heterocyclic group as defined herein may contain one or more substituents. Examples of suitable substituents for an alkyl group include those listed above for a substitutable carbon of an aryl and the following: =O, =S, =NNHR, =NN(R)$_2$, =NNHC(O)R, =NNHCO$_2$ (alkyl), =NNHSO$_2$ (alkyl), =NR, spiro cycloalkyl group or fused cycloalkyl group. R** in each occurrence, independently is —H or C1-C6 alkyl. Preferred substituents on alkyl groups are as defined throughout the specification. In certain embodiments optionally substituted alkyl groups are unsubstituted.

A "spiro cycloalkyl" group is a cycloalkyl group which shares one ring carbon atom with a carbon atom in an alkylene group or alkyl group, wherein the carbon atom being shared in the alkyl group is not a terminal carbon atom.

Without wishing to be bound by any theory or limited to any mechanism it is believed that macromolecular antioxidants and polymeric macromolecular antioxidants of the present invention exploit the differences in activities (ks, equilibrium constant) of, for example, homo- or hetero-type antioxidant moieties. Antioxidant moieties include, for example, hindered phenolic groups, unhindered phenolic groups, aminic groups and thioester groups, etc. of which there can be one or more present in each macromolecular antioxidant molecule. As used herein a homo-type antioxidant macromolecule comprises antioxidant moieties which are all same, for example, hindered phenolic, —OH groups. As used herein a hetero-type antioxidant macromolecule comprises at least one different type of moiety, for example, hindered phenolic and aminic groups in the one macromolecule.

This difference in activities can be the result of, for example, the substitutions on neighboring carbons or the local chemical or physical environment (for example, due to electrochemical or stereochemical factors) which can be due in part to the macromolecular nature of molecules.

In one embodiment of the present invention, a series of macromolecular antioxidant moieties of the present invention with different chemical structures can be represented by W1H, W2H, W3H, . . . to WnH. In one embodiment of the present invention, two types of antioxidant moieties of the present invention can be represented by: W1H and W2H. In certain embodiments W1H and W2H can have rate constants of k1 and k2 respectively. The reactions involving these moieties and peroxyl radicals can be represented as:

$$\text{ROO.} + \text{W1H} \xrightarrow{k1} \text{ROOH} + \text{W1.} \quad (1)$$

$$\text{ROO.} + \text{W2H} \xrightarrow{k2} \text{ROOH} + \text{W2.} \quad (2)$$

where ROO. is a peroxyl radical resulting from, for example, initiation steps involving oxidation activity, for example:

$$\text{RH} \rightarrow \text{R.} + \text{H.} \quad (3)$$

$$\text{R.} + \text{O}_2 \rightarrow \text{ROO.} \quad (4)$$

In one particular embodiment of the present invention k1>>k2 in equations (1) and (2). As a result, the reactions would take place in such a way that there is a decrease in concentration of W1. free radicals due their participation in the regeneration of active moiety W2H in the molecule according equation (5):

$$\text{W1.} + \text{W2H} \rightarrow \text{W1H} + \text{W2.} \quad (5) \text{ (transfer equilibrium)}$$

This transfer mechanism may take place either in intra- or inter-molecular macromolecules. The transfer mechanism (5) could take place between moieties residing on the same macromolecule (intra-type) or residing on different macromolecules (inter-type).

In certain embodiments of the present invention, the antioxidant properties described immediately above (equation 5) of the macromolecular antioxidants and polymeric macromolecular antioxidants of the present invention result in advantages including, but not limited to:
  a) Consumption of free radicals W1. according to equation (5) can result in a decrease of reactions of W1. with hydroperoxides and hydrocarbons (RH).
  b) The regeneration of W1H provides extended protection of materials. This is a generous benefit to sacrificial type of antioxidants that are used today. Regeneration of W1H assists in combating the oxidation process. The increase in the concentration of antioxidant moieties W1H (according to equation 5) extends the shelf life of materials.

In certain embodiments of the present invention, the following items are of significant interest for enhanced antioxidant activity in the design of the macromolecular antioxidants and polymeric macromolecular antioxidants of the present invention:
  a) The activity of proposed macromolecular antioxidant is dependent on the regeneration of W1H in equation (5) either through inter- or intra-molecular activities involving homo- or hetero-type antioxidant moieties.
  b) Depending on the rates constants of W1H and W2H it is possible to achieve performance enhancements by many multiples and not just incremental improvements.

In certain embodiments of the present invention, more than two types of antioxidant moieties with different rate constants are used in the methods of the present invention.

In certain embodiments, the present invention pertains to the use of the disclosed compositions to improve materials, such as lubricants, lubricant oils, compositions comprising lubricants and lubricant oils and mixtures thereof.

In certain embodiments, as defined herein improving a material means inhibiting oxidation of an oxidizable material.

For purposes of the present invention, a method of "inhibiting oxidation" is a method that inhibits the propagation of a free radical-mediated process. Free radicals can be generated by heat, light, ionizing radiation, metal ions and some proteins and enzymes. Inhibiting oxidation also includes inhibiting reactions caused by the presence of oxygen, ozone or another compound capable of generating these gases or reactive equivalents of these gases.

As used herein the term "oxidizable material" is any material which is subject to oxidation by free-radicals or oxidative reaction caused by the presence of oxygen, ozone or another compound capable of generating these gases or reactive equivalents thereof. In particular the oxidizable material is a lubricant or a mixture of lubricants.

In certain other embodiments, as defined herein improving a material means inhibiting oxidation, as well as improving performance and/or increasing the quality of a material, such as, a lubricant, lubricant oil, composition comprising a lubricant or lubricant oil or mixtures thereof. Increasing the quality of a material includes reducing friction and wear, increasing viscosity, resistance to corrosion, aging or contamination, etc. In certain embodiments, improving means that the lubricant is more resistant to degradation due to the presence of oxygen, temperature, pressure, water, metal species and other contributing factors to degradation. In certain embodiments, additive as described herein help to promote the shelf life of these oils. In certain embodiments the stability of the lubricants is directly related to their performance. That is the lubricant will not perform well if the lubricant has been degraded. In certain embodiments the performance of the lubricants is related to the additives. That is if antioxidant and additives are used they will result in an improvement in the stability and performance of the lubricants.

A lubricant, as defined herein is a substance (usually a liquid) introduced between two moving surfaces to reduce the friction and wear between them. Lubricant can be used in, for example, automotive engines, and hydraulic fluids with transmission oils and the like. In addition to automotive and industrial applications, lubricants are used for many other purposes, including bio-medical applications (e.g. lubricants for artificial joints), grease, aviation lubricants, turbine engine lubricants, compressor oils, power transformer oils, automatic transmission fluids, metal working fluids, gear oils, sexual lubricants and others.

In certain other embodiments of the present invention, lubricants are biolubricants that are used as hydraulic fluid (bio hydraulic fluid), metal working fluid, gear oils (bio-gear oil), elevator oil, transformer oil, tractor oil, marine lubricants, grease, rock drill oil, chain saw bar oil, wire, rope and chain lubricants, stern tube lubricant, penetrating oils, aerosols, functional fluids, environmentally acceptable lubricants (EALs), and many other industrial applications. Usually the base oil of biolubricant is bio-oil, synthetically modified bio-oil, biobased oil, and/or mixture of these bio-oils and biobased oils with other Group I-V oils. Biolubricants are normally biodegradable. Extent of biolubricants biodegradability is dependent on the composition of base oil.

In certain other embodiments, as defined herein improving a material means inhibiting oxidation, as well as improving performance and/or increasing the quality of a material, such as polymers, copolymers and their blends, plastics, elastomers, polyolefins, thermoplastic elastomers, and nylons.

In one embodiment, of the present invention the compositions for use in stabilization of polyolefins, include but are not limited to:
  a. an antioxidant (in the concentration range, from about 0.0001% to about 50%, from about 0.0005% to about 20%, from about 0.005% to about 10%, from about 0.05% to about 5% or from about 0.01% to about 1%) with acid scavengers, for example, in amounts of from about 0.0005% to about 50%, from about 0.0001% to about 20%, from about 0.005% to about 10%, from about 0.05% to about 5% or from about 0.01% to about 1% by weight, based on the weight of polyolefin to be stabilized.

b. an antioxidant (in the concentration range from about 0.0005% to about 50%, from about 0.0001% to about 20%, from about 0.005% to about 10%, from about 0.05% to about 5% or from about 0.01% to about 1%) along with organic phosphorus stabilizers. The organic phosphorus stabilizers are used for example, in amounts of, from about 0.001% to about 30%, from about 0.005% to about 20%, from about 0.01% to about 5%, from about 0.05% to about 2% or from about 0.1% to about 1%, by weight, based on the weight of the polyolefin to be stabilized.

c. an antioxidant (in the concentration range from about 0.0005% to about 50%, from about 0.0001% to about 50%, from about 0.005% to about 10%, from about 0.05% to about 5% or from about 0.01% to about 1%) along with acid scavengers and organic phosphorus stabilizers in concentrations described in a. and b. above.

d. an antioxidant in combination with other known commercially available antioxidants, such as, for example, Irganox® 1010, Irganox® 1330, Irganox® 1076 and Irganox® 1135 or other antioxidants described above or incorporated herein by reference along with the formulations described in a.-c. above.

Polyolefins

In certain embodiments of the present invention, polyolefins and mixtures of polyolefins can be stabilized by contacting the polyolefin or mixture of polyolefins with a composition of the present invention. These polyolefins and mixtures of polyolefins, include, but are not limited to substituted polyolefins, polyacrylates, polymethacrylates and copolymers of polyolefins. The following are examples of some types of polyolefins which can be stabilized by the methods of the present invention:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be cross-linked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), very low density polyethylene (VLDPE) and ultra low density polyethylene (ULDPE).

Polyolefins, i.e. the polymers of monoolefins exemplified in the preceding paragraph, for example polyethylene and polypropylene, can be prepared by different, and especially by the following, methods:

i) radical polymerization (normally under high pressure and at elevated temperature).

ii) catalytic polymerization using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either p- or s-coordinated. These metal complexes may be in the free form or fixed on substrates, typically on activated magnesium chloride, titanium (III) chloride, and alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, said metals being elements of groups Ia, IIa and/or Ma of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1, for example, mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Blends of polymers mentioned under 1 with impact modifiers such as ethylene-propylene-diene monomer copolymers (EPDM), copolymers of ethylene with higher alpha-olefins (such as ethylene-octene copolymers), polybutadiene, polyisoprene, styrene-butadiene copolymers, hydrogenated styrene-butadiene copolymers, styrene-isoprene copolymers, hydrogenated styrene-isoprene copolymers. These blends are commonly referred to in the industry as TPO's (thermoplastic polyolefins).

In other embodiment polymers of the present invention include biopolymers, bio copolymers, bio-elastomers, bioplastics and their blends with synthetic polymers mentioned in sub-sections 1-4 of the preceding paragraph.

In certain particular embodiments polyolefins of the present invention are for example polypropylene homo- and copolymers and polyethylene homo- and copolymers. For instance, some polyolefin Ares polypropylene, high density polyethylene (HDPE), linear low density polyethylene (LLDPE) and polypropylene random and impact (heterophasic) copolymers.

In certain particular embodiments polyolefins of the present invention are for a wide range of industrial and household applications including but not limited to wire and cables, insulators and jackets, carriers and containers for solids, liquids and powders, packaging, automotive, aviation, and ship components and parts, industrial applications, papers, paints, tires, thin and thick sheets, solids, pipes and tubes, composites with other materials like for example carbon, wood, leather, and metals, electric, housing for wires, electric, electronic and optical components including computers, filters and sponges, geo-membrane liners, housing and building components including roofing shingles, cosmetics, fragrance and toiletries, starch products, textile products and diapers.

Stabilizers
Acid Scavengers or Acid Stabilizers

"Acid scavengers or stabilizers" are defined herein as antacids or co-stabilizers which neutralize the acidic catalysts or other components present in the polymers.

In certain embodiments, of the present invention the acid scavengers which are suitable for use in the methods of the present invention include but are not limited to: zinc oxide, calcium lactate, natural and synthetic hydrotalcites, natural and synthetic hydrocalumites, and alkali metal salts and alkaline earth metal salts of higher fatty acids for example calcium stearate, zinc stearate, magnesium behenate, magnesium stearate, sodium stearate, sodium ricinoleate and potassium palmitate, antimony pyrocatecholate and zinc pyrocatecholate. Combinations of acid scavengers may also be employed.

In certain particular embodiments, the acid scavengers are used for example, in amounts of from about 0.0005% to about 50% by weight, about 0.0001% to about 20% by weight, about 0.005% to about 5% by weight, about 0.01% to about 3% by weight, about 0.05% to about 2% by weight, or about 0.1% to about 1% by weight, based on the weight of polyolefin to be stabilized.

Organic Phosphorus Stabilizers

In certain embodiments of the present invention, examples of organic phosphorus stabilizers (or phosphorus stabilizers) include phosphates, phosphites and phosphonites which are suitable for use in the methods of the present invention. Specific examples of phosphorus stabilizers include but are not limited to: triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, ethanamine, 2-[[2,4,8,10-tetrakis(1,1dimethylethyl)dibenzo[d,f][1,2,3]dioxaphosphepin-6-yl]oxy]-N,N-[bis[2-[[2,4,8,10-tetrakis(1,1diemthylethyl)dibenzo[d,f][1,2,3]dioxaphepin-6-yl]oxy]ethyl] (represented by structural formula (B) diisodecyl pentaerythritol diphosphite, bis(2,4-di-tert-butylphenyl) pentaerythritol diphosphite (represented by structural formula (D) below), bis(2,6-di-tert-butyl-4-methylphenyl) pentaerythritol diphosphite (represented by structural formula (E) below), 3,9-bis(octadecylpxy)-2,4,8,10-tetraoxa-3,9-diphosphaspiro[5,5undecane (represented by structural formula (F), bisisodecyloxypentaerythritol diphosphite, bis(2,4-di-tert-butyl-6-methylphenyl) pentaerythritol diphosphite, bis¬(2,4,6-tri-tert-butylphenyl) pentaerythritol diphosphite, tristearyl sorbitol triphosphite, tetrakis ¬(2,4-di-tert-butylphenyl) 4,4'-biphenylene-diphosphonite (represented by structural formula (H) below), 6-isooctyloxy-2,4,8,10-tetra-tert-butyl-dibenzo[d,f][1,3,2]dioxaphosphepin (represented by structural formula (C) below), 6-fluoro-2,4,8,10-tetra-tert-butyl-12-methyl-dibenzo[d,g][1,3,2]dioxaphosphocin (represented by structural formula (A) below), bis(2,4-di-tert-butyl-6-methylphenyl) methyl phosphite, bis(2,4 di-tert-butyl-6-methylphenyl) ethyl phosphite (represented by structural formula (G) below), (2,4,6-tri-tert-butylphenyl) 2-butyl-2-ethyl-1,3-propanediol phosphate (represented by structural formula (J) below), bis(2,4-di-cumylphenyl) pentaerythritol diphosphite (represented by structural formula (K) below), and structural formula (L) below:

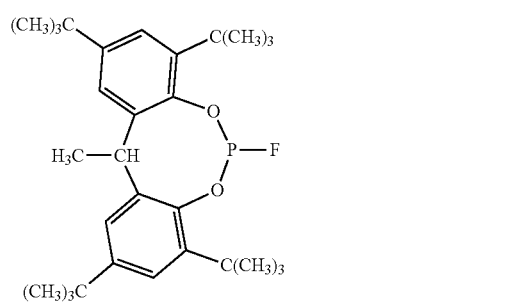

(A)

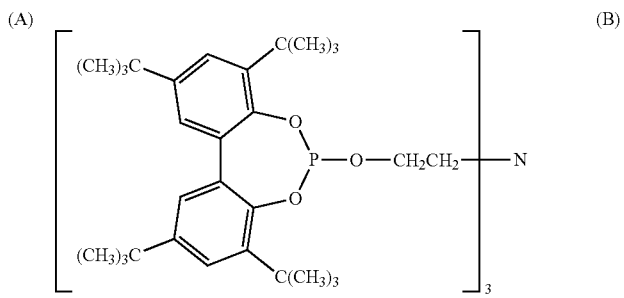

(B)

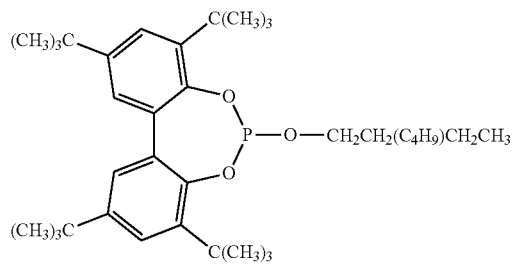

(C)

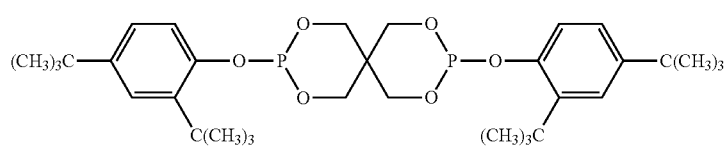

(D)

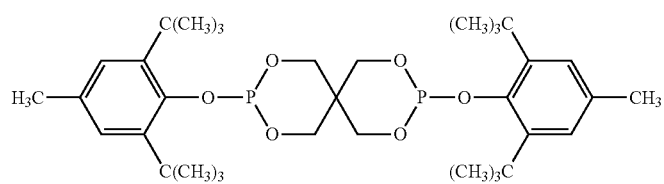
(E)
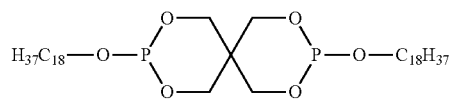
(F)
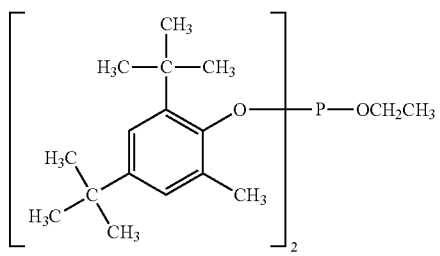
(G)
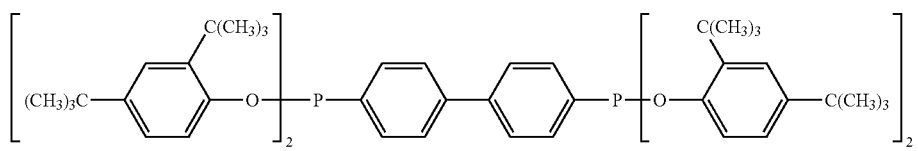
(H)
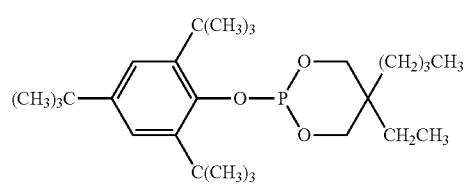
(J)
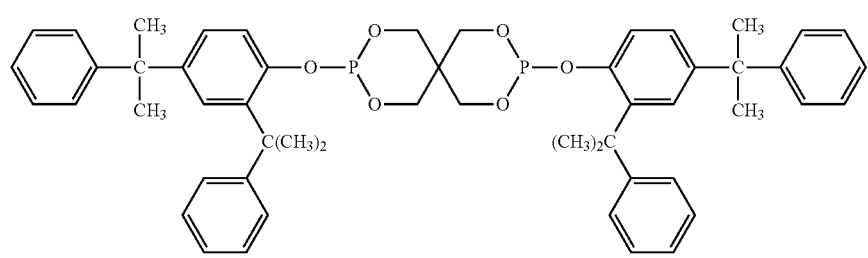
(K)
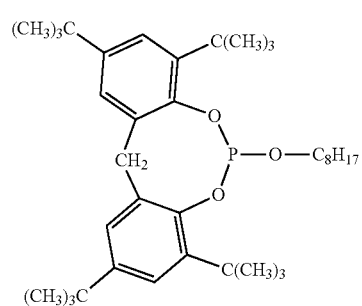
(L)

In certain other embodiments of the present invention, the following compounds are examples of organic phosphites and phosphonites which are suitable for use in the methods of the present invention as organic phosphorus stabilizers: tris(2,4-di-tert-butylphenyl) phosphite, bis(2,4-di-tert-butylphenyl) pentaerythritol diphosphite (formula (D)), tetrakis (2,4-di-tert-butylphenyl) 4,4'-biphenylene-diphosphonite (formula (H)), (2,4,6-tri-tert-butylphenyl) 2-butyl-2-ethyl-1,3-propanediol phosphate (formula (J)), or bis(2,4-di-cumylphenyl) pentaerythritol diphosphite (formula (K)).

The organic phosphorus stabilizers are used, for example, in amounts of from about 0.001% to about 50% by weight, about 0.005% to about 20% by weight, about 0.01% to about 5% by weight, 0.05% to about 3% by weight, 0.1% to about 2% by weight or 0.1% to about 1% by weight based on the weight of the polyolefin to be stabilized.

Co-Stabilizers

In certain embodiments of the present invention, in addition to antioxidants and stabilizers described above the compositions of the present invention may comprise further co-stabilizers (e.g., additives) such as, for example, the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-di-tert-butyl-4-octadecylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-di octylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.

1.4. Tocopherols, for example a-tocopherol, β-tocopherol, γ-tocopherol, γ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-($\alpha$-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha,\alpha$-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis-(3,5-di-tert-butyl-4-hydroxybenzyl)malonate, bis[4-(1,1,3,3-tetramethylbutyl) phenyl]-2,2-bis(3,5-di-tert-butyl-4-hydroxybenzyl) malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.14. Esters of β-(5-tert-butyl-4-hydroxy-3-methylphenyl)propionic acid with mono- or polyhydric alcohols, e.g.

with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid, e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl] propionyloxy)ethyl]oxamide (Naugard® XL-1, Crompton Corporation).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino] ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethy-lpiperidin-4-one, 2,2,6,6-tetramethylpiperidin-4-ol.

2. Hindered Amine Stabilizers

As defined herein, "hindered amine stabilizers" are hindered amines which produce nitroxyl radicals that react with alkyl radicals produced during thermo-oxidation of the polymers.

2.1. Sterically hindered amine stabilizers, for example 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, bis(2,2,6,6-tetramethyl-4-piperidyl) sebacate, bis(2,2,6,6-tetramethyl-4-piperidyl) succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl) malonate, 3-n-octyl-7,7,9,9-tetramethyl-1,3,8-triazaspiro [4.5]decan-2,4-dione, bis(1-octyloxy-2,2,6,6-tetramethylpiperidyl) sebacate, bis(1-octyloxy-2,2,6,6-tetramethyl-piperidyl) succinate, linear or cyclic condensates of N,N'-bis-(2,2,6,6-tetramethyl-4-piperidyl)-hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-amino-propylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3, 5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3, 8-diaza-4-oxo-spiro[4.5]decane, a reaction product of 7,7,9, 9-tetramethyl-2-cycloundecyl-1-oxa-3,8-diaza-4-oxospiro [4.5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of 4-methoxy-methylenemalonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

The sterically hindered amine may also be one of the compounds described in U.S. Pat. No. 5,980,783, the entire contents of which are incorporated herein by reference, that is compounds of component I-a), I-b), I-c), I-d), I-e), I-f), I-g), I-h), I-i), I-j), I-k) or I-l), in particular the light stabilizer 1-a-1, 1-a-2, 1-b-1, 1-c-1, 1-c-2, 1-d-1, 1-d-2, 1-d-3, 1-e-1, 14-1, 1-g-1, 1-g-2 or 1-k-1 listed on columns 64-72 of said U.S. Pat. No. 5,980,783.

The sterically hindered amine may also be one of the compounds described in U.S. Pat. Nos. 6,046,304 and 6,297,299, the entire contents of each of which are incorporated herein by reference.

2.2. Sterically hindered amines substituted on the N-atom by a hydroxy-substituted alkoxy group, for example compounds such as 1-(2-hydroxy-2-methylpropoxy)-4-octadecanoyloxy-2,2,6,6-tetramethylpiperidine, 1-(2-hydroxy-2-methylpropoxy)-4-hexadecanoyloxy-2,2,6,6-tetramethylpiperidine, the reaction product of 1-oxyl-4-hydroxy-2,2,6,6-tetramethylpiperidine with a carbon radical from t-amylalcohol, 1-(2-hydroxy-2-methylpropoxy)-4-hydroxy-2,2,6,6-tetramethylpiperidine, 1-(2-hydroxy-2-methylpropoxy)-4-oxo-2,2,6,6-tetramethylpiperidine, bis(1-(2-hydroxy-2-methylpropoxy)-2,2,6,6-tetramethyl-piperidin-4-yl) sebacate, bis(1-(2-hydroxy-2-methylpropoxy)-2,2,6,6-tetramethylpiperidin-4-yl) adipate, bis(1-(2-hydroxy-2-methylpropoxy)-2,2,6,6-tetramethylpiperidin-4-yl) succinate, bis(1-(2-hydroxy-2-methylpropoxy)-2,2,6,6-tetramethylpiperidin-4-yl) glutarate and 2,4-bis {N-[1-(2-hydroxy-2-methylpropoxy)-2,2,6,6-tetramethylpiperidin-4-yl]-N-butylamino}-6-(2-hydroxy-ethylamino)-s-triazine.

3. Ultraviolet Absorbers

As defined herein "ultraviolet absorbers" essentially absorb the harmful UV radiation and dissipate it so that is does not lead to photosensitization i.e., dissipation as heat.

3.1. 2-(2-Hydroxyphenyl)-2H-benzotriazoles, for example known commercial hydroxyphenyl-2H-benzotriazoles and benzotriazoles as disclosed in, U.S. Pat. Nos. 3,004,896; 3,055,896; 3,072,585; 3,074,910; 3,189,615; 3,218,332; 3,230,194; 4,127,586; 4,226,763; 4,275,004; 4,278,589; 4,315,848; 4,347,180; 4,383,863; 4,675,352; 4,681,905, 4,853,471; 5,268,450; 5,278,314; 5,280,124; 5,319,091; 5,410,071; 5,436,349; 5,516,914; 5,554,760; 5,563,242; 5,574,166; 5,607,987 and 5,977,219, the entire contents of each of which are incorporated herein by reference, such as 2-(2-hydroxy-5-methylphenyl)-2H-benzotriazole, 2-(3,5-di-tert-butyl-2-hydroxyphenyl)-2H-benzotriazole, 2-(2-hydroxy-5-tert-butylphenyl)-2H-benzotriazole, 2-(2-hydroxy-5-tert-octylphenyl)-2H-benzotriazole, 5-chloro-2-(3,5-di-tert-butyl-2-hydroxyphenyl)-2H-benzotriazole, 5-chloro-2-(3-tert-butyl-2-hydroxy-5-methylphenyl)-2H-benzotriazole, 2-(3-sec-butyl-5-tert-butyl-2-hydroxyphenyl)-2H-benzotriazole, 2-(2-hydroxy-4-octyloxyphenyl)-2H-benzotriazole, 2-(3,5-di-tert-amyl-2-hydroxyphenyl)-2H-benzotriazole, 2-(3,5-bis-α-cumyl-2-hydroxyphenyl)-2H-benzotriazole, 2-(3-tert-butyl-2-hydroxy-5-(2-(ω-hydroxy-octa-(ethyleneoxy)carbonyl-ethyl)-, phenyl)-2H-benzotriazole, 2-(3-dodecyl-2-hydroxy-5-methylphenyl)-2H-benzotriazole, 2-(3-tert-butyl-2-hydroxy-5-(2-octyloxycarbonyl)ethylphenyl)-2H-benzotriazole, dodecylated 2-(2-hydroxy-5-methylphenyl)-2-H-benzotriazole, 2-(3-tert-butyl-2-hydroxy-5-(2-octyloxycarbonylethyl)phenyl)-5-chloro-2H-benzotriazole, 2-(3-tert-butyl-5-(2-(2-ethylhexyloxy)-carbonylethyl)-2-hydroxyphenyl)-5-chloro-2H-benzotriazole, 2-(3-tert-butyl-2-hydroxy-5-(2-methoxycarbonylethyl)phenyl)-5-chloro-2H-benzotriazole, 2-(3-tert-butyl-2-hydroxy-5-(2-methoxycarbonylethyl)phenyl)-2H-benzotriazole, 2-(3-tert-butyl-5-(2-(2-ethylhexyloxy)carbonylethyl)-2-hydroxyphenyl)-2H-benzotriazole, 2-(3-tert-butyl-2-hydroxy-5-(2-isooctyloxycarbonylethyl)phenyl-2H-benzotriazole, 2,2'-methylene-bis(4-tert-octyl-(6-2H-benzotriazol-2-yl)phenol), 2-(2-hydroxy-3-α-cumyl-5-tert-octylphenyl)-2H-benzotriazole, 2-(2-hydroxy-3-tert-octyl-5-α-cumylphenyl)-2H-benzotriazole, 5-fluoro-2-(2-hydroxy-3,5-di-α-cumylphenyl)-2H-benzotriazole, 5-chloro-2-(2-hydroxy-3,5-di-α-cumylphenyl)-2H-benzotriazole, 5-chloro-2-(2-hydroxy-3-α-cumyl-5-tert-octylphenyl)-2H-benzotriazole, 2-(3-tert-butyl-2-hydroxy-5-(2-isooctyloxycarbonylethyl)phenyl)-5-chloro-2H-benzotriazole, 5-trifluoromethyl-2-(2-hydroxy-3-α-cumyl-5-tert-octylphenyl)-2H-benzotriazole, 5-trifluoromethyl-2-(2-hydroxy-5-tert-octylphenyl)-2H-benzotriazole, 5-trifluoromethyl-2-(2-hydroxy-3,5-di-tert-octylphenyl)-2H-benzo-triazole, methyl 3-(5-trifluoromethyl-2H-benzotriazol-2-yl)-5-tert-butyl-4-hydroxyhydrocinnamate, 5-butylsulfonyl-2-(2-hydroxy-3-α-cumyl-5-tert-octylphenyl)-2H-benzotriazole, 5-trifluoromethyl-2-(2-hydroxy-3-α-cumyl-5-tert-butylphenyl)-2H-benzotriazole, 5-trifluoromethyl-2-(2-hydroxy-3,5-di-tert-butylphenyl)-2H-benzotriazole, 5-trifluoromethyl-2-(2-hydroxy-3,5-di-α-cumylphenyl)-2H-benzotriazole, 5-butylsulfonyl-2-(2-hydroxy-3,5-di-tert-butylphenyl)-2H-benzotriazole and 5-phenylsulfonyl-2-(2-hydroxy-3,5-di-tert-butylphenyl)-2H-benzotriazole.

3.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

3.3. Esters of substituted and unsubstituted benzoic acids, as for example 4-tert-butyl-phenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

3.4. Acrylates and malonates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline, Sanduvor® PR 25, (Clariant), dimethyl p-methoxybenzylidenemalonate (CAS#7443-25-6), and Sanduvor® PR 31 (Clariant), di-(1,2,2,6,6-pentamethylpiperid-in-4-yl) p-methoxy-benzylidenemalonate (CAS #147783-69-5).

3.5. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

3.6. Tris-aryl-o-hydroxyphenyl-s-triazines, for example known commercial tris-aryl-o-hydroxyphenyl-s-triazines and triazines as disclosed in, WO 96/28431, EP 434608, EP 941989, GB 2,317,893, U.S. Pat. Nos. 3,843,371; 4,619,956; 4,740,542; 5,096,489; 5,106,891; 5,298,067; 5,300,414; 5,354,794; 5,461,151; 5,476,937; 5,489,503; 5,543,518; 5,556,973; 5,597,854; 5,681,955; 5,726,309; 5,942,626; 5,959,008; 5,998,116 and 6,013,704, the entire contents of each of which are incorporated herein by reference, for example 4,6-bis-(2,4-dimethylphenyl)-2-(2-hydroxy-4-octyloxyphenyl)-s-triazine (Cyasorb® 1164, Cytec Corp.), 4,6-bis-(2,4-dimethylphenyl)-2-(2,4-dihydroxyphenyl)-s-triazine, 2,4-bis(2,4-dihydroxyphenyl)-6-(4-chlorophenyl)-s-triazine, 2,4-bis[2-hydroxy-4-(2-hydroxpethoxy)phenyl]-6-(4-chlorophenyl)-s-triazine, 2,4-bis[2-hydroxy-4-(2-hydroxy-4-(2-hydroxyethoxy)phenyl]-6-(2,4-dimethylphenyl)-s-triazine, 2,4-bis[2-hydroxy-4-(2-hydroxyethoxy)phenyl]-6-(4-bromophenyl)-s-triazine, 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine, 2,4-bis(4-biphenylyl)-6-(2-hydroxy-4-octyloxycarbonylethylideneoxyphenyl)-s-triazine, 2-phenyl-4-[2-hydroxy-4-(3-sec-butyloxy-2-hydroxypropyloxy)phenyl]-6-[2-hydroxy-4-(3-sec-amyloxy-2-hydroxy-propyloxy)phenyl]-s-triazine, 2,4-bis(2,4-dimethylphenyl)-6-[2-hydroxy-4-(3-benzyloxy-2-hydroxypropyloxy)phenyl]-s-triazine, 2,4-bis(2-hydroxy-4-n-butyloxyphenyl)-6-(2,4-di-n-butyloxyphenyl)-s-triazine, 2,4-bis(2,4-dimethylphenyl)-6-[2-hydroxy-4-(3-nonyloxy*-2-hydroxypropyloxy)-5-α-cumylphenyl]-s-triazine (* denotes a mixture of octyloxy, nonyloxy and decyloxy groups), methylenebis-{2,4-bis(2,4-dimethylphenyl)-6-[2-hydroxy-4-(3-butyloxy-2-hydroxypropoxy)phenyl]-s-triazine}, methylene bridged dimer mixture bridged in the 3:5', 5:5' and 3:3' positions in a 5:4:1 ratio, 2,4,6-tris(2-hydroxy-4-isooctyloxycarbonylisopropylideneoxy-phenyl)-s-triazine, 2,4-bis(2,4-dimethylphenyl)-6-(2-hydroxy-4-hexyloxy-5-α-cumylphenyl)-s-triazine, 2-(2,4,6-trimethylphenyl)-4,6-bis[2-hydroxy-4-(3-butyloxy-2-hydroxypropyloxy)-phenyl]-s-triazine, 2,4,6-tris[2-hydroxy-4-(3-sec-butyloxy-2-hydroxapropyloxy)phenyl]-s-triazine, mixture of 4,6-bis-(2,4-dimethylphenyl)-2-(2-hydroxy-4-(3-dodecyloxy-2-hydroxypropoxy)-phenyl)-s-triazine and 4,6-bis-(2,4-dimethylphenyl)-2-(2-hydroxy-4-(3-tridecyloxy-2-hydroxypropoxy)-phenyl)-s-triazine, Tinuvin® 400, Ciba Specialty Chemicals Corp., 4,6-bis-(2, 4-dimethylphenyl)-2-(2-hydroxy-4-(3-(2-ethylhexyloxy)-2-hydroxypropoxy)-phenyl)-s-triazine and 4,6-diphenyl-2-(4-hexyloxy-2-hydroxyphenyl)-s-triazine.

4. Metal deactivators, as used herein are compounds which form stable complexes with metal ions and inhibit their reaction with peroxides, for example, N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

5. Peroxide scavengers, for example, esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Hydroxylamines, for example, N,N-dihydrocarbylhydroxylamines selected from the group consisting of N,N-dibenzylhydroxylamine, N,N-dimethylhydroxylamine, N,N-diethylhydroxylamine, N,N-bis(2-hydroxypropyl)hydroxylamine, N,N-bis(3-hydroxypropyl)-hydroxylamine, N,N-bis(2-carboxyethyl)hydroxylamine, N,N-bis(benzylthiomethyl)hydroxyl-amine, N,N-dioctylhydroxylamine, N,N-dilaurylhydroxylamine, N,N-didodecylhydroxylamine, N,N-ditetradecylhydroxylamine, N,N-dihexadecylhydroxylamine, N,N-dioctadecylhydroxylamine, N-hexadecyl-N-tetradecylhydroxylamine, N-hexadecyl-N-heptadecylhydroxylamine, N-hexadecyl-N-octadecylhydroxylamine, N-heptadecyl-N-octadecylhydroxylamine, N-methyl-N-octadecylhydroxylamine, and N,N-di(hydrogenated tallow)hydroxylamine.

The hydroxylamine may be for example the N,N-di(alkyl) hydroxylamine produced by the direct oxidation of N,N-di(hydrogenated tallow)amine. For example, the hydroxylamine prepared by direct hydrogen peroxide oxidation of bis(hydrogenated tallow alkyl) amines that are N, N-di(hydrogenated tallow) hydroxylamine, CAS #143925-92-2. N,N-di(hydrogenated tallow)hydroxylamine is prepared as in the working Examples of U.S. Pat. No. 5,013,510 the entire contents of which are incorporated herein by reference.

7. Nitrones, for example, N-benzyl-α-phenyl-nitrone, N-ethyl-α-methyl-nitrone, N-octyl-α-heptyl-nitrone, N-lauryl-α-undecyl-nitrone, N-tetradecyl-α-tridecyl-nitrone, N-hexadecyl-α-pentadecyl-nitrone, N-octadecyl-α-heptadecyl-nitrone, N-hexadecyl-α-heptadecyl-nitrone, N-ocatadecyl-α-pentadecyl-nitrone, N-heptadecyl-α-heptadecyl-nitrone, N-octadecyl-α-hexadecyl-nitrone, nitrone derived from N,N-di(hydrogenated tallow)hydroxylamine.

8. Amine-N-oxides, for example Genox™ EP, a di($C_{16}$-$C_{18}$)alkyl methyl amine oxide, CAS#204933-93-7, Crompton Corporation.

9. Benzofuranones and indolinones, for example those disclosed in U.S. Pat. Nos. 4,325,863; 4,338,244; 5,175,312; 5,216,052; 5,252,643; 5,369,159; 5,488,117; 5,356,966; 5,367,008; 5,428,162; 5,428,177; 5,516,920; DE-A-4316611; DE-A-4316622; DE-A-4316876; EP-A-0589839 or EP-A-0591102 the entire contents of each of which are incorporated herein by reference, or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

10. Polyhydric alcohols, for example pentaerythritol and glycerol.

11. Basic co-stabilizers, for example, melamine, polyvinylpyrrolidone, dicyandiamide, triallyl cyanurate, urea derivatives, hydrazine derivatives, amines, polyamides and polyurethanes.

12. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate, lithium benzoate, disodium bicycle[2.2.1]heptane 2,3-dicarboxylate; organic phosphates and salts thereof, e.g. sodium 2,2'-methylenebis (4,6-di-tert-butylphenyl)phosphate, and polymeric compounds such as ionic copolymers (ionomers).

13. Clarifiers, for example substituted and unsubstituted bisbenzylidene sorbitols.

14. Fillers and reinforcing agents, for example, calcium carbonate, silicates, glass fibers, glass bulbs, asbestos, talc, wollastonite, nanoclays, kaolin, mica, barium sulfate, metal oxides and hydroxides, carbon black, graphite, wood flour and flours or fibers of other natural products, synthetic fibers.

15. Dispersing Agents, as used herein are compounds which when added to a colloidal solution disperse the particles uniformly, such as, for example, polyethylene oxide waxes or mineral oil.

16. Other additives, for example, plasticizers, lubricants, emulsifiers, pigments, rheology additives, catalysts, flow-control agents, optical brighteners, flame retardants, anti-static agents, antimicrobials and blowing agents.

In certain embodiments of the present invention the co-stabilizers are added, for example, in concentrations of from about 0.0001% to about 50% by weight, about 0.0005% to about 20% by weight, about 0.001% to about 10% by weight, from about 0.01% to about 5% by weight, from about 0.05% to about 1% by weight from about 0.1% to about 1% by weight based on the overall weight of the polyolefin to be stabilized.

In certain other embodiments of the present invention the fillers and reinforcing agents, for example talc, calcium carbonate, mica or kaolin, are added to the polyolefins in concentrations of about 0.001% to about 80% by weight, about 0.005% to about 60% by weight, about 0.01% to about 40% by weight, of about 0.05% to about 20% by weight, of about 0.1% to about 10% by weight, of about 0.5% to about 5% by weight, based on the overall weight of the polyolefins to be stabilized.

In certain particular embodiments of the present invention the fillers and reinforcing agents, for example metal hydroxides, especially aluminum hydroxide or magnesium hydroxide, are added to the polyolefins in concentrations of about 0.001% to about 80% by weight, about 0.005% to about 70% by weight, about 0.01% to about 60% by weight, about 0.1% to about 50% by weight about 0.5% to about 40% by weight about 1% to about 20% by weight based on the overall weight of the polyolefins to be stabilized.

In certain particular embodiments of the present invention carbon black as filler is added to the polyolefins in concentrations, judiciously, of from about 0.001% to about 30% by weight, 0.005% to about 10% by weight, 0.01% to about 5% by weight, of from about 0.05% to about 3% by weight of from about 0.1% to about 2% by weight of from about 0.1% to about 1% by weight based on the overall weight of the polyolefins to be stabilized.

In certain particular embodiments of the present invention glass fibers as reinforcing agents are added to the polyolefins in concentrations, judiciously, of from of about 0.001% to about 80% by weight, about 0.005% to about 60% by weight, about 0.01% to about 40% by weight, of about 0.05% to about 20% by weight, of about 0.1% to about 10% by weight, based on the overall weight of the polyolefins to be stabilized.

The term "alkyl" as used herein means a saturated straight-chain, branched or cyclic hydrocarbon. When straight-chained or branched, an alkyl group is typically C1-C8, more typically C1-C6; when cyclic, an alkyl group is typically C3-C12, more typically C3-C7 alkyl ester. Examples of alkyl groups include methyl, ethyl, n propyl, iso propyl, n butyl, sec butyl and tert butyl and 1,1-dimethylhexyl.

The term "alkoxy" as used herein is represented by —OR, wherein R is an alkyl group as defined above.

The term "acyl" as used herein is represented by —C(O)R, wherein R is an alkyl group as defined above.

The term "alkyl ester" as used herein means a group represented by —C(O)OR, where R is an alkyl group as defined above.

The term "aromatic group" used alone or as part of a larger moiety as in "aralkyl", includes carbocyclic aromatic rings and heteroaryl rings. The term "aromatic group" may be used interchangeably with the terms "aryl", "aryl ring" "aromatic ring", "aryl group" and "aromatic group".

Carbocyclic aromatic ring groups have only carbon ring atoms (typically six to fourteen) and include monocyclic aromatic rings such as phenyl and fused polycyclic aromatic ring systems in which a carbocyclic aromatic ring is fused to one or more aromatic rings (carbocyclic aromatic or heteroaromatic). Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The term "heteroaryl", "heteroaromatic", "heteroaryl ring", "heteroaryl group" and "heteroaromatic group", used alone or as part of a larger moiety as in "heteroaralkyl" refers to heteroaromatic ring groups having five to fourteen members, including monocyclic heteroaromatic rings and polycyclic aromatic rings in which a monocyclic aromatic ring is fused to one or more other aromatic ring (carbocyclic aromatic or heteroaromatic). Heteroaryl groups have one or more ring heteroatoms. Examples of heteroaryl groups include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, 2 benzothienyl, 3 benzothienyl, 2 benzofuranyl, 3 benzofuranyl, 2 indolyl, 3 indolyl, 2 quinolinyl, 3 quinolinyl, 2 benzothiazole, 2 benzooxazole, 2 benzimidazolyl, 2 quinolinyl, 3 quinolinyl, 1 isoquinolinyl, 3 quinolinyl, 1 isoindolyl and 3 isoindolyl. Also included within the scope of the term "heteroaryl", as it is used herein, is a group in which an aromatic ring is fused to one or more non-aromatic rings (carbocyclic or heterocyclic), where the radical or point of attachment is on the aromatic ring.

The term "heteroatom" means nitrogen, oxygen, or sulfur and includes any oxidized form of nitrogen and sulfur, and the quaternized form of any basic nitrogen. Also the term "nitrogen" includes substitutable nitrogen of a heteroaryl or non-aromatic heterocyclic group. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR" (as in N-substituted pyrrolidinyl), wherein R" is a suitable substituent for the nitrogen atom in the ring of a non-aromatic nitrogen-containing heterocyclic group, as defined below.

An "aralkyl group", as used herein is an alkyl groups substituted with an aryl group as defined above.

An optionally substituted aryl group as defined herein may contain one or more substitutable ring atoms, such as carbon or nitrogen ring atoms. Examples of suitable substituents on a substitutable ring carbon atom of an aryl group include —OH, C1-C3 alkyl, C1-C3 haloalkyl, —NO$_2$, C1-C3 alkoxy, C1-C3 haloalkoxy, —CN, —NH$_2$, C1-C3 alkylamino, C1-C3 dialkylamino, —C(O)NH$_2$, —C(O)NH (C1-C3 alkyl), —C(O)(C1-C3 alkyl), —NHC(O)H, —NHC (O)(C1-C3 alkyl), —C(O)N(C1-C3 alkyl)$_2$, —NHC(O)O— (C1-C3 alkyl), —C(O)OH, —C(O)O—(C1-C3 alkyl), —NHC(O)NH$_2$, —NHC(O)NH(C1-C3 alkyl), —NHC(O)N (C1-C3 alkyl)$_2$, —SO$_2$NH$_2$—SO$_2$NH(C1-C3alkyl), —SO$_2$N(C1-C3alkyl)$_2$, NHSO$_2$H or NHSO$_2$(C1-C3 alkyl). Preferred substituents on aryl groups are as defined throughout the specification. In certain embodiments optionally substituted aryl groups are unsubstituted.

Examples of suitable substituents on a substitutable ring nitrogen atom of an aryl group include C1-C3 alkyl, NH$_2$, C1-C3 alkylamino, C1-C3 dialkylamino, —C(O)NH$_2$, —C(O)NH(C1-C3 alkyl), —C(O)(C1-C3 alkyl), —CO$_2$R, —C(O)C(O)R, —C(O)CH$_3$, —C(O)OH, —C(O)O—(C1-C3 alkyl), —SO$_2$NH$_2$—SO$_2$NH(C1-C3alkyl), —SO$_2$N(C1-C3alkyl)$_2$, NHSO$_2$H, NHSO$_2$(C1-C3 alkyl), —C(=S)NH$_2$, —C(=S)NH(C1-C3 alkyl), —C(=S)N(C1-C3 alkyl)$_2$, —C(=NH)—N(H)$_2$, —C(=NH)—NH(C1-C3 alkyl) and —C(=NH)—N(C1-C3 alkyl)$_2$.

An optionally substituted alkyl group as defined herein may contain one or more substituents. Examples of suitable substituents for an alkyl group include those listed above for a substitutable carbon of an aryl and the following: =O, =S, =NNUR, =NN(R)$_2$, =NNHC(O) R, =NNHCO$_2$ (alkyl), =NNHSO$_2$ (alkyl), =NR, spiro cycloalkyl group or fused cycloalkyl group. R** in each occurrence, independently is —H or C1-C6 alkyl. Preferred substituents on alkyl groups are as defined throughout the specification. In certain embodiments optionally substituted alkyl groups are unsubstituted.

A "spiro cycloalkyl" group is a cycloalkyl group which shares one ring carbon atom with a carbon atom in an alkylene group or alkyl group, wherein the carbon atom being shared in the alkyl group is not a terminal carbon atom.

The polyamide is generally known as nylon having the formula

where x is an integer, preferably 6, 9, 10, 11 or 12. Any suitable nylon may be employed as the base resin in the composition according to the invention. Preferred nylons are Nylon-6 (polycaprolactam), Nylon-6,6 (polyhexamethylene adipamide), Nylon-6,9 (polyhexamethylene azelaamide), Nylon-6,10 (polyhexamethylene sebacamide), Nylon-6,12 (polyhexamethylene dodecanoamide), Nylon-1(polyundecanoamide) and Nylon-12 (polydodecanoamide). The nylon base resin will be preferably 100% of the units represented by the formula, but it may also contain non-polyamide units, e.g. an olefin homopolymer or copolymer. In such polycopolyamides, polyamides generally comprise at least 25%, preferably at least 75%, particularly essentially 100% units having the above formula.

In another embodiment the polymer is selected from the group consisting of polyamide, polyester and combination thereof; preferably polymer is selected from the group consisting of polyamide, such as nylon 6, nylon 66, nylon 10, nylon1010, nylon 12, nylon1212, nylon610, nylon 612, PPA, PA6T, PAST and combination thereof; and preferably the polymer is selected from the group consisting of PET, PBT, PTT and combinations thereof.

As disclosed in Kirk-Othmer Encyclopedia of Chemical Technology, Volume 19, pages 772-797, polyamide composition which is incorporated herein by reference, nylon may be compounded with a wide range of additives that include lubricants to improve the melt flow, screw feeding and mold release; nucleants which are finely dispersed seed the molten nylon and result in a higher density of small uniformly sized spherulites to increase the tensile strength and stiffness; stabilizers to slow down the rate of oxidation and UV aging by adding antioxidants, ultraviolet stabilizers, hydro-peroxide decomposers, or metal salts mostly in the form of copper halide mixtures; impact modifiers to improve the notched impact strength and ductility by adding rubbers, olefin copolymers silicones, polyurethanes or modified acrylics; flame retardants to aid inhibiting the combustion process and eliminating burning drips by adding halogenated organics; plasticizers to increase the flexibility of nylon and to improve the impact strength, and reinforcement by adding such as glass fibers or nylon mixing with nanometer size silicates to make nanocomposites to improve the tensile strength and stiffness. To balance the properties nylon are sometimes blended with other polymers e.g. polyethylene or polypropylene.

Description of Polyamides:

Examples of thermoplastic polyamides useful in the compositions of the present invention include semicrystalline or amorphous aliphatic and semi-aromatic polyamides as well as mixtures thereof.

Suitable aliphatic polyamides are derived from aliphatic lactams or aliphatic diamines and dicarboxylic acids and include, for example, polyamide 6, polyamide 11, polyamide 12, polyamide 6,6, polyamide 4,6, polyamide 6,10, polyamide 6,12. Suitable aliphatic polyamides also include copolyamides derived from mixtures of aliphatic diamines, aliphatic dicarboxylic acids, and aliphatic lactams.

Suitable semi-aromatic polyamides are derived from at least one aromatic diamine and/or aromatic dicarboxylic acid monomer and other aliphatic monomers, which may include aliphatic diamines, aliphatic dicarboxylic acids, and aliphatic lactams. Specific examples include PA-6, I, PA-6, I/6,6-copolyamide, PA-6,T, PA-6,T/6-copolyamide, PA-6,T/6,6-copolyamide, PA-6,I/6,T-copolyamide, PA-6,6/6,T/6,1-copolyamide, PA-6,T/2-MPMD,T-copolyamide (2-MPMD=2-methylpentamethylene diamine), PA-9,T, and PA-9T/2-MOMD,T (2-MOMD=2-methyl-1,8-octamethylenediamine).

Description of Stabilizers for Polyamides:

Heat stabilizing systems for polyamides typically comprise one or more additives selected from the groups of phenolic antioxidants, low-valent phosphorus compounds, aromatic amines, copper salts alone or in combination with one or more alkali or alkaline earth metal halide salts metal salts, and the transition metals and their oxides.

Phenolic antioxidants suitable for use in polyamides are well known in the art and are described by K. Schwarzenbach et al. in "Plastic Additives Handbook", 5$^{th}$ ed., H. Zweifel, Ed., Hanser Publishers, Chapter 1, which is incorporated herein in its entirety by reference. Examples of preferred phenolic antioxidants for use in polyamides include:

N,N'-Hexamethylenebis[3-(3,5-di-tert-butyl-4-hydroxyphenyl)propionamide], Chemical Abstract Service Registry No. 23128-74-7, available from BASF as Irganox® 1098,

[1,2-Bis[3-(3,5-di-tert-butyl-4-hydroxyphenyl)propionoyl] hydrazine, Chemical Abstract Service Registry No. 32687-87-8, available from BASF as Irganox® MD 1024, Pentaerythritol tetrakis[3-(3,5-di-tert-butyl-4-hydroxyphenyl)propionate], Chemical Abstract Service Registry No. 6683-19-8, available from BASF as Irganox® 1010, 1,3,5-Trimethyl-2,4,6-tris(3,5-di-tert-butyl-4-hydroxybenzyl)benzene, Chemical Abstract Service Registry No. 1709-70-2, available from Albemarle Corporation as Ethanox® 330, Butylated reaction product of p-cresol and dicyclopentadiene, Chemical Abstract Service Registry No. 68610-51-5, available from ELIOKEM as Wingstay® L, N-(4-hydroxyphenyl)octadecanamide, Chemical Abstract Service Registry No. 103-99-1, 2-tert-butyl-6-(3-tert-butyl-2-hydroxy-5-methyl) benzyl-4-methylphenyl acrylate, Chemical Abstract Service Registry No. 61167-58-6, available from Sumitomo as Sumilizer® GM, 2-[1-(2-hydroxy-3,5-di-tert-pentylphenyl)ethyl]-4,6-di-tert-pentylphenyl acrylate, Chemical Abstract Service Registry No. 123968-25-2, available from Sumitomo as Sumilizer® GS, and 2,6-Di-tert-butyl-4-[4,6-bis(octylthio)-1,3,5-triazin-2-ylamino]phenol, Chemical Abstract Service Registry No. 991-84-4, available from BASF as Irganox® 565.

Low-valent phosphorus compounds suitable for use in polyamides include organic phosphites and phosphonites, salts of phenylphosphinic acid, and hypophosphite salts. Organic phosphites and phosphonites suitable for use in polyamides are well known in the art and are described by K. Schwarzenbach et al. in "Plastic Additives Handbook", 5$^{th}$ ed., H. Zweifel, Ed., Hanser Publishers, Chapter 1, which is incorporated herein in its entirety by reference. Examples of preferred organic phosphites and phosphonites for use in polyamides include:

Tris(2,4-di-tert-butylphenyl)phosphite, Chemical Abstract Service Registry No. 31570-04-4, available from BASF as Irgafos® 168, Bis(2,4-dicumylphenyl) pentaerythritol diphosphite, Chemical Abstract Service Registry No. 154862-43-8, available from Dover Chemical as Doverphos® S-9228, Bis(2,6-di-tert-butyl-4-methylphenyl) pentaerythritol diphosphite, available from Amfine Chemical as ADK Stab® PEP-36, and Tetrakis(2,4-di-tert-butylphenyl)[1,1'-biphenyl]4,4'-diyl-bisphosphonite, Chemical Abstract Service Registry No. 119345-01-6, available from Clariant as Hostanox® P-EPQ.

Examples of salts of phenylphosphinic acid suitable for use in polyamides include sodium phenylphosphinate (Chemical Abstract Service Registry No. 4297-95-4), zinc phenylphosphinate (Chemical Abstract Service Registry No. 25070-22-8), and other phenylphosphinate salts of alkali metals and alkaline earth metals.

Examples of hypophosphite salts include sodium hypophosphite (Chemical Abstract Service Registry No. 7681-53-0), sodium hypophosphite monohydrate (Chemical Abstract Service Registry No. 10039-56-2) and other hypophosphite salts of alkali metals and alkaline earth metals and their hydrates.

Aromatic amine antioxidants suitable for use in polyamides are well known in the art and are described by K. Schwarzenbach et al. in "Plastic Additives Handbook", 5$^{th}$ ed., H. Zweifel, Ed., Hanser Publishers, Chapter 1, which is incorporated herein in its entirety by reference. Examples of preferred aromatic amine antioxidants for use in polyamides include:

4,4'-Bis(α,α-dimethylbenzyl)diphenylamine, Chemical Abstract Service Registry No. 10081-67-1, available from Chemtura as Naugard® 445, Acetone-diphenylamine condensation product, Chemical Abstract Service Registry No. 9003-79-6, available from Chemtura as Naugard® A, and Styrenated diphenylamines, Chemical Abstract Service Registry No. 68442-68-2, available from ELIOKEM as Wingstay® 29.

Examples of suitable copper salts include copper (I) and copper (II) salts, for example, copper phosphates, copper halides, and copper acetates. Suitable alkali metal halides for use in combination with the copper salts include the chlorides, bromides and iodides of lithium, sodium, potassium, and cesium. Examples of suitable alkaline earth metal halides for use in combination with the copper salts include the chlorides, bromides, and iodides of calcium. Suitable copper (I) halide/alkali metal halide combinations include, for example, CuI/KI and CuI/KBr. When used in combination, preferred ratios of the copper salt to the alkali metal or alkaline earth salt range from about 1:50 to about 2:1 by weight.

Examples of suitable transition metals and their oxides include iron, copper, and the iron oxides.

The preferred concentration of component of the heat stabilizing system ranges from about 0.05% to about 10% by weight, from about 0.01% to about 5%, from about 0.01% to about 3%, from about 0.01% to about 1%, based on the weight of thermoplastic polyamide polymer being stabilized.

In one embodiment, of the present invention the compositions for use in stabilization of polyamides, copolyamides, polyesters, copolyesters and blend of polymer or copolymer with one or more other polymers include but are not limited to:

a. an antioxidant of the instant invention (in the concentration range, from about 0.0001% to about 50%, from about 0.0005% to about 20%, from about 0.005% to about 10%, from about 0.05% to about 5% or from about 0.01% to about 1%) with acid scavengers, for example, in amounts of from about 0.0005% to about 50%, from about 0.0001% to about 20%, from about 0.005% to about 10%, from about 0.05% to about 5% or from about 0.01% to about 1% by weight, based on the weight of polymer or copolymer or blend of polymer with the other polymers or copolymers and blend of polymer or copolymer with one or more other polymers to be stabilized.

b. an antioxidant of the instant invention (in the concentration range from about 0.0005% to about 50%, from about 0.0001% to about 20%, from about 0.005% to about 10%, from about 0.05% to about 5% or from about 0.01% to about 1%) along with organic phosphorus stabilizers. The organic phosphorus stabilizers are used for example, in amounts of, from about 0.001% to about 30%, from about 0.005% to about 20%, from about 0.01% to about 5%, from about 0.05% to about 2% or from about 0.1% to about 1%, by weight, based on the weight of the polymer to be stabilized.

c. an antioxidant of the instant invention (in the concentration range from about 0.0005% to about 50%, from about 0.0001% to about 50%, from about 0.005% to about 10%, from about 0.05% to about 5% or from about 0.01% to about 1%) along with low valent phosphorus compounds, aromatic amine antioxidants, copper salts alone or in combination with one or more alkali or alkaline earth metal halide salts, and transition metals and their oxides in a. and b. above. These additives are used for example, in amounts of, from about 0.001% to about 30%, from about 0.005% to about 20%, from about 0.01% to about 5%, from about 0.05% to about 2% or from about 0.1% to about 1%, by weight, based on the weight of the polymer to be stabilized.

d. an antioxidant of the instant invention (in the concentration range from about 0.0005% to about 50%, from about 0.0001% to about 50%, from about 0.005% to about 10%, from about 0.05% to about 5% or from about 0.01% to about 1%) along with polyfunctional epoxides, polyhydric alcohols, and polyfunctional carboxylic acids and anhydrides. These additives are used for example, in amounts of, from about 0.001% to about 30%, from about 0.005% to about 20%, from about 0.01% to about 5%, from about 0.05% to about 2% or from about 0.1% to about 1%, by weight, based on the weight of the polymer to be stabilized.

e. an antioxidant of the instant invention in combination with other known commercially available antioxidants, such as, for example, Irganox® 1010, Irganox® 1330, Irganox® 1076, Irganox® 1135, aromatic amines antioxidants Naugard 445, Naugard A, Winstay 29 or other antioxidants described above or incorporated herein by reference along with the formulations described in a.-d. above.

EXEMPLIFICATION

Example 1: Synthesis of 3-(3,5-Di-tert-butyl-4-hydroxy-phenyl)-N-(1,4-dimethyl-pentyl)-N-(4-phenylamino-phenyl)-propionamide Using 3-(3,5-Di-tert-butyl-4-hydroxy-phenyl)-propionyl Chloride In a one liter of 3-neck round bottom flask, 25.0 g of N-(1,4-Dimethyl-pentyl)-N'-phenyl-benzene-1,4-diamine was dissolved in 200 ml of anhydrous toluene under argon atmosphere. 25 ml of triethyl amine was added drop wise. 30 g of 3-(3,5-Di-tert-butyl-4-hydroxy-phenyl)-propionyl chloride was dissolved in 200 ml of anhydrous toluene and was transferred drop wise to the round bottom flask containing N-(1,4-Dimethyl-pentyl)-N'-phenyl-benzene-1,4-diamine under argon atmosphere. Reactants were heated to reflux temperature of toluene (111° C.). The reaction was completed in 6 hours. The crude product thus obtained was purified by washing with cold hexane to get 29.5 g of 3-(3,5-Di-tert-butyl-4-hydroxy-phenyl)-N-(1,4-dimethyl-pentyl)-N-(4-phenylamino-phenyl)-propionamide and the structure was confirmed by 500 MHz $^1$H NMR spectroscopy with resonance peaks at 0.9-1.1 (m), 1.33(m), 1.41 (s), 1.61 (m), 1.91 (m), 2.3 (t), 2.85 (t), 3.88 (m), 6.81 (m), 6.86 (s), 7.01 (m), 7.13-7.15 (m), 7.32-7.35 (m) ppm.

Example 2: Synthesis of 3-(3,5-Di-tert-butyl-4-hydroxy-phenyl)-N-(1,3-dimethyl-butyl)-N-(4-phenylamino-phenyl)-propionamide Using 3-(3,5-Di-tert-butyl-4-hydroxy-phenyl)-propionyl Chloride In a 100 ml of 3-neck round bottom flask, 1.0 g of N-(1,3-Dimethyl-butyl)-N'-phenyl-benzene-1,4-diamine was dissolved in 20 ml of anhydrous toluene under argon atmosphere. 0.75 ml of triethyl amine was added drop wise. 1.4 g of 3-(3,5-Di-tert-butyl-4-hydroxy-phenyl)-propionyl chloride was dissolved in 20 ml of anhydrous toluene and was transferred drop wise to the round bottom flask containing N-(1,3-Dimethyl-butyl)-N'-phenyl-benzene-1,4-diamine under argon atmosphere. Reactants were heated to reflux temperature of toluene (111° C.). The reaction was completed in 5 hours. The crude product thus obtained was purified by washing with cold hexane to get 1.5 g of 3-(3,5-Di-tert-butyl-4-hydroxy-phenyl)-N-(1,3-dimethyl-butyl)-N-(4-phenylamino-phenyl)-propionamide and the structure was confirmed by 500 MHz $^1$H NMR with peaks appearing at 0.9-1.1 (m), 1.42 (s), 1.61 (m), 1.94 (m), 2.28 (t), 2.83 (t), 3.89 (m), 6.83 (m), 6.88 (s), 7.03 (m), 7.13-7.15 (m), 7.32-7.35 (m) ppm.

Example 3: Synthesis of 3-(3,5-Di-tert-butyl-4-hydroxy-phenyl)-N-isopropyl-N-(4-phenylamino-phenyl)-propionamide Using 3-(3,5-Di-tert-butyl-4-hydroxy-phenyl)-propionyl Chloride In a 100 ml of 3-neck round bottom flask, 1.0 g of N-Isopropyl-N'-phenyl-benzene-1,4-diamine is dissolved in 20 ml of anhydrous toluene under argon atmosphere. 0.75 ml of triethyl amine is added drop wise. 1.3 g of 3-(3,5-Di-tert-butyl-4-hydroxy-phenyl)-propionyl chloride is dissolved in 20 ml of anhydrous toluene and is transferred drop wise to the round bottom flask containing N-Isopropyl-N'-phenyl-benzene-1,4-diamine. Reactants are heated to reflux temperature of toluene (111° C.). The reaction is completed in 5 hours. The crude product thus obtained is purified by washing with cold hexane to get 1.4 g of 3-(3,5-Di-tert-butyl-4-hydroxy-phenyl)-N-isopropyl-N-(4-phenylamino-phenyl)-propionamide.

Example 4: Synthesis of 3-(3,5-Di-tert-butyl-4-hydroxy-phenyl)-N-(4-phenylamino-phenyl)-propionamide Using 3-(3,5-Di-tert-butyl-4-hydroxy-phenyl)-propionyl Chloride In a 100 ml of 3-neck round bottom flask, 1.0 g of N-Phenyl-benzene-1,4-diamine is dissolved in 20 ml of anhydrous toluene under argon atmosphere. 0.75 ml of triethyl amine is added drop wise. 1.2 g of 3-(3,5-Di-tert-butyl-4-hydroxy-phenyl)-propionyl chloride is dissolved in 20 ml of anhydrous toluene and is transferred drop wise to the round bottom flask containing N-Phenyl-benzene-1,4-diamine. Reactants are heated to reflux temperature of toluene (111° C.). The reaction is completed in 4 hours. The crude product thus obtained is purified by washing with cold hexane to get 1.2 g of 3-(3,5-Di-tert-butyl-4-hydroxy-phenyl)-N-(4-phenylamino-phenyl)-propionamide.

Example 5: Synthesis of 3-(3,5-Di-tert-butyl-4-hydroxy-phenyl)-N-(1,4-dimethyl-pentyl)-N-(4-phenylamino-phenyl)-propionamide Using 3-(3,5-Di-tert-butyl-4-hydroxy-phenyl)-propionic Acid In a set-up of Dean-Stark apparatus, 1.0 g of N-(1,4-Dimethyl-pentyl)-N'-phenyl-benzene-1,4-diamine is dissolved in 40 ml of anhydrous toluene. 1.4 g of 3-(3,5-ditert-butyl-4-hydroxyphenyl) propanoic acid and a catalytic amount of boric acid (0.024 g) are added to the flask. The reaction mixture is refluxed under argon atmosphere for 15 hours. The crude product thus obtained is purified to get 3-(3,5-Di-tert-butyl-4-hydroxy-phenyl)-N-(1,4-dimethyl-pentyl)-N-(4-phenylamino-phenyl)-propionamide.

Example 6: Synthesis of 3-(3,5-Di-tert-butyl-4-hydroxy-phenyl)-N-(1,3-dimethyl-butyl)-N-(4-phenylamino-phenyl)-propionamide Using 3-(3,5-Di-tert-butyl-4-hydroxy-phenyl)-propionic Acid In a set-up of Dean-Stark apparatus, 1.0 g of N-(1,3-Dimethyl-butyl)-N'-phenyl-benzene-1,4-diamine is dissolved in 40 ml of anhydrous toluene. 1.3 g of 3-(3,5-ditert-butyl-4-hydroxyphenyl) propanoic acid and a catalytic amount of boric acid (0.024 g) are added to the flask. The reaction mixture is refluxed under argon atmosphere for 15 hours. The crude product thus obtained is purified to get 3-(3,5-Di-tert-butyl-4-hydroxy-phenyl)-N-(1,3-dimethyl-butyl)-N-(4-phenylamino-phenyl)-propionamide.

Example 7: Synthesis of 3-(3,5-Di-tert-butyl-4-hydroxy-phenyl)-N-isopropyl-N-(4-phenylamino-phenyl)-propionamide Using 3-(3,5-Di-tert-butyl-4-hydroxy-phenyl)-propionic Acid In a set-up of Dean-Stark apparatus, 1.0 g of N-Isopropyl-N'-phenyl-benzene-1,4-diamine is dissolved in 40 ml of anhydrous toluene. 1.3 g of 3-(3,5-ditert-butyl-4-hydroxyphenyl) propanoic acid and a catalytic amount of boric acid (0.024 g) are added to the flask. The reaction mixture is refluxed under argon atmosphere for 15 hours. The crude product thus obtained is purified to get 3-(3,5-Di-tert-butyl-4-hydroxy-phenyl)-N-isopropyl-N-(4-phenylamino-phenyl)-propionamide.

Example 8: Synthesis of 3-(3,5-Di-tert-butyl-4-hydroxy-phenyl)-N-(4-phenylamino-phenyl)-propionamide using 3-(3,5-Di-tert-butyl-4-hydroxy-phenyl)-propionic Acid In a set-up of Dean-Stark apparatus, 1.0 g of N-Phenyl-benzene-1,4-diamine is dissolved in 40 ml of anhydrous toluene. 1.3 g of 3-(3,5-ditert-butyl-4-hydroxyphenyl) propanoic acid and a catalytic amount of boric acid (0.024 g) are added to the flask. The reaction mixture is refluxed under argon atmosphere for 15 hours. The crude product thus obtained is purified to get 3-(3,5-Di-tert-butyl-4-hydroxy-phenyl)-N-(4-phenylamino-phenyl)-propionamide.

Example 9: Synthesis of 3-(3,5-Di-tert-butyl-4-hydroxy-phenyl)-N-(1,4-dimethyl-pentyl)-N-(4-phenylamino-phenyl)-propionamide Using 3-(3,5-Di-tert-butyl-4-hydroxy-phenyl)-propionic Acid Methyl Ester In a set-up of Dean-Stark apparatus, 1.0 g of N-(1,4-Dimethyl-pentyl)-N'-phenyl-benzene-1,4-diamine is dissolved in 40 ml of anhydrous toluene. 1.4 g of 3-(3,5-Di-tert-butyl-4-hydroxy-phenyl)-propionic acid methyl ester and a catalytic amount of boric acid (0.024 g) are added to the flask. 10 g of 4 A° molecular sieves are added in the dean stark to absorb the eliminated methanol during the course of reaction. The reaction mixture is refluxed under argon atmosphere for 15 hours. The crude product thus obtained is purified to get 3-(3,5-Di-tert-butyl-4-hydroxy-phenyl)-N-(1,4-dimethyl-pentyl)-N-(4-phenylamino-phenyl)-propionamide.

Example 10: Synthesis of 3-(3,5-Di-tert-butyl-4-hydroxy-phenyl)-N-(1,3-dimethyl-butyl)-N-(4-phenylamino-phenyl)-propionamide Using 3-(3,5-Di-tert-butyl-4-hydroxy-phenyl)-propionic Acid Methyl Ester In a set-up of Dean-Stark apparatus, 1.0 g of N-(1,3-Dimethyl-butyl)-N'-phenyl-benzene-1,4-diamine is dissolved in 40 ml of anhydrous toluene. 1.3 g of 3-(3,5-Di-tert-butyl-4-hydroxy-phenyl)-propionic acid methyl ester and a catalytic amount of boric acid (0.024 g) are added to the flask. 10 g of 4 A° molecular sieves are added in the dean stark to absorb the eliminated methanol during the course of reaction. The reaction mixture is refluxed under argon atmosphere for 15 hours. The crude product thus obtained is purified to get 3-(3,5-Di-tert-butyl-4-hydroxy-phenyl)-N-(1,3-dimethyl-butyl)-N-(4-phenylamino-phenyl)-propionamide.

Example 11: Synthesis of 3-(3,5-Di-tert-butyl-4-hydroxy-phenyl)-N-isopropyl-N-(4-phenylamino-phenyl)-propionamide Using 3-(3,5-Di-tert-butyl-4-hydroxy-phenyl)-propionic Acid Methyl Ester In a set-up of Dean-Stark apparatus, 1.0 g of N-Isopropyl-N'-phenyl-benzene-1,4-diamine is dissolved in 40 ml of anhydrous toluene. 1.3 g of 3-(3,5-Di-tert-butyl-4-hydroxy-phenyl)-propionic acid methyl ester and a catalytic amount of boric acid (0.024 g) are added to the flask. 10 g of 4 A° molecular sieves are added in the dean stark to absorb the eliminated methanol during the course of reaction. The reaction mixture is refluxed under argon atmosphere for 15 hours. The crude product thus obtained is purified to get 3-(3,5-Di-tert-butyl-4-hydroxy-phenyl)-N-isopropyl-N-(4-phenylamino-phenyl)-propionamide.

Example 12: Synthesis of 3-(3,5-Di-tert-butyl-4-hydroxy-phenyl)-N-(4-phenylamino-phenyl)-propionamide Using 3-(3,5-Di-tert-butyl-4-hydroxy-phenyl)-propionic Acid Methyl Ester In a set-up of Dean-Stark apparatus, 1.0 g of N-Phenyl-benzene-1,4-diamine is dissolved in 40 ml of anhydrous toluene. 1.3 g of 3-(3,5-Di-tert-butyl-4-hydroxy-phenyl)-propionic acid methyl ester and a catalytic amount of boric acid (0.024 g) are added to the flask. 10 g of 4 A° molecular sieves are added in the dean stark to absorb the eliminated methanol during the course of reaction. The reaction mixture is refluxed under argon atmosphere for 15 hours. The crude product thus obtained is purified to get 3-(3,5-Di-tert-butyl-4-hydroxy-phenyl)-N-(4-phenylamino-phenyl)-propionamide.

Example 13: Synthesis of 3-(3,5-Di-tert-butyl-4-hydroxy-phenyl)-N-(1-methyl-heptyl)-N-(4-phenylamino-phenyl)-propionamide Using 3-(3,5-Di-tert-butyl-4-hydroxy-phenyl)-propionyl Chloride In a 100 ml of 3-neck round bottom flask, 1.0 g of N-(1-Methyl-heptyl)-N'-phenyl-benzene-1,4-diamine was dissolved in 20 ml of anhydrous toluene under argon atmosphere. 0.75 ml of triethyl amine was added drop wise. 1.4 g of 3-(3,5-Di-tert-butyl-4-hydroxy-phenyl)-propionyl chloride was dissolved in 20 ml of anhydrous toluene and was transferred drop wise to the round bottom flask containing N-(1-Methyl-heptyl)-N'-phenyl-benzene-1,4-diamine under argon atmosphere. Reactants were heated to reflux temperature of toluene (111° C.). The reaction was completed in 5 hours. The crude product thus obtained was purified by washing with cold hexane to get 1.5 g of 3-(3,5-Di-tert-butyl-4-hydroxy-phenyl)-N-(1-methyl-heptyl)-N-(4-phenylamino-phenyl)-propionamide. The structure was confirmed by 500 MHz $^1$H NMR with peaks appearing at 0.91 (m), 1.3-1.41 (m), 1.44 (s), 1.61 (m), 2.3 (t), 2.85 (t), 3.88 (m), 6.81 (m), 6.86 (s), 7.01 (m), 7.13-7.15 (m), 7.32-7.35 (m) ppm.

Example 14: Synthesis of 3-(3,5-Di-tert-butyl-4-hydroxy-phenyl)-N-(1-methyl-heptyl)-N-(4-phenylamino-phenyl)-propionamide Using 3-(3,5-Di-tert-butyl-4-hydroxy-phenyl)-propionic Acid In a set-up of Dean-Stark apparatus, 1.0 g of N-(1-Methyl-heptyl)-N'-phenyl-benzene-1,4-diamine is dissolved in 40 ml of anhydrous toluene. 1.3 g of 3-(3,5-ditert-butyl-4-hydroxyphenyl) propanoic acid and a catalytic amount of boric acid (0.024 g) are added to the flask. The reaction mixture is refluxed under argon atmosphere for 15 hours. The crude product thus obtained is purified to get 3-(3,5-Di-tert-butyl-4-hydroxy-phenyl)-N-(1-methyl-heptyl)-N-(4-phenylamino-phenyl)-propionamide.

Example 15: Synthesis of 3-(3,5-Di-tert-butyl-4-hydroxy-phenyl)-N-(1-methyl-heptyl)-N-(4-phenylamino-phenyl)-propionamide Using 3-(3,5-Di-tert-butyl-4-hydroxy-phenyl)-propionic Acid Methyl Ester In a set-up of Dean-Stark apparatus, 1.0 g of N-(1-Methyl-heptyl)-N'-phenyl-benzene-1,4-diamine is dissolved in 40 ml of anhydrous toluene. 1.3 g of 3-(3,5-Di-tert-butyl-4-hydroxy-phenyl)-propionic acid methyl ester and a catalytic amount of boric acid (0.024 g) are added to the flask. 10 g of 4 A° molecular sieves are added in the dean stark to absorb the eliminated methanol during the course of reaction. The reaction mixture is refluxed under argon atmosphere for 15 hours. The crude product thus obtained is purified to get 3-(3,5-Di-tert-butyl-4-hydroxy-phenyl)-N-(1-methyl-heptyl)-N-(4-phenylamino-phenyl)-propionamide.

Example 16: Reaction Product of Synthesis of Mixture of N-(1,3-Dimethyl-butyl)-N'-phenyl-benzene-1, 4-diamine and N-(1-Methyl-heptyl)-N'-phenyl-benzene-1,4-diamine Using 3-(3,5-Di-tert-butyl-4-hydroxy-phenyl)-propionyl Chloride In a 100 ml of 3-neck round bottom flask, 0.5 g of N-(1,3-Dimethyl-butyl)-N'-phenyl-benzene-1,4-diamine and 0.5 g of N-(1-Methyl-heptyl)-N'-phenyl-benzene-1,4-diamine were dissolved in 20 ml of anhydrous toluene under argon atmosphere. 0.8 ml of triethyl amine was added. 1.5 g of 3-(3,5-Di-tert-butyl-4-hydroxy-phenyl)-propionyl chloride was dissolved in 20 ml of anhydrous toluene and was transferred drop wise to the round bottom flask containing N-(1,3-Dimethyl-butyl)-N'-phenyl-benzene-1,4-diamine and N-(1-Methyl-heptyl)-N'-phenyl-benzene-1,4-diamine under argon atmosphere. Reactants were heated to reflux temperature of toluene (111° C.). The reaction was completed in 1 hour. The crude product thus obtained was purified by washing with cold hexane to get 1.4 g of reaction product of 3-(3,5-Di-tert-butyl-4-hydroxy-phenyl)-N-(1,3-dimethyl-butyl)-N-(4-phenylamino-phenyl)-propionamide and 3-(3,5-Di-tert-butyl-4-hydroxy-phenyl)-N-(1-methyl-heptyl)-N-(4-phenylamino-phenyl)-propionamide. The structure was confirmed by 500 MHz $^1$H NMR with peaks appearing at 0.9-1.1 (m), 1.3-1.41 (m), 1.44 (s), 1.61 (m), 1.94 (m), 2.3 (t), 2.85 (t), 3.88 (m), 6.86 (s), 7.01 (m), 7.13-7.15 (m), 7.32-7.35 (m) ppm.

Example 17: Reaction Product of Synthesis of Mixture of N-(1,3-Dimethyl-butyl)-N'-phenyl-benzene-1,4-diamine and N-(1-Methyl-heptyl)-N'-phenyl-benzene-1,4-diamine using 3-(3,5-Di-tert-butyl-4-hydroxy-phenyl)-propionic Acid In a set-up of Dean-Stark apparatus, 0.5 g of N-(1,3-Dimethyl-butyl)-N'-phenyl-benzene-1,4-diamine and 0.5 g of N-(1-Methyl-heptyl)-N'-phenyl-benzene-1,4-diamine are dissolved in 40 ml of anhydrous toluene. 1.4 g of 3-(3,5-ditert-butyl-4-hydroxyphenyl) propanoic acid and a catalytic amount of boric acid (0.024 g) are added to the flask. The reaction mixture is refluxed under argon atmosphere for 15 hours. The crude product thus obtained is purified to get reaction product of 3-(3,5-Di-tert-butyl-4-hydroxy-phenyl)-N-(1,3-dimethyl-butyl)-N-(4-phenylamino-phenyl)-propionamide and 3-(3,5-Di-tert-butyl-4-hydroxy-phenyl)-N-(1-methyl-heptyl)-N-(4-phenylamino-phenyl)-propionamide.

Example 18: Reaction Product of Synthesis of Mixture of N-(1,3-Dimethyl-butyl)-N'-phenyl-benzene-1, 4-diamine and N-(1-Methyl-heptyl)-N'-phenyl-benzene-1,4-diamine Using 3-(3,5-Di-tert-butyl-4-hydroxy-phenyl)-propionic acid methyl ester In a set-up of Dean-Stark apparatus, 0.5 g of N-(1,3-Dimethyl-butyl)-N'-phenyl-benzene-1,4-diamine and 0.5 g of N-(1-Methyl-heptyl)-N'-phenyl-benzene-1,4-diamine are dissolved in 40 ml of anhydrous toluene. 1.3 g of 3-(3,5-Di-tert-butyl-4-hydroxy-phenyl)-propionic acid methyl ester and a catalytic amount of boric acid (0.024 g) are added to the flask. 10 g of 4 A° molecular sieves are added in the dean stark to absorb the eliminated methanol during the course of reaction. The reaction mixture is refluxed under argon atmosphere for 15 hours. The crude product thus obtained is purified to get reaction product of 3-(3,5-Di-tert-butyl-4-hydroxy-phenyl)-N-(1,3-dimethyl-butyl)-N-(4-phenylamino-phenyl)-propionamide and 3-(3,5-Di-tert-butyl-4-hydroxy-phenyl)-N-(1-methyl-heptyl)-N-(4-phenylamino-phenyl)-propionamide.

Example 19: Synthesis of 4-(3-{4,6-Bis-[(1,3-dimethyl-butyl)-(4-phenylamino-phenyl)-amino]-[1,3,5]triazin-2-yloxy}-propyl)-2,6-di-tert-butyl-phenol using 2,4,6-Trichloro-[1,3,5]triazine In a 100 ml of 3-neck round bottom flask, 1.0 g of 2,4,6-Trichloro-[1,3,5]triazine was dissolved in 25 ml of anhydrous tetrahydrofuran under nitrogen atmosphere. 3.1 ml of triethyl amine was added. 4.45 g of N-(1,3-Dimethyl-butyl)-N'-phenyl-benzene-1,4-diamine was transferred to the round bottom flask under nitrogen atmosphere. Reactants were heated to reflux temperature of tetrahydrofuran (65° C.). The reaction was completed in 20 hours. The crude product thus obtained was purified to get 4.1 g of 4-(3-{4,6-Bis-[(1,3-dimethyl-butyl)-(4-phenylamino-phenyl)-amino]-[1,3,5]triazin-2-yloxy}-propyl)-2,6-di-tert-butyl-phenol. The structure was confirmed by 500 MHz $^1$H NMR with peaks appearing at 1.34 (s), 2.54 (t), 2.64 (t), 6.72 (s), 6.77 (d), 6.81 (s), 6.98 (d) ppm.

Example 20: Synthesis of 4-[3-({4,6-bis[3-(3,5-ditert-butyl-4-hydroxyphenyl)propoxy]-1,3,5-triazin-2-yl}oxy)propyl]-2,6-ditert-butylphenol Using 2,4, 6-Trichlo-[1,3,5]triazine In a 100 ml of 3-neck round bottom flask, 1.0 g of 2,4,6-Trichloro-[1,3,5]triazine is dissolved in 25 ml of anhydrous tetrahydrofuran under nitrogen atmosphere. 3.1 ml of triethyl amine is added. 4.3 g of 2,6-Di-tert-butyl-4-(3-hydroxy-propyl)-phenol is transferred to the round bottom flask under nitrogen atmosphere. Reactants are heated to reflux temperature of tetrahydrofuran (65° C.). The reaction is completed in 15 hours. The crude product thus obtained is purified to get 4-[3-({4,6-bis[3-(3,5-ditert-butyl-4-hydroxyphenyl)propoxy]-1,3,5-triazin-2-yl}oxy)propyl]-2,6-ditert-butylphenol.

Example 21: Synthesis of 4-[3-({4,6-bis[(4-anilinophenyl)(1,3-dimethylbutyl)amino]-1,3,5-triazin-2-yl}oxy)propyl]-2,6-ditert-butylphenol Using 2,4,6-Trichloro-[1,3,5]triazine In a 100 ml of 3-neck round bottom flask, 1.0 g of 2,4,6-Trichloro-[1,3,5]triazine is dissolved in 25 ml of anhydrous tetrahydrofuran under nitrogen atmosphere. Flask is kept in ice bath maintained at 0° C. using salt. 3.1 ml of triethyl amine is added. 1.6 g of 2,6-Di-tert-butyl-4-(3-hydroxy-propyl)-phenol is transferred to the round bottom flask under nitrogen atmosphere. It is stirred for 4 hours at 0° C. Now 3.1 g of N-(1,3-Dimethyl-butyl)-N'-phenyl-benzene-1,4-diamine is transferred to the round bottom flask under nitrogen atmosphere. Reactants are heated to reflux temperature of tetrahydrofuran (65° C.). The reaction is completed in 15 hours. The crude product thus obtained is purified to get 4-[3-({4,6-bis[(4-anilinophenyl)(1,3-dimethylbutyl)amino]-1,3,5-triazin-2-yl}oxy)propyl]-2,6-ditert-butylphenol.

Example 22: Synthesis of 4-[3-({4-[(4-anilinophenyl)(1,3-dimethylbutyl)amino]-6-[3-(3,5-ditert-butyl-4-hydroxyphenyl)-propoxy]-1,3,5-triazin-2-yl}oxy)propyl]-2,6-ditert-butylphenol Using 2,4,6-Trichloro-[1,3,5]triazine In a 100 ml of 3-neck round bottom flask, 1.0 g of 2,4,6-Trichloro-[1,3,5]triazine is dissolved in 25 ml of anhydrous tetrahydrofuran under nitrogen atmosphere. Flask is kept in ice bath maintained at 0° C. using salt. 3.1 ml of triethyl amine is added. 1.7 g of N-(1,3-Dimethyl-butyl)-N'-phenyl-benzene-1,4-diamine is transferred to the round bottom flask under nitrogen atmosphere. It is stirred for 4 hours at 0° C. Now 3.0 g of 2,6-Di-tert-butyl-4-(3-hydroxy-propyl)-phenol is transferred to the round bottom flask under nitrogen atmosphere. Reactants are heated to reflux temperature of tetrahydrofuran (65° C.). The reaction is completed in 15 hours. The crude product thus obtained is purified to get 4-[3-({4-[(4-anilinophenyl)(1,3-dimethylbutyl)amino]-6-[3-(3,5-ditert-butyl-4-hydroxyphenyl)-propoxy]-1,3,5-triazin-2-yl}oxy)propyl]-2,6-ditert-butylphenol.

Example 23: Synthesis of N,N',N"-Tris-(1,3-dimethyl-butyl)-N,N',N"-tris-(4-phenylamino-phenyl)-propane-1,2,3-triamine using 1,2,3-Trichloro-propane In a 100 ml of 3-neck round bottom flask, 1.0 g of 1,2,3-Trichloro-propane is dissolved in 25 ml of anhydrous toluene under nitrogen atmosphere. 3.0 ml of triethyl amine is added. 5.8 g of N-(1,3-Dimethyl-butyl)-N'-phenyl-benzene-1,4-diamine is transferred to the round bottom flask under nitrogen atmosphere. Reactants are heated to reflux temperature of toluene (110° C.). The reaction is completed in 20 hours. The crude product thus obtained is purified to get 4.8 g of N,N',N"-Tris-(1,3-dimethyl-butyl)-N,N',N"-tris-(4-phenylamino-phenyl)-propane-1,2,3-triamine.

Example 24: Synthesis of 4-[3-({3,5-bis[3-(3,5-ditert-butyl-4-hydroxyphenyl)propoxy]pentyl}oxy)propyl]-2,6-ditert-butylphenol Using 1,2,3-Trichloro-propane In a 100 ml of 3-neck round bottom flask, 1.0 g of 1,2,3-Trichloro-propane is dissolved in 25 ml of anhydrous toluene under nitrogen atmosphere. 3.2 ml of triethyl amine is added. 5.7 g of 2,6-Di-tert-butyl-4-(3-hydroxy-propyl)-phenol is transferred to the round bottom flask under nitrogen atmosphere. Reactants are heated to reflux temperature of toluene (110° C.). The reaction is completed in 20 hours. The crude product thus obtained is purified to get 4-[3-({3,5-bis[3-(3,5-ditert-butyl-4-hydroxyphenyl)propoxy]pentyl}oxy)propyl]-2,6-ditert-butylphenol.

Example 25: Synthesis of 2,6-Di-tert-butyl-4-[3-(2-[(1,3-dimethyl-butyl)-(4-phenylamino-phenyl)-amino]-1-{[(1,3-dimethyl-butyl)-(4-phenylamino-phenyl)-amino]-methyl}-ethoxy)-propyl]-phenol using 1,2,3-Trichloro-propane In a 100 ml of 3-neck round bottom flask, 1.0 g of 1,2,3-Trichloro-propane is dissolved in 25 ml of anhydrous tetrahydrofuran under nitrogen atmosphere. Flask is kept in ice bath maintained at 0° C. using salt. 3.2 ml of triethyl amine is added. 3.1 g of N-(1,3-Dimethyl-butyl)-N'-phenyl-benzene-1,4-diamine is transferred to the round bottom flask under nitrogen atmosphere. It is stirred for 10 hours at 0° C. Now 1.5 g of 2,6-Di-tert-butyl-4-(3-hydroxy-propyl)-phenol is transferred to the round bottom flask under nitrogen atmosphere. Reactants are heated to reflux temperature of toluene (110° C.). The reaction is completed in 5 hours. The crude product thus obtained is purified to get 2,6-Di-tert-butyl-4-[3-(2-[(1,3-dimethyl-butyl)-(4-phenylamino-phenyl)-amino]-1-{[(1,3-dimethyl-butyl)-(4-phenylamino-phenyl)-amino]-methyl}-ethoxy)-propyl]-phenol.

Example 26: Synthesis of 4-[3-({3-[(4-anilinophenyl)(1,3-dimethylbutyl)amino]-5-[3-(3,5-ditert-butyl-4-hydroxyphenyl)propoxy]pentyl}oxy)propyl]-2,6-ditert-butylphenol Using 1,2,3-Trichloro-propane In a 100 ml of 3-neck round bottom flask, 1.0 g of 1,2,3-Trichloro-propane is dissolved in 25 ml of anhydrous toluene under nitrogen atmosphere. Flask is kept in ice bath maintained at 0° C. using salt. 3.2 ml of triethyl amine is added. 3.0 g of 2,6-Di-tert-butyl-4-(3-hydroxy-propyl)-phenol is transferred to the round bottom flask under nitrogen atmosphere. It is stirred for 10 hours at 0° C. Now 1.6 g of N-(1,3-Dimethyl-butyl)-N'-phenyl-benzene-1,4-diamine is transferred to the round bottom flask under nitrogen atmosphere. Reactants are heated to reflux temperature of toluene (110° C.). The reaction is completed in 5 hours. The crude product thus obtained is purified to get 4-[3-({3-[(4-anilinophenyl)(1,3-dimethylbutyl)amino]-5-[3-(3,5-ditert-butyl-4-hydroxyphenyl)propoxy]pentyl}oxy)propyl]-2,6-ditert-butylphenol.

The performance of the compound of the present invention (Example 2) was assessed by measuring the oxidative induction time of stabilized samples of vegetable oil at elevated temperature (150° C.) and under high oxygen pressure (500 psi). This is a standard test method in the lubricant industry and is described in ASTM D 6186. Testing was conducted in biolubricant base oils, canola and soybean oil. These base oils differ mainly in their content of polyunsaturated fatty acids which are especially unstable to oxidation, with soybean oil having the highest concentration and hence the lowest inherent oxidative stability.

The performance of the compound in Example 2 was assessed vs. the commercial antioxidant Irganox® L 135 (CAS No. 125643-61-0, BASF) as a control.

The testing results are summarized in Table 1. The antioxidant of Example 2 outperformed the commercial control Irganox® L 135 by a significant margin in both bio-based oils.

In canola oil, the performance enhancement factor for compound of Example 2 over the commercial antioxidant was approximately 3× (compare results for 0.5% Example 2 vs. 1.5% Irganox® L 135). At higher treat levels, the new antioxidant provided a level of performance that could not be achieved with state-of-the-art commercial antioxidants. This result once again suggests that the new antioxidant of this instant invention may enable the use of bio-lubricants based on canola oil in higher performance applications from which they are currently excluded.

In the more oxidatively unstable soybean oil, the performance enhancement factor for compound of Example 2 over the commercial antioxidant was approximately 1.5× (compare results for 1.0% Example 2 with 1.5% Irganox® L 135).

TABLE 1

Performance of antioxidants in biolubricant oils: canola and soybean oils.

| | Oxidative Induction Time (min), 150° C., 500 psi $O_2$, | | | | | |
|---|---|---|---|---|---|---|
| | Canola oil | | | Soybean oil | | |
| Additive | 0.5% | 1.0% | 1.5% | 0.5% | 1.0% | 1.5% |
| Example 2 | 31.3 | 34.1 | 44.0 | 12.3 | 17.3 | 24.1 |
| Irganox® L 135 | 15.7 | 23.5 | 31.2 | 9.8 | 14.9 | 17.6 |

The performance of the present invention was also assessed in ester oils. These synthetic base oils are classified as part of Group V base oil groups according to American Petroleum Institute (API 1509, Appendix E). Synthetic esters are used in different lubricant formulations to improve the properties. The test method described for vegetable and biolubricant oils, ASTM D 6186 method was used to test and compare the performance of the present invention in ester oils of different kinds. The test temperature was 180° C. and oxygen pressure was 500 psi. Both trimethylolpropane (TMP) based polyols ester oil (TruVis Teknor 810TMP) and neopentyl glycols (NPG) polyols ester oil (HATCOL 2957) were added 1000 ppm of antioixdant and tested using ASTM D6186 method at 180° C. and 500 psi $O_2$.

The performance of the compounds in Examples 2, 13, and 16 was assessed vs. the commercial antioxidant Irganox® L 135 (CAS No. 125643-61-0, BASF) as a control in TMP and NPG oils.

The testing results are summarized in Tables 2 and 3. The antioxidants of the present invention Examples 2, 13, and 16 outperformed the commercial control Irganox® L 135 by a significant margin in both ester oils.

TABLE 2

Performance of antioxidants in Group V oils: Polyolester oil, TMP based oil

| Additive | Oxidative Induction Time (min), 180° C., 500 psi $O_2$ Oil: TMP polyol ester oil, 1000 ppm |
|---|---|
| Example 2 | 104.8 |
| Irganox® L 135 | 18.3 |

In synthetic polyolester oil (TMP base oil), the performance enhancement factor for compound of Example 2 over the commercial antioxidant was approximately 5.7× (Table 2). This result once again suggests that the new antioxidant of this instant invention may enable the use of synthetic base lubricant oil in higher performance applications from which they are currently excluded.

TABLE 3

Performance of antioxidants in Group V oils: Polyolester oil, NPG based oil

| Additive | Oxidative Induction Time (min), 180° C., 500 psi $O_2$ Oil: NPG polyol ester oil 1000 ppm |
|---|---|
| Example 2 | 59.5 |
| Example 13 | 60.6 |
| Example 16 | 61.4 |
| Irganox® L 135 | 12.2 |

Table 3 shows all three antioxidants of the present invention outperform over the commercial antioxidant in another type of polyolester, NPG based oil. The performance enhancement factor was approximately 5×.

The performance of the present invention compound (Example 2) was assessed by measuring the oxidative induction time (OIT) of polyolefin samples at elevated temperature (170° C.) and under high oxygen pressure (500 psi). This is a standard test method and is described in ASTM D 5885. The performance of the compound in Example 2 was assessed vs. the commercial antioxidant Irganox® 1010 (CAS No. 6683-19-8) as a control. The stabilized polyolefin samples were prepared by extruding polypropylene (PH350, LyondellBasell) with 1000 ppm antioxidant, 100 ppm of calcium stearate (CaS) (CAS No. 1592-23-0) and 1000 ppm of Irganox® 168 (CAS No. 31570-04-4) using a Randcastle extruder (RCP-0250) at 250° C. in into mini size pellets. These mini pellets were used to test and compare performance of antioxidants in polyolefin.

The testing results are summarized in Table 3. The antioxidant of Example 2 outperformed the commercial control Irganox® 1010 by a significant margin (3×) in stabilized polypropylene.

TABLE 4

Performance of antioxidants in polyolefin: polypropylene.

| Additive* | Oxidative Induction Time (min), ASTM D5185 Method 170° C., 500 psi $O_2$ Sample: Polypropylene (PP) 1000 ppm |
|---|---|
| Example 2 | 24.1 |
| Irganox® 1010 | 8.4 |

*formulation: antioxidant 1000 ppm + calcium stearate 1000 ppm + 1000 ppm Irganox® 168

The OIT of the stabilized polyolefin samples (polypropylene, (PP)) was determined according to the procedure of ASTM D 5885. The system used to measure the OIT was TA Instruments Model Q10. The sample and the reference are heated at a constant rate of 20° C./min to reach 170° C. The heating was held isothermally after reaching 170° C. The zero time was taken when the heating was started. The sample cell was purged with oxygen and pressurized to 500 psi of oxygen. The end of the induction period was signaled by an abrupt increase in the sample's evolved heat as recorded by the instrument. OIT was measured from the start of isothermal conditions to the inflection point of the exothermic peak.

What is claimed is:

1. A stabilized lubricant composition, comprising:
   (a) a lubricant or a mixture of lubricants; and
   (b) a composition comprising a mixture of the following compounds:

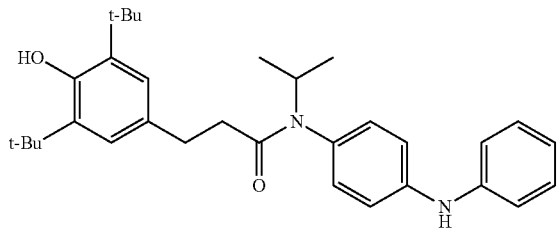
(i)

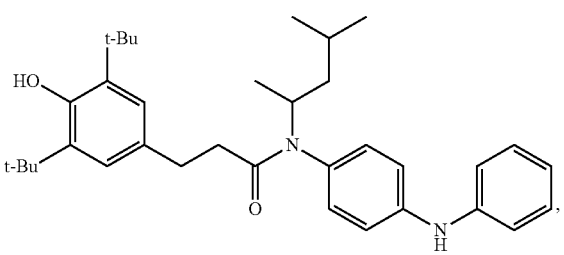
(ii)

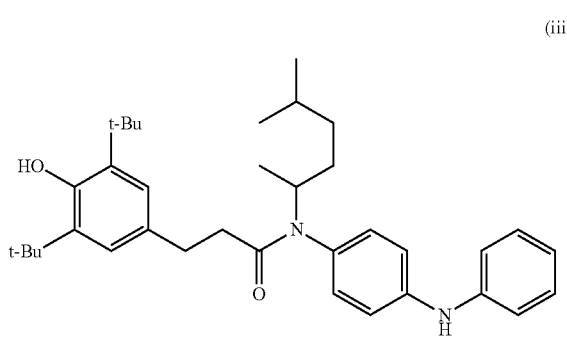
(iii)

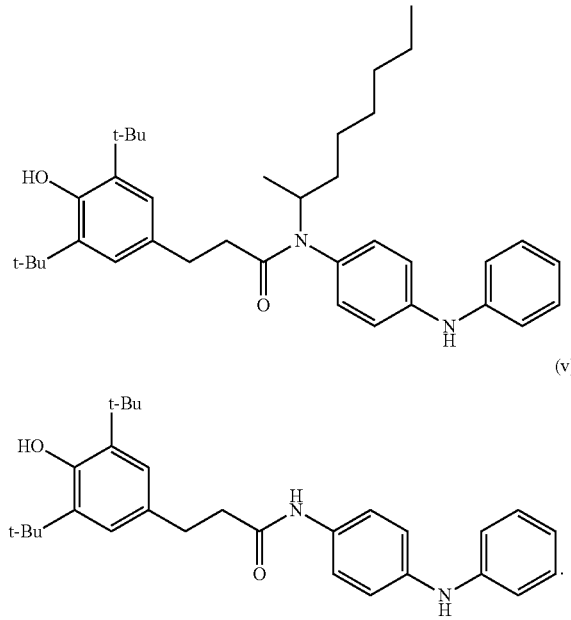
(iv)

(v)

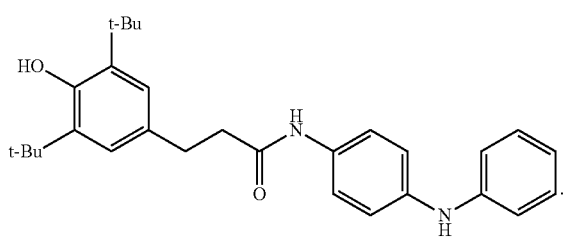

2. The stabilized lubricant composition of claim 1 wherein the antioxidant composition is in an amount 0.05% to 5% by weight of the lubricant composition.

3. The stabilized lubricant composition of claim 1, further containing at least one lubricant additive in an amount 0.05% to 5% by weight of the lubricant composition selected from the group consisting of anti-wear additives, metal deactivating agents, antioxidants, detergents, rust inhibitors, friction modifiers, viscosity modifiers, pour point depressants, corrosion inhibitors, demulsifying regents, and anti-foaming agents.

4. The stabilized lubricant composition of claim 1, wherein the lubricant is selected from the group consisting of petroleum based oils, synthetic oils, biolubricant oils, and biobased oils, and mixtures thereof.

5. The composition in claim 1 where the composition (i):(ii):(iii):(iv) by weight of 1:1:1:1, 0:1:1:1, 1:0:1:1, 1:1:0:1, 1:1:1:0.

6. The composition in claim 1 where the composition by weight of (i):(ii), (i):(iii), (ii):(iii), (ii):(iv), (iii):(iv), (v):(i), (v):(ii), (v):(iii), (v):(iv) is 10:90, 20:80, 30:70,40:60,50:50, 60:40, 70:30, 80:20, or 90:10.

7. The composition in claim 6 wherein the composition by weight of (i):(ii), (i):(iii), (ii):(iii), (ii):(iv), (iii):(iv), (v):(i), (v):(ii), (v):(iii), (v):(iv) is 50:50.

* * * * *